US012285393B2

(12) United States Patent
Lu et al.

(10) Patent No.: US 12,285,393 B2
(45) Date of Patent: Apr. 29, 2025

(54) ROLES OF MODULATORS OF INTERSECTIN-CDC42 SIGNALING IN ALZHEIMER'S DISEASE

(71) Applicant: Qun Lu, Greenville, NC (US)

(72) Inventors: Qun Lu, Greenville, NC (US); Yan-Hua Chen, Greenville, NC (US); Yi Zhu, Greenville, NC (US); Byron Aguilar, Greenville, NC (US)

(73) Assignee: Qun Lu, Greenville, NC (US)

( * ) Notice: Subject to any disclaimer, the term of this patent is extended or adjusted under 35 U.S.C. 154(b) by 219 days.

(21) Appl. No.: 17/942,657

(22) Filed: Sep. 12, 2022

(65) Prior Publication Data

US 2023/0165815 A1   Jun. 1, 2023

Related U.S. Application Data

(62) Division of application No. 16/141,849, filed on Sep. 25, 2018, now Pat. No. 11,439,608.

(60) Provisional application No. 62/562,816, filed on Sep. 25, 2017.

(51) Int. Cl.
*A61K 31/18* (2006.01)
*A61K 31/166* (2006.01)
*A61K 31/343* (2006.01)
*A61K 31/505* (2006.01)
*A61P 25/28* (2006.01)

(52) U.S. Cl.
CPC ............ *A61K 31/18* (2013.01); *A61K 31/166* (2013.01); *A61K 31/343* (2013.01); *A61K 31/505* (2013.01); *A61P 25/28* (2018.01)

(58) Field of Classification Search
CPC .... A61K 31/18; A61K 31/166; A61K 31/343; A61K 31/505; A61P 25/28
USPC ....................................................... 514/275
See application file for complete search history.

(56) References Cited

U.S. PATENT DOCUMENTS

| | | | |
|---|---|---|---|
| 5,628,984 | A | 5/1997 | Boucher, Jr. |
| 8,658,655 | B2 | 2/2014 | Peterson et al. |
| 9,433,663 | B2 | 9/2016 | Zheng |
| 9,642,835 | B2 | 5/2017 | Wandinger-Ness et al. |
| 9,725,417 | B2 | 8/2017 | Chen et al. |
| 9,873,661 | B2 | 1/2018 | Cardozo et al. |
| 11,439,608 | B2 | 9/2022 | Lu et al. |
| 2012/0058992 | A1 | 3/2012 | Cohen et al. |
| 2014/0194451 | A1 | 7/2014 | Lu et al. |
| 2014/0256767 | A1 | 9/2014 | Hu et al. |
| 2019/0040393 | A1 | 2/2019 | Postrel |
| 2019/0091184 | A1 | 3/2019 | Lu et al. |
| 2020/0061037 | A1 | 2/2020 | Hadari et al. |

FOREIGN PATENT DOCUMENTS

| | | |
|---|---|---|
| AU | 2685299 A | 9/1999 |
| AU | 2002302363 B2 | 5/2008 |
| AU | 2009242126 B2 | 3/2014 |
| AU | 2009242113 B2 | 9/2014 |
| AU | 2014217962 A1 | 9/2015 |
| CN | 102796050 B | 7/2014 |
| CN | 109925510 A | 6/2019 |
| EA | 201500836 A1 | 2/2016 |
| EP | 1504760 A1 | 2/2005 |
| EP | 1370543 B1 | 10/2006 |
| EP | 2195304 B1 | 1/2014 |
| EP | 2716292 B1 | 9/2017 |
| EP | 2496226 B1 | 3/2020 |
| JP | 2002504502 A | 2/2002 |
| JP | 2004503462 A | 2/2004 |
| JP | 2013540720 A | 11/2013 |
| JP | 2014205697 A | 10/2014 |
| JP | 6001650 B2 | 10/2016 |
| JP | 6062995 B2 | 1/2017 |
| KR | 20010041605 A | 5/2001 |
| KR | 20130065899 A | 6/2013 |
| KR | 101399056 B1 | 5/2014 |
| NZ | 589304 A | 3/2012 |
| NZ | 589307 A | 4/2012 |
| WO | WO9955667 A1 | 4/1999 |
| WO | WO 2011/022393 A2 | 2/2011 |
| WO | WO 2011/104411 A2 | 9/2011 |

(Continued)

OTHER PUBLICATIONS

Friesland et al PNAS, 2013, 110(4), 1261-1266 (Year: 2013).*
Abramov et al., "β-Amyloid Peptides Induce Mitochondrial Dysfunction and Oxidative Stress in Astrocytes and Death of Neurons through Activation of NADPH Oxidase," J. Neurosci., vol. 24, No. 2, pp. 565-575 (2004).
Aguilar et al., "Inhibition of Cdc42-intersectin interaction by small molecule ZCL367 impedes cancer cell cycle progression, proliferation, migration, and tumor growth," Cancer Biology & Therapy, pp. 1-21 (2018).
Aguilar et al., "Rho GTPases as therapeutic targets in Alzheimer's disease," Alzheimer's Research & Therapy, vol. 9, No. 97, pp. 1-10 (2017).

(Continued)

*Primary Examiner* — Yevgeny Valenrod
(74) *Attorney, Agent, or Firm* — Jenkins, Taylor & Hunt, P.A.

(57) ABSTRACT

Methods of treating Alzheimer's disease and other neurodegenerative and/or neurocognitive and/or neurodevelopmental diseases are described. The methods comprise the administration of compounds that modulate an activity of cell division control protein 42 (Cdc42), such as the interaction between Cdc42 and intersectin (ITSN). Exemplary modulator compounds include thioureas, disulfonamides of fused aromatic systems (e.g., benzofuran), and acyl hydrazones, among others. Some of the modulator compounds act as activators of Cdc42, while others act as inhibitors. In some cases, the modulator compound has dual functionality and the ability of the modulator compound to act as an inhibitor or activator depends on whether or not Cdc42 is already activated in a particular disease stage or biological environment by an upstream activating signal of Cdc42.

1 Claim, 7 Drawing Sheets

(56) References Cited

FOREIGN PATENT DOCUMENTS

| WO | WO2012/027548 A1 | 3/2012 |
|---|---|---|
| WO | WO2014124978 A2 | 8/2014 |
| WO | WO 2019140300 A1 | 7/2019 |
| WO | WO 2018213150 A8 | 1/2020 |

OTHER PUBLICATIONS

Aloizou et al. "Pesticides, Cognitive functions and dementia: A review", Toxicology Letters, vol. 326, pp. 31-51 (2020).
Alzheimer's and Dementia, vol. 9, No. 4, Supp. 1, pp. 893-P894. Abstract No. P4-432 (Year: 2013).
Amano et al., "Identification of Tau and MAP2 as novel substrates of Rho-kinase and myosin phosphatase," J. Neurochem., vol. 87, pp. 780-790 (2003).
Ba et al., "Rho GTPase signaling at the synapse: implications for intellectual disability," Exp. Cell Res. vol. 319 pp. 2368-2374 (2013).
Belfiore et al., "Temporal and regional progression of Alzheimer's disease-like pathology in 3xTg-AD mice," Aging Cell, pp. 1-13 (2019).
Berezovska et al., "Notch1 and Amyloid Precursor Protein Are Competitive Substrates for Presenilin1-dependent γ-Secretase Cleavage," J. Biol. Chem., vol. 276, No. 32, pp. 30018-30023 (2001).
Berge et al., "Pharmaceutical Salts," J. Pharm. Sci., vol. 66, pp. 1-19 (1977).
Blalock et al., "Incipient Alzheimer's disease: Microarray correlation analyses reveal major transcriptional and tumor suppressor responses," Proc. Natl. Acad. Sci. U.S.A., vol. 101, No. 7, pp. 2173-2178 (2004).
Bolognin et al., "The Potential Role of Rho GTPases in Alzheimer's Disease Pathogenesis," Mol. Neurobiol. 2014;50:406-22.
Boo et al., "Rac1 changes the substrate specificity of gamma-secretase between amyloid precursor protein and Notch1," Biochem. Biophys. Res. Commun., vol. 372 pp. 913-917 (2008).
Boquet, "The cytotoxic necrotizing factor 1 (CNF1) from *Escherichia coli*," Toxicon, vol. 39, pp. 1673-1680 (2001).
Borin et al., "Rac1 activation links tau hyperphosphorylation and Aβ dysmetabolism in Alzheimer's disease," Acta Neuropathologica Communications, vol. 6, No. 61 (2018).
Brewer & Torricelli, "Isolation and culture of adult neurons and neurospheres," Nat. Protoc., vol. 2 No. 6, pp. 1490-1498 (2007).
Cannon, J.G., "Analog Design," Chapter Nineteen in Burger's Medicinal Chemistry and Drug Discovery, Fifth Edition, vol. 1: Principles and Practice, Wiley-Interscience, pp. 783-802 (Year: 1995).
Caprioli et al., "Partial Purification and Characterization of an *Escherichia coli* Toxic Factor That Induces Morphological Cell Alterations," Infect. Immun. 1983;39:1300-6.
Cataldo et al., "Endocytic Pathway Abnormalities Precede Amyloid β Deposition in Sporadic Alzheimer's Disease and Down Syndrome: Differential Effects of APOE Genotype and Presenilin Mutations," Am. J. Pathol. 2000; 157:277-86.
Cerri et al., "Activation of Rho GTPases Triggers Structural Remodeling and Functional Plasticity in the Adult Rat Visual Cortex," J. Neurosci. 2011;31:15163-72.
Chou et al., "Identification and Characterization of a Novel Broad-Spectrum Virus Entry Inhibitor," Journal of Virology, vol. 90, No. 9, pp. 4494-4510 (2016).
Cosman et al., "Memantine in the treatment of mild-to-moderate Alzheimer's disease" Expert Opin Pharmacother. Vo. 8 pp. 203-214 (2007).
Cui et al., "Elevated IQGAP1 and CDC42 levels correlate with tumor malignancy of human glioma," Oncology Reports, vol. 37 pp. 768-776 (2017).
Cummings, J., et al., "The "rights" of precision drug development for Alzheimer's disease," Alzheimer's Research & Therapy, vol. 11, No. 76, pp. 1-14 (2019).
Datta et al., "Altered Expression of CDC42 Signaling Pathway Components in Cortical Layer 3 Pyramidal Cells in Schizophrenia,"
Author manuscript, pp. 1-22, published in final edited form in Biol. Psychiatry, vol. 78, No. 11, pp. 775-785 (2015).
Daubon et al., "Invadopodia and rolling-type motility are specific features of highly invasive p190bcr-abl," European Journal of Cell Biology, vol. 91, pp. 978-987 (2012).
Davis et al., "Mapping Cofilin-Actin Rods in Stressed Hippocampal Slices and the Role of cdc42 in Amyloid-β-Induced Rods", Journal of Alzheimer's Disease, 18(1) pp. 35-50 (2009).
Deacon et al., "Age-dependent and -independent behavioral deficits in Tg2576 mice," Behavioural Brain Research, vol. 189 pp. 126-138 (2008).
Deacon et al., "Hippocampal lesions, species-typical behaviours and anxiety in mice," Behavioural Brain Research, vol. 156, pp. 241-249 (2005).
Deacon, "Assessing Burrowing, Nest Construction, and Hoarding in Mice," Journal of Visualized Experiments, vol. 59, e2607, pp. 1-10 (2012).
Deacon, "Assessing nest building in mice," Nature Protocols, vol. 1, No. 3 pp. 1117-1119 (2006).
Deacon,R.M.J., et al., "Aged Tg2576 mice are impaired on social memory and open field habituation tests," Behavioural Brain Research, vol. 197 pp. 466-468 (2009).
DeGeer & Lamarche-Vane, "Rho GTPases in neurodegeneration diseases," Exp. Cell Res., vol. 319, pp. 2384-2394 (2013).
Del Pino, "Primary hippocampal neuronal cell death induction after acute and repeated paraquat exposures mediated by AChE variants alteration and cholinergic and glutamatergic transmission disruption," Toxicology, vol. 390, ppl 88-99 (2017).
Diana et al., "Enhancement of learning and memory after activation of cerebral Rho GTPases," Proc. Natl. Acad. Sci. U.S.A. 2007;104:636-41.
Dorostkar et al., "Analyzing dendritic spine pathology in Alzheimer's disease: problems and opportunities," Acta Neuropathol., vol. 130, pp. 1-19 (2015).
Dunckley et al., "Gene expression correlates of neurofibrillary tangles in Alzheimer's disease," Neurobiol. Aging. 2006;27:1359-71.
Désiré et al., "RAC1 Inhibition Targets Amyloid Precursor Protein Processing by γ-Secretase and Decreases Aβ production in Vitro and in Vivo," J. Biol. Chem. 2005;280:37516-25.
Eriksen et al., "NSAIDs and enantiomers of flurbiprofen target γ-secretase and lower Aβ 42 in vivo," J. Clin. Invest. 2003;112:440-9.
Etienne-Manneville & Hall, "Rho GTPases in cell biology," Nature., vol. 420, pp. 629-635 (2002).
Feng et al., "Rho Kinase (ROCK) Inhibitors and Their Therapeutic Potential," J. Med. Chem., vol. 59 pp. 2269-2300 (2016).
Filippis et al., "Modulation of Rho GTPases rescues brain mitochondrial dysfunction, cognitive deficits and aberrant synaptic plasticity in female mice modeling Rett syndrome," Eur. Neuropsychopharmacol., vol. 25, pp. 889-901 (2015).
Fiorentini et al., "Cytoskeletal changes induced in HEp-2 cells by the cytotoxic necrotizing factor of *Escherichia coli*," Toxicon., vol. 26, pp. 1047-1056 (1988).
Fiorentini et al., "*Escherichia coli* Cytotoxic Necrotizing Factor 1: Evidence for Induction of Actin Assembly by Constitutive Activation of the p21 Rho GTPase," Infect. Immun. 1995;63:3936-44.
Flatau et al., "Toxin-induced activation of the G protein p21 Rho by deamidation of glutamine," Nature. vol. 387, pp. 729-733 (1997).
Fournier et al., "Rho Kinase Inhibition Enhances Axonal Regeneration in the Injured CNS," J. Neurosci. 2003;23:1416-23.
Friesland et al., "Small molecule targeting Cdc42-intersectin interaction disrupts Golgi organization and suppresses cell motility," Proc. Natl. Acad. Sci. USA, vol. 110, No. 4, pp. 1261-1266 (2013).
Fuhrmann et al., "Microglial Cx3cr1 knockout prevents neuron loss in a mouse model of Alzheimer's disease," Author manuscript, pp. 1-6, published in final edited form in Nat Neurosci., vol. 13, No. 4, pp. 411-413 (2010).
Gao et al., "Rational design and characterization of a Rac GTPase-specific small molecule inhibitor," Proc. Natl. Acad. Sci. U.S.A. 2004;101:7618-23.

(56) References Cited

OTHER PUBLICATIONS

Geisslinger et al. "Stereoselective disposition of flurbiprofen in healthy subjects following administration of the single enantiomers," Br J Clin Pharmacol. 1994;37:392-4.
Green et al., "Effect of Tarenflurbil on Cognitive Decline and Activities of Daily Living in Patients With Mild Alzheimer Disease: A Randomized Controlled Trial," JAMA. 2009;302:2557-64.
Gunnarson & Bodin, "Occupational Exposure and Neurodegenrative Diseases—A Systematic Literature Review and Meta-Analyses," International Journal of Environmental Research and Public Health, vol. 16, pp. 1-17 (2019).
Hagberg et al., "An update on clinically applicable diagnostic criteria in Rett syndrome. Comments to Rett Syndrome Clinical Criteria Consensus Panel Satellite to European Paediatric Neurology Society Meeting, Baden Baden, Germany, Sep. 11, 2001," Eur. J. Paediatr. Neurol., vol. 6, pp. 293-297 (2002).
Hamano et al., "Pitavastatin decreases tau levels via the inactivation of Rho/ROCK," Neurobiology of aging [Internet]. Elsevier; vol. 33, pp. 2306-2320 (2012).
Hardy & Selkoe, "The Amyloid Hypothesis of Alzheimer's Disease: Progress and Problems on the Road to Therapeutics," Science, vol. 297, pp. 353-356 (2002).
Haskins M, et al., "Early alterations in blood and brain RANTES and MCP-1 expression and the effect of exercise frequency in the 3xTg-AD mouse model of Alzheimer's disease", Neurosci Lett., vol. 610, pp. 165-170 (2016).
Hernández et al., "Adhesion-Dependent Regulation of p190RhoGAP in the Developing Brain by the Abl-Related Gene Tyrosine Kinase," Curr. Biol. 2004; 14:691-6.
Herrero-Garcia et al., "Intersectin scaffold proteins and their role in cell signaling and endocytosis," Biochim. Biophys. Acta. 2017; 1864:23-30.
Herskowitz et al., "Pharmacologic Inhibition of ROCK2 Suppresses Amyloid-β Production in an Alzheimer's Disease Mouse Model," J. Neurosci. 2013;33:19086-98.
Higa et al., "Vibrio parahaemolyticus Effector Proteins Suppress Inflammasome Activation by Interfering with Host Autophagy Signaling," PLoS Pathog vol. 9, No. 1 (2013).
Hong et al., "Complement and Microglia Mediate Early Synapse Loss in Alzheimer Mouse Models," Author Manuscript, pp. 1-14, published in final edited form in Science, vol. 352, No. 6286, pp. 712-716 (2016).
Hong L et al., "Characterization of a Cdc42 Protein Inhibitor and Its Use as a Molecular Probe," J. Biol. Chem. 2013;288:8531-43.
Hori et al., "Cytoskeletal Regulation by AUTS2 in Neuronal Migration and Neuritogenesis," Cell Rep., vol. 9, No. 6, pp. 2166-2179 (2014).
Hsiao et al., "Correlative Memory Deficits, Aβ Elevation, and Amyloid Plaques in Transgenic Mice," Science. 1996;274:99-102.
Hsiao K. "Transgenic mice expressing Alzheimer amyloid precursor proteins," Exp. Gerontol. vol. 33, pp. 883-889 (1998).
Huang et al., "Apolipoprotein E: diversity of cellular origins, structural and biophysical properties, and effects in Alzheimer's disease," J. Mol. Neurosci., vol. 23:189-204 (2004).
Huebner et al., "Maternal Iron Deficiency Worsens the Associative Learning Deficits and Hippocampal and Cerebellar Losses in a Rat Model of Fetal Alcohol Spectrum Disorders," Author manuscript, pp. 1-21, Published in final edited form in Alcohol Clin. Exp. Res., vol. 39, No. 11, pp. 2097-2107 (2015).
Huesa G, Baltrons MAA, Gómez-Ramos P, Morán A, García A, Hidalgo J, et al. Altered distribution of RhoA in Alzheimer's disease and AbetaPP overexpressing mice. J. Alzheimers Dis. 2010;19:37-56.
Hunter et al., "Emerging Roles for Intersectin (ITSN) in Regulating Signaling and Disease Pathways," Int J Mol Sci. 2013;14:7829-52.
Hunter et al., "Intersectin 1 contributes to phenotypes in vivo: implications for Down Syndrome," Author manuscript, pp. 1-10, Published in final edited form in Neuroreport, vol. 22, No. 15, pp. 767-772 (2011).
Ide et al., "Altered cortical CDC42 signaling pathways in schizophrenia: Implications for dendritic spine deficits," Author manuscript, pp. 1-18, Published in final edited form in Biol. Psychiatry, vol. 68, No. 1, pp. 25-32 (2010).
Ivkovich et al., Effects of Early Hippocampal Lesions on Trace, Delay, and Long-Delay Eyeblink Conditioning in Developing Rats Neurobiol. Learn. Mem., vol. 76, pp. 426-446 (2001).
Jans et al., "Processing of amyloid precursor protein as a biochemical link between atherosclerosis and Alzheimer's disease," Cardiovascular & Haematological Disorders—Drugs Targets, vol. 6, pp. 21-34 (2006).
Jones S. B., et al., "Abl tyrosine kinase promotes dendrogenesis by inducing actin cytoskeletal rearrangements in cooperation with Rho family small GTPases in hippocampal neurons", J Neurosci. 24 (39), pp. 8510-8521 (2004).
Kato et al., "Alpha1-chimaerin, a Rac1 GTPase-activating protein, is expressed at reduced mRNA levels in the brain of Alzheimer's disease patients," Neurosci Lett. vol. 591, pp. 19-24 (2015).
Kim et al., "Compromised MAPK signaling in human diseases: an update," Arch. Toxicol. 2015;89:867-82.
Koppel et al., "Optimal treatment of Alzheimer's disease psychosis: challenges and solutions," Neuropsychiatric Disease and Treatment, vol. 10, pp. 2253-2262 (2014).
Kumari et al., "Exosomal protein interactors as emerging therapeutic targets in urothelial bladder cancer," J. Egypt Natl. Canc. Inst., vol. 27, No. 2, pp. 51-58 (2015).
Kuns et al. "Memantine" StatPear Publishing, accessed Jan. 2020, pp. 1-9.
Lee et al., "Selective axonal translation of prenylated Cdc42 mRNA isoform supports axon growth," The Journal of Neuroscience, pp. 1-37 (2018).
Lefort, "Reversing Synapse Loss in Alzheimer's Disease: Rho-Guanosine Triphosphatases and Insights from Other Brain Disorders," Neurotherapeutics. 2015;12:19-28.
Leuchtenberger et al., "Inhibitors of Rho-kinase modulate amyloid-β (AB) secretion but lack selectivity for Aβ42," J. Neurochem. 2006;96:355-65.
Liao et al., "Rho Kinase (ROCK) Inhibitors," J. Cardiovasc. Pharmacol. 2007;50:17-24.
Lim et al., "Ibuprofen effects on Alzheimer pathology and open field activity in APPsw transgenic mice," Neurobiol. Of Aging., vol. 22, pp. 983-991 (2001).
Loizzo et al., "CNF1 Increases Brain Energy Level, Counteracts Neuroinflammatory Markers and Rescues Cognitive Deficits in a Murine Model of Alzheimer's Disease," PLoS ONE. 2013;8:e65898.
Lu et al., "Signaling Through Rho GTPase Pathway as Viable Drug Target," Curr Med Chem., vol. 16, No. 11, pp. 1355-1365 (2009).
Lu Q, et al., "Alzheimer disease-linked presenilin mutation (PS1M146L) induces filamin expression and γ-secretase independent redistribution", Journal of Alzheimer's Disease, 22 (1) pp. 235-245 (2010).
Lu Q, Wood John, "Functional studies of Alzheimer's disease tau protein," J Neurosci., vol. 13, pp. 508-515 (1993).
Luca et al., "Platelets as a peripheral district where to study pathogenetic mechanisms of alzheimer disease: the case of amyloid precursor protein," Eur. J. Pharmacol. vol. 405, pp. 277-283 (2000).
Luo, L., "Rho GTPases in Neuronal Morphogenesis," Nat. Rev. Neurosci., vol. 1, pp. 173-180, 2000.
Lövheim et al., "Herpes simplex infection and the risk of Alzheimer's disease: A nested case-control study," Alzhiemer's & Dementia, vol. 11, pp. 587-592 (2015).
Manterola et al., "1-42 β-Amyloid peptide requires PDK1/nPKC/Rac 1 pathway to induce neuronal death," Transl Psychiatry. 2013;3:e219.
Marco et al., "ARHGEF9 disruption in a female patient is associated with X linked mental retardation and sensory hyperarousal," J. Med. Genet., vol. 45, pp. 100-105 (2008).
Masliah, "Mechanisms of synaptic dysfunction in Alzheimer's disease," Histol. Histopathol., vol. 10, 509-19 (1995).
Matsui et al., "Involvement of the γ-secretase-mediated EphA4 signaling pathway in synaptic pathogenesis of Alzheimer's disease," Brain Pathol., vol. 22, pp. 776-787 (2012).
Matus, "Actin-based plasticity in dendritic spines," Science., vol. 290, pp. 754-758 (2000).

(56) References Cited

OTHER PUBLICATIONS

Mehta, D., et al., "Why do trials for Alzheimer's disease drugs keep failing? A discontinued drug perspective for 2010-2015," Expert Opinion On Investigational Drugs, vol. 26, No. 6, pp. 735-739 (Year: 2017).
Mendoza-Naranjo et al., "Aβ1-42 stimulates actin polymerization in hippocampal neurons through Rac1 and Cdc42 Rho GTPases," J. Cell. Sci. 2007; 120:279-88.
Mesulam, "Neuroplasticity Failure in Alzheimer's Disease: Bridging the Gap between Plaques and Tangles," Neuron. 1999;24:521-9.
Moresco et al., "Abl Family Nonreceptor Tyrosine Kinases Modulate Short-Term Synaptic Plasticity," J. Neurophysiol. 2003;89:1678-87.
Morris, "Developments of a water-maze procedure for studying spatial learning in the rat," Journal of Neuroscience Methods, vol. 11, pp. 47-60 (1984).
Moutin et al., "Palmitoylation of cdc42 Promotes Spine Stabilization and Rescues Spine Density Deficit in a Mouse Model of 22q11.2 Deletion Syndrome," Cereb. Cortex, vol. 27, No. 7, pp. 3618-3629 (2017).
Munoz & Ammit, "Targeting p38 MAPK pathway for the treatment of Alzheimer's disease," Neuropharmacology., vol. 58, pp. 561-568 (2010).
Murray et al., "Psychosis in Alzheimer's Disease," Author Manuscript, pp. 1-24, published in final edited form in Biol Psychiatry, vol. 75, No. 7, pp. 542-552 (2014).
Musilli et al., "Behavioral effects of Rho GTPase modulation in a model of Alzheimer's disease," Behav. Brain Res. vol. 237, pp. 223-229 (2013).
Nadif Kasri et al., "Rho-linked genes and neurological disorders," Pflugers Arch. 2008;455:787-97.
Newey et al., "Rho GTPases, dendritic structure, and mental retardation," J. Neurobiol., vol. 64, pp. 58-74 (2005).
Nicoll, R., "A Brief History of Long-Term Potentiation," Neuron, vol. 93, pp. 281-290 (2017).
Oakley et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation," J. Neurosci. 2006;26:10129-40.
Oddo et al., "Triple-Transgenic Model of Alzheimer's Disease with Plaques and Tangles: Intracellular Aβ and Synaptic Dysfunction," Neuron, vol. 39, pp. 409-421 (2003).
Office Action (Final Rejection) corresponding to U.S. Appl. No. 16/141,849, filed Apr. 16, 2021, pp. 10.
Office Action (Non-Final Rejection) corresponding to U.S. Appl. No. 16/141,849, filed Aug. 10, 2020, pp. 8.
Office Action (Non-Final Rejection) corresponding to U.S. Appl. No. 16/141,849, filed Jul. 3, 2019, pp. 11.
Office Action (Non-Final Rejection) corresponding to U.S. Appl. No. 16/141,849, filed Mar. 3, 2020, pp. 16.
Office Action (Notice of Allowance) corresponding to U.S. Appl. No. 16/141,849, filed Jan. 27, 2022, pp. 9.
Office Action (Notice of Allowance) corresponding to U.S. Appl. No. 16/141,849, filed May 4, 2022, pp. 9.
Office Action (Notice of Allowance) corresponding to U.S. Appl. No. 16/141,849, filed Sep. 22, 2021, pp. 11.
Office Action (Restriction Requirement) corresponding to U.S. Appl. No. 16/141,849, filed Mar. 8, 2019, pp. 6.
Oprea et al., "Novel Activities of Select NSAID R-Enantiomers against Rac1 and Cdc42 GTPases," PLoS ONE. 2015;10:e0142182.
Oswald et al., "Detection of Escherichia coli strains producing cytotoxic necrotizing factor type two (CNF2) by enzyme-linked immunosorbent assay," Vet. Microbiol., vol. 40, pp. 209-218 (1994).
Otth et al., "Modulation of the JNK and p38 pathways by cdk5 protein kinase in a transgenic mouse model of Alzheimer's disease," Neuroreport., vol. 14, pp. 2403-2409 (2003).
O'Kane et al., "Activation of Rho GTPases by synaptic transmission in the hippocampus," J. Neurochem., vol. 87, pp. 1309-1312 (2003).

Palop et al., "A network dysfunction perspective on neurodegenerative diseases," Nature., vol. 443, pp. 768-773 (2006).
Park et al., "Annexin A1 restores Aβ1-42-induced blood-brain barrier disruption through the inhibition of RhoA-ROCK signaling pathway," Aging Cell., vol. 16, No. 1, pp. 149-161 (2017).
Peacock et al., "The Abl-related Gene Tyrosine Kinase Acts through p190RhoGAP to Inhibit Actomyosin Contractility and Regulate Focal Adhesion Dynamics upon Adhesion to Fibronectin," Mol. Biol. Cell. 2007;18:3860-72.
Penzes et al., "Impaired regulation of synaptic actin cytoskeleton in Alzheimer's disease," Brain Res Rev. 2011;67:184-92.
Perrett et al., "Cerebellar Cortex Lesions Disrupt Learning-dependent Timing of Conditioned Eyelid Responses," J. Neuroscience, vol. 13, No. 4, pp. 1708-1718 (1993).
Petratos et al., "The β-amyloid protein of Alzheimer's disease increases neuronal CRMP-2 phosphorylation by a Rho-GTP mechanism," Brain. 2008; 131:90-108.
Pozueta et al., "Caspase-2 is required for dendritic spine and behavioral alterations in J20 APP transgenic mice," Nat Commun. 2013;4:1939.
Raad et al., "Neuroproteomics approach and neurosystems biology analysis: ROCK inhibitors as promising therapeutic targets in neurodegeneration and neurotrauma," Electrophoresis., vol. 33, pp. 3659-3668 (2012).
Ramakers et al., "Dysregulation of Rho GTPases in the αPix/Arhgef6 mouse model of X-linked intellectual disability is paralleled by impaired structural and synaptic plasticity and cognitive deficits," Hum. Mol. Genet. 2012;21:268-86.
Restivo et al., "The Formation of Recent and Remote Memory is Associated with Time-Dependent Formation of Dendritic Spines in the Hippocampus and Anterior Cingulate Cortex," J. Neurosci. 2009;29:8206-14.
Rex et al., "Different Rho GTPase-dependent signaling pathways initiate sequential steps in the consolidation of long-term potentiation," J. Cell Biol. 2009;186:85-97.
Rogers et al., "Clinical trial of indomethacin in Alzheimer's disease," Neurology. vol. 43, pp. 1609-1611 (1993).
Rufer et al., "Adequacy of Maternal Iron Status Protects against Behavioral, Neuroanatomical, and Growth Deficits in Fetal Alcohol Spectrum Disorders," PLoS One, vol. 7, No. 10, e47499, pp. 1-12 (2012).
Sagi et al., "The Non-cyclooxygenase Targets of Non-steroidal Anti-inflammatory Drugs, Lipoxygenases, Peroxisome Proliferator-activated Receptor, Inhibitor of κB Kinase, and NFκB, Do Not Reduce Amyloid β42 production," J. Biol. Chem. 2003;278:31825-30.
Saitoh et al., "ROCK inhibition produces anxiety-related behaviors in mice," Psychopharmacology (Berl.). vol. 188, pp. 1-11 (2006).
Salloum et al., "Rho A and Rac1: Antagonists moving forward," Tissue and Cell, vol. 65, pp. 1-5 (2020).
Saraceno et al., "Altered Expression of Circulating Cdc42 in Frontotemporal Lobar Degeneration," Journal of Alzheimer's Disease, vol. 61, 1477-1483 (2018).
Scheff et al., "Is synaptic loss a unique hallmark of Alzheimer's disease?" Biochem. Pharmacol. 2014;88:517-28.
Schmidt et al., "Gln 63 of Rho is deamidated by Escherichia coli cytotoxic necrotizing factor-1," Nature., vol. 387, pp. 725-729 (1997).
Selkoe, "Alzheimer's disease is a synaptic failure," Science., vol. 298, pp. 789-791 (2002).
Sfakianos et al., "Inhibition of Rho via Arg and p190RhoGAP in the Postnatal Mouse Hippocampus Regulates Dendritic Spine Maturation, Synapse and Dendrite Stability, and Behavior," J. Neurosci. 2007;27:10982-92.
Shen et al., "The presenilin hypothesis of Alzheimer's disease: Evidence for a loss-of-function pathogenic mechanism," PNAS, vol. 104, No. 2, pp. 403-409 (2007).
Sims et al., "Rare coding variants in PLCG2, ABI3 and TREM2 implicate microglial-mediated innate immunity in Alzheimer's disease," Nat. Genet., vol. 49, No. 9, pp. 1373-1384 (2017).
Skelton, "Bilateral cerebellar lesions disrupt conditioned eyelid responses in unrestrained rats," Behav. Neuroscience, vol. 102, No. 4, pp. 586-590 (1988).

(56) References Cited

OTHER PUBLICATIONS

Sonkar et al., "Amyloid β peptide stimulates platelet activation through RhoA-dependent modulation of actomyosin organization," FASEB J., vol. 28, pp. 1819-1829 (2014).
Spillane et al., "Involvement of Rho-family GTPases in axon branching," Small GTPases. 2014;5:e27974.
Stankiewicz et al., "Rho family GTPases: key players in neuronal development, neuronal survival, and neurodegeneration," Front Cell Neurosci. 2014;8:314.
Sterniczuk et al., Characterization of the 3xTg-AD mouse model of Alzheimer's disease: Part 2. Behavioral and cognitive changes, Brain Research, vol. 1348, pp. 149-155 (2010).
Strooper et al., "A presenilin-1-dependent γ-secretase-like protease mediates release of Notch intracellular domain," Nature. 1999;398:518-22.
Tahirovic et al., "Rac1 Regulates Neuronal Polarization through the WAVE Complex," J. Neurosci. 2010;30:6930-43.
Takahashi et al., "Sulindac Sulfide Is a Noncompetitive γ-secretase Inhibitor That Preferentially Reduces Aβ42 Generation," J. Biol. Chem. 2003;278:18664-70.
Tanzi et al., "Twenty Years of the Alzheimer's Disease Amyloid Hypothesis: A Genetic Perspective," Cell. 2005;120:545-55.
Tashiro & Yuste, "Role of Rho GTPases in the morphogenesis and motility of dendritic spines," Meth. Enzymol. vol. 439, pp. 285-302 (2008).
Tashiro et al., "Regulation of Dendritic Spine Morphology by the Rho Family of Small GTPases: Antagonistic Roles of Rac and Rho," Cerebral Cortex, vol. 10, pp. 927-938 (2000).
Terry et al., "Physical basis of cognitive alterations in Alzheimer's disease: synapse loss is the major correlate of cognitive impairment," Ann. Neurol., vol. 30, pp. 572-580 (1991).
Terry, "A Long Line of Alzheimer's Failures: Roche Drops Two Drug Trials," BioSpace, pp. 1-3, https://www.biospace.com/article/a-long-line-of-failures-roche-drops-alzheimer-s-drug-trials/ (retrieved from the internet Feb. 26, 2020) (Year: 2019).
Thomas & Tran, "Choline Supplementation Mitigates Trace, but not Delay, Eyeblink Conditioning Deficits in Rats Exposed to Alcohol During Development," Hippocampus, vol. 22, pp. 619-630 (2012).
Tran et al., Binge-Like Ethanol Exposure During the Early Postnatal Period Impairs Eyeblink Conditioning at Short and Long CS-US Intervals in Rats, Dev. Psychibiol., vol. 49, pp. 589-605 (2007).
Tsyba et al., "Intersectin multidomain adaptor proteins: regulation of functional diversity," Gene., vol. 473, pp. 67-75 (2011).
Uddin et al., "Multi-Target Drug Candidates for Multifactorial Alzheimer's Disease: AChE and NMDAR as Molecular Targets," Molecular Neurobiology, vol. 58, pp. 281-303 (2021).
Van Aelst & Cline, "Rho GTPases and activity-dependent dendrite development," Curr. Opin. Neurobiol. vol. 14, pp. 297-304 (2004).
Wang et al., "Rac1 inhibition negatively regulates transcriptional activity of the amyloid precursor protein gene," J. Neurosci. Res., vol. 87, pp. 2105-2114 (2009).
Webster et al., "Using mice to model Alzheimer's dementia: an overview of the clinical disease and the preclinical behavioral changes in 10 mouse models," Frontiers in Genetics, vol. 5 pp. 1-23 (2014).
Weggen et al., "A subset of NSAIDs lower amyloidogenic Abeta42 independently of cyclooxygenase activity," Nature., vol. 414, pp. 212-216 (2001).
Weggen et al., "Aβ42-lowering Nonsteroidal Anti-inflammatory Drugs Preserve Intramembrane Cleavage of the Amyloid Precursor Protein (APP) and ErbB-4 Receptor and Signaling through the APP Intracellular Domain," J. Biol. Chem. 2003;278:30748-54.
Williamson et al., "Rapid Tyrosine Phosphorylation of Neuronal Proteins Including Tau and Focal Adhesion Kinase in Response to Amyloid-β Peptide Exposure: Involvement of Src Family Protein Kinases," J. Neurosci. 2002;22:10-20.
Wilmot et al., "Translational gene mapping of cognitive decline," Neurobiol. Aging. 2008;29:524-41.
Wong et al., "Intersectin (ITSN) Family of Scaffolds Function as Molecular Hubs in Protein Interaction Networks," PLoS One, vol. 7, Iss. 4, e36023, pp. 1-9 (2012).
Wu et al., "Ack1 is a dopamine transporter endocytic brake thatrescues a trafficking-dysregulated ADHDcoding variant," Proc. Natl. Acad. Sci., USA, vol. 112, No. 50, pp. 15480-15485 (2015).
Wu et al., "Inhibition of Rac1-dependent forgetting alleviates memory deficits in animal models of Alzheimer's disease," Protein & Cell, vol. 10, No. 10, pp. 745-759 (2019).
Yankner et al., "Amyloid β-Protein Toxicity and the Pathogenesis of Alzheimer Disease," Journal of Biological Chemistry, vol. 284, No. 8, pp. 4755-4759 (2009).
Yankner et al., "Neurotrophic and neurotoxic effects of amyloid beta protein: reversal by tachykinin neuropeptides," Science, vol. 250, Issue 4978, pp. 279-282 (1990).
Yarza et al., "c-Jun N-terminal Kinase (JNK) Signaling as a Therapeutic Target for Alzheimer's Disease," Front Pharmacol. 2015;6:321.
Zhao et al., "Role of p21-activated kinase pathway defects in the cognitive deficits of Alzheimer disease," Nat. Neurosci., vol. 9, pp. 234-242 (2006).
Zhao et al., "Targeting protein-protein interactions in Rho GTPase regulation using small molecules," Science Supplement, pp. 71-72 (2016).
Zhou et al., "Nonsteroidal anti-inflammatory drugs can lower amyloidogenic Abeta42 by inhibiting Rho," Science., vol. 302, pp. 1215-1217 (2003).
Zhu et al., "Activation of oncogenic pathways in degenerating neurons in Alzheimer disease," Int. J. Dev. Neurosci., vol. 18, pp. 433-437 (2000).
Zhu et al., "Differential activation of neuronal ERK, JNK/SAPK and p38 in Alzheimer disease: the "two hit" hypothesis," Mech. Ageing Dev., vol. 123:39-46 (2001).
Zins et al., "A Rac1/Cdc42 GTPase-Specific Small Molecule Inhibitor Suppresses Growth of Primary Human Prostate Cancer Xenografts and Prolongs Survival in Mice," PLoS ONE. 2013;8:e74924.

\* cited by examiner

ROLES OF MODULATORS OF INTERSECTIN-CDC42 SIGNALING IN ALZHEIMER'S DISEASE

RELATED APPLICATIONS

This application is a divisional of U.S. patent application Ser. No. 16/141,849, filed Sep. 25, 2018, which is based on and claims the benefit of U.S. Provisional Patent Application Ser. No. 62/562,816, filed Sep. 25, 2017, the disclosures of which are incorporated herein by reference in their entireties.

GOVERNMENT INTEREST

This invention was made with government support under Grant Nos. CA111891, CA165202, and CA165202S awarded by the National Institutes of Health. The government has certain rights in the invention.

TECHNICAL FIELD

The presently disclosed subject matter relates to methods of treating Alzheimer's disease through the administration of compounds that modulate Cdc42 activity, for example, intersectin-Cdc42 signaling. Exemplary compounds that modulate Cdc42 include sulfonamides of thioureas and analogs of thioureas, such as carbamates and ureas; disulfonamides of dibenzofuran and related fused aromatic compounds; and acyl hydrazones.

ABBREVIATIONS

%=percent or percentage
° C.=degrees Celsius
μg=microgram
μL=microliter
μM=micromolar
Aβ=β-amyloid
AD=Alzheimer's disease
ADL=activities of daily living
BSA=bovine serum albumin
Cdc42=cell division control protein 42 homolog
DMSO=dimethyl sulfoxide
DS=Down's syndrome
GEF=guanine nucleotide dissociation factor
GTP=guanosine triphosphate
h=hour
HD=Huntington's disease
ICM=50 percent inhibitory concentration
ITSN=intersectin
mant-GTP=2'/3'-O—(N-methyl-anthraniloyl)-guanosine-5'-triphosphate
MAPK=mitogen-activated protein kinase
min=minutes
mL=milliliter
mm=millimeter
mmol=millimole
ng=nanogram
nm=nanometer
RhoA=Ras homolog gene family, member A
Rac1=Ras-Related C3 Botulinum Toxin Substrate 1
RT=room temperature
s=seconds
sem=standard error of the mean
WT=wild-type

BACKGROUND

Alzheimer's disease (AD) is a neurodegenerative disorder usually associated with old age that affects memory and other cognitive functions and is the most common cause of dementia. Data from the Alzheimer's Disease Association indicates that 5.7 million people in the United States currently have AD and that by the year 2050, that number is expected to rise to 17 million people. Alzheimer's disease is usually diagnosed based on a person's medical history, family medical history, and behavioral observations. The presence of characteristic neurological and neuropsychological features and the absence of alternative conditions are supportive in diagnosis. Advanced medical imaging with computed tomography (CT) or magnetic resonance imaging (MRI), and with single-photon emission computed tomography (SPECT) or positron emission tomography (PET) can be used to help exclude other cerebral pathology or subtypes of dementia.

Current treatments for AD focus include medications that focus on treating cognitive symptoms. These medications include cholinesterase inhibitors, such as donepezil, galantamine, and rivastigmine, and glutamate receptor antagonist Memantine (Namenda). However, with the growing number of people living to older ages, there is an urgency to gain a better understanding of elements of the pathogenic pathway of AD, to discover new agents that target these elements, and to establish their roles in the treatment and prevention of AD.

SUMMARY

In some embodiments, the presently disclosed subject matter provides a method of treating Alzheimer's disease in a subject in need of treatment thereof, wherein the method comprises administering to the subject a modulator compound, wherein the modulator compound inhibits or activates cell division control protein 42 (Cdc42). In some embodiments, said modulator compound has a structure of one of Formulas (I), (II), and (III):

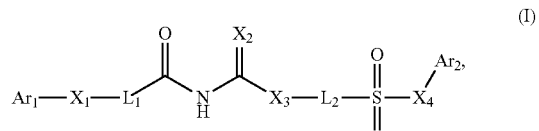

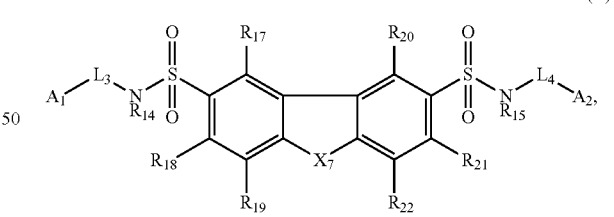

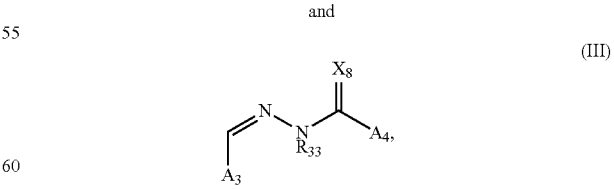

wherein: $Ar_1$ and $Ar_2$ are independently selected from the group comprising aryl, heteroaryl, substituted aryl, and substituted heteroaryl; $A_1$ and $A_2$ are independently selected from the group comprising alkyl, substituted alkyl, cycloalkyl, substituted cycloalkyl, heterocycle, substituted heterocycle, aryl, substituted aryl, heteroaryl, and substituted heteroaryl; $A_3$ is selected from the group comprising cycloalkyl, substituted cycloalkyl, heterocycle, substituted heterocycle, aryl, substituted aryl, heteroaryl, and substituted heteroaryl; $A_4$ is selected from the group comprising alkoxy, aralkoxy, aryloxy, amino, cycloalkyl, substituted cycloalkyl, heterocycle, substituted heterocycle, aryl, substituted aryl, heteroaryl, and substituted heteroaryl; $X_1$ is selected from the group comprising —CH—, —S—, NR, and —O—, wherein R is selected from H, alkyl, and substituted alkyl; $X_2$ is O or S; $X_3$ is selected from —$NR_{12}$— and —O—, wherein $R_{12}$ is selected from H, alkyl, and substituted alkyl; $X_4$ is selected from $NR_{13}$ and —O—, wherein $R_{13}$ is selected from H, alkyl, and substituted alkyl; $X_7$ is selected from —$CH_2$—, —NH—, —O—, and —S—; $X_8$ is selected from O, S, and $CH_2$; $L_1$ and $L_2$ are independently selected from the group comprising alkylene, cycloalkylene, aralkylene, and arylene; $L_3$ and $L_4$ are each independently present or absent, and, if present are independently a —$(CH_2)_n$— group, wherein n is an integer between 1 and 10; $R_{14}$ and $R_{15}$ are independently selected from H, alkyl, and substituted alkyl; $R_{17}$, $R_{18}$, $R_{19}$, $R_{20}$, $R_{21}$, and $R_{22}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and $R_{33}$ is selected from H, alkyl, and substituted alkyl; or a pharmaceutically acceptable salt thereof.

In some embodiments, the modulator compound is a compound of Formula (I):

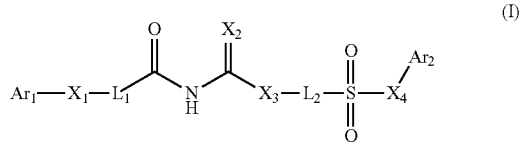

(I)

wherein: $Ar_1$ and $Ar_2$ are independently selected from the group comprising aryl, heteroaryl, substituted aryl, and substituted heteroaryl; $X_1$ is selected from the group comprising —CH—, —S—, NR, and —O—, wherein R is selected from H, alkyl, and substituted alkyl; $L_1$ and $L_2$ are independently selected from the group comprising alkylene, cycloalkylene, aralkylene, and arylene; $X_2$ is O or S; $X_3$ is selected from —$NR_{12}$— and —O—, wherein $R_{12}$ is selected from H, alkyl, and substituted alkyl; and $X_4$ is selected from $NR_{13}$ and —O—, wherein $R_{13}$ is selected from H, alkyl, and substituted alkyl; or a pharmaceutically acceptable salt thereof. In some embodiments, one of $Ar_1$ and $Ar_2$ is heteroaryl or substituted heteroaryl.

In some embodiments, the compound of Formula (I) has a structure of Formula (Ia):

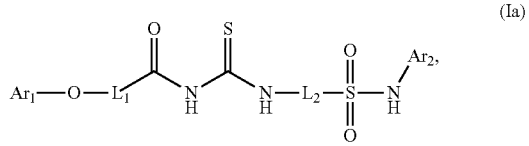

(Ia)

wherein: $Ar_1$ and $Ar_2$ are independently selected from aryl, substituted aryl, heteroaryl, and substituted aryl; and $L_1$ and $L_2$ are independently selected from the group comprising alkylene, cycloalkylene, aralkylene, and arylene; or a pharmaceutically acceptable salt thereof. In some embodiments, the compound of Formula (Ia) has a structure of Formula (Ib):

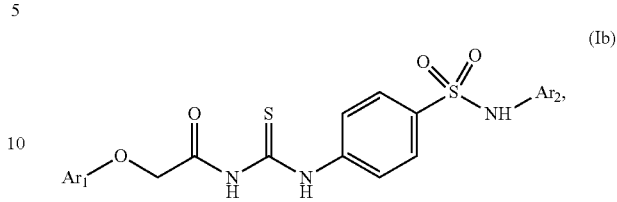

(Ib)

wherein: $Ar_1$ and $Ar_2$ are independently selected from aryl, substituted aryl, heteroaryl, and substituted heteroaryl; or a pharmaceutically acceptable salt thereof.

In some embodiments, the compound of Formula (I) has a structure of Formula (Ic):

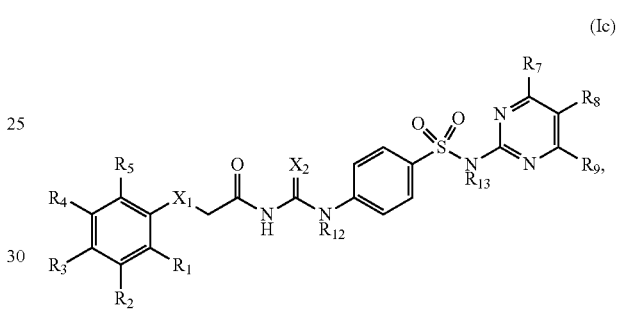

(Ic)

wherein: each of $R_1$-$R_5$ and $R_7$-$R_9$ is independently selected from the group comprising H, halo, nitro, cyano, hydroxyl, carboxyl, acyl, alkyl, substituted alkyl, alkoxyl, aralkoxyl, aryloxyl, amino, and sulfonyl; $X_1$ is selected from —CH—, —S—, NR, and —O—, wherein R is selected from H, alkyl, and substituted alkyl; $X_2$ is selected from O and S; $R_{12}$ is selected from H, alkyl, and substituted alkyl; and $R_{13}$ is selected from H, alkyl, and substituted alkyl; or a pharmaceutically acceptable salt thereof. In some embodiments, the compound of Formula (Ic) has a structure of Formula (Id):

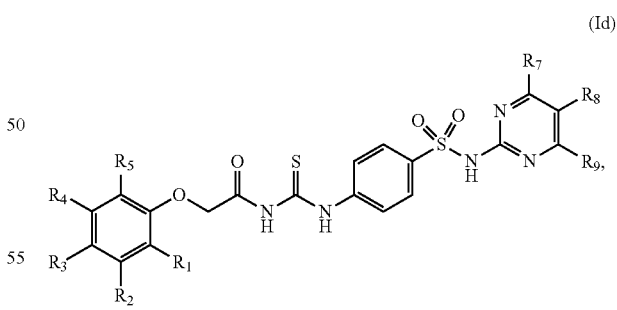

(Id)

wherein: each of $R_1$-$R_5$ and $R_7$-$R_9$ is independently selected from the group comprising H, halo, nitro, cyano, hydroxyl, carboxyl, acyl, alkyl, substituted alkyl, alkoxyl, aralkoxyl, aryloxyl, amino, and sulfonyl; or a pharmaceutically acceptable salt thereof.

In some embodiments, $R_2$ and $R_4$ are each H and each of $R_1$, $R_3$, and $R_5$ are independently selected from H, halo, alkyl and alkoxy. In some embodiments, one or two of $R_1$, $R_3$, and $R_5$ are selected from halo, alkyl, and alkoxy. In some embodiments, $R_3$ is halo, alkyl, or alkoxy. In some embodiments, each of $R_7$-$R_9$ is selected from H and alkyl.

In some embodiments, the compound of Formula (Id) is selected from the group consisting of:

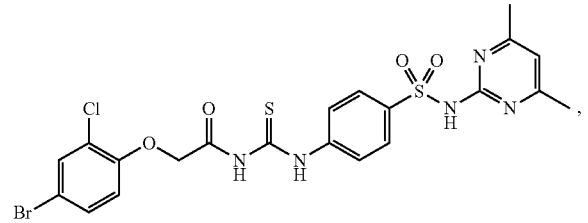 [SMILES: Cc1cc(C)nc(NS(=O)(=O)c2ccc(NC(=S)NC(=O)COc3ccc(Br)cc3Cl)cc2)n1],

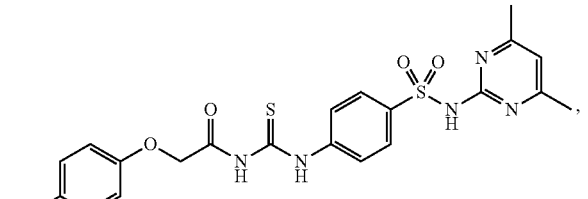,

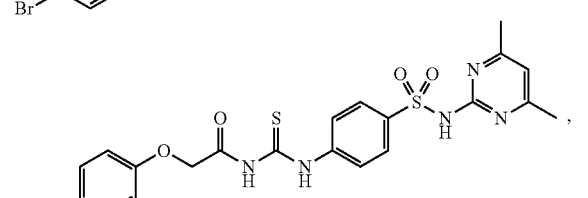,

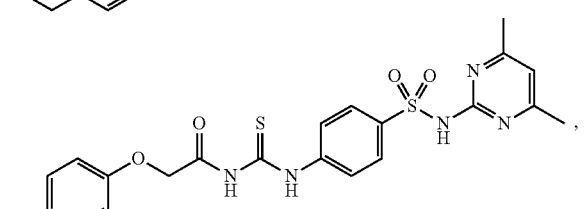,

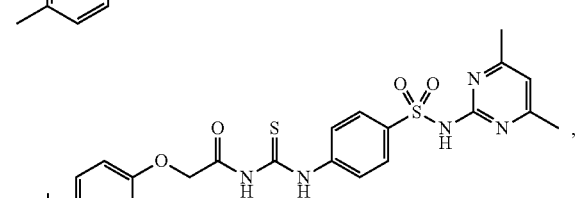,

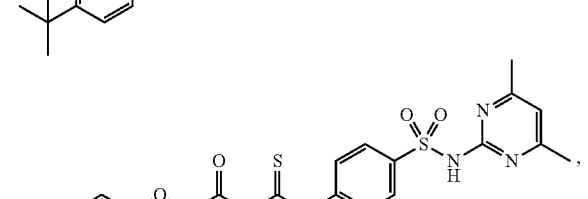, and

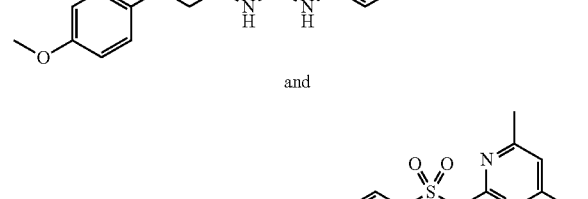;

or a pharmaceutically acceptable salt thereof. In some embodiments, the compound is:

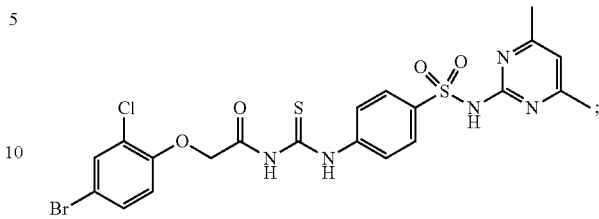;

or a pharmaceutically acceptable salt thereof.

In some embodiments, the modulator compound is a compound of Formula (II):

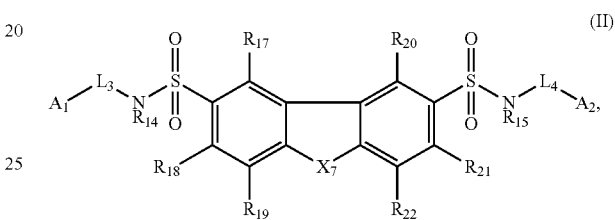

wherein: $A_1$ and $A_2$ are independently selected from the group comprising alkyl, substituted alkyl, cycloalkyl, substituted cycloalkyl, heterocycle, substituted heterocycle, aryl, substituted aryl, heteroaryl, and substituted heteroaryl; $L_3$ and $L_4$ are each independently present or absent, and, if present are independently a —(CH$_2$)$_n$— group, wherein n is an integer between 1 and 10; $R_{14}$ and $R_{15}$ are independently selected from H, alkyl, and substituted alkyl; $R_{17}$, $R_{18}$, $R_{19}$, $R_{20}$, $R_{21}$, and $R_{22}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and $X_7$ is selected from —CH$_2$—, —NH—, —O—, and —S—; or a pharmaceutically acceptable salt thereof. In some embodiments, $A_1$ and $A_2$ are independently selected from the group comprising methyl, substituted or unsubstituted cyclohexyl, substituted or unsubstituted phenyl, substituted or unsubstituted pyridinyl, substituted or unsubstituted tetrahydrofuranyl, substituted or unsubstituted tetrahydrothiophenyl, substituted or unsubstituted pyrrolidinyl, substituted or unsubstituted tetrahydropyranyl, substituted or unsubstituted tetrahydrothiopyranyl, and substituted or unsubstituted piperidinyl.

In some embodiments, $A_1$ is phenyl or substituted phenyl and $L_3$ is absent and the compound of Formula (II) has a structure of Formula (IIa):

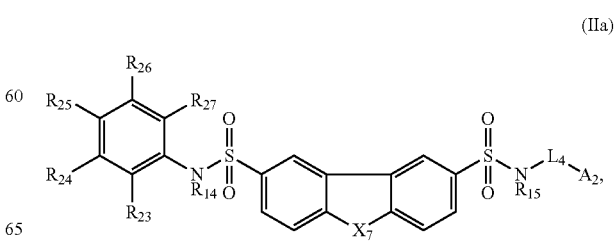

wherein: $A_2$ is selected from the group comprising alkyl, substituted alkyl, cycloalkyl, substituted cycloalkyl, heterocycle, substituted heterocycle, aryl, substituted aryl, heteroaryl, and substituted heteroaryl; $L_4$ is present or absent, and, if present is $—(CH_2)_n—$, wherein n is an integer between 1 and 10; $R_{14}$ and $R_{15}$ are independently selected from H, alkyl, and substituted alkyl; $R_{23}$, $R_{24}$, $R_{25}$, $R_{26}$, and $R_{27}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and $X_7$ is selected from $—CH_2—$, $—NH—$, $—O—$, and $—S—$; or a pharmaceutically acceptable salt thereof.

In some embodiments, the compound of Formula (II) has a structure of Formula (IIb):

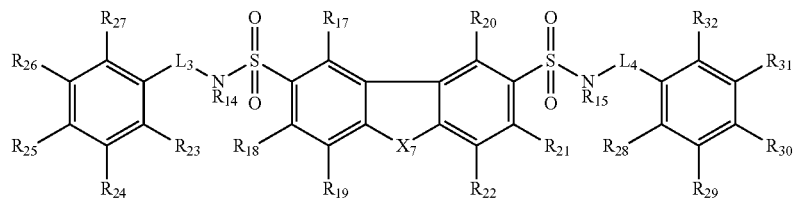

wherein: $L_3$ and $L_4$ are independently present or absent, and, if present are independently $—(CH_2)_n—$, wherein n is an integer between 1 and 10; $R_{14}$ and $R_{15}$ are independently selected from H, alkyl, and substituted alkyl; $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, and $R_{32}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and $X_7$ is selected from $—CH_2—$, $—NH—$, $—O—$, and $—S—$; or a pharmaceutically acceptable salt thereof.

In some embodiments, $L_3$ and $L_4$ are each absent and $R_{17}$, $R_{18}$, $R_{19}$, $R_{20}$, $R_{21}$, and $R_{22}$ are each H, and the compound of Formula (IIb) has a structure of Formula (IIc):

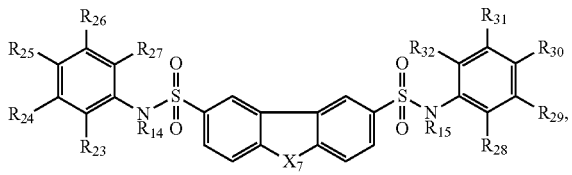

wherein: $R_{14}$ and $R_{15}$ are independently selected from H, alkyl, and substituted alkyl; $R_{23}$, $R_{24}$, $R_{25}$, $R_{26}$, $R_{27}$, $R_{28}$, $R_{29}$, $R_{30}$, $R_{31}$, and $R_{32}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and $X_7$ is selected from $—CH_2—$, $—NH—$, $—O—$, and $—S—$; or a pharmaceutically acceptable salt thereof. In some embodiments, $R_{23}$ is hydroxyl. In some embodiments, $R_{28}$ is OH. In some embodiments, $X_7$ is $—O—$.

In some embodiments, the compound of Formula (II) is the compound having the structure:

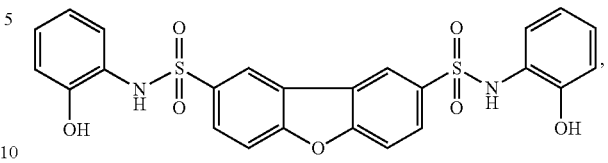

or a pharmaceutically acceptable salt thereof.

In some embodiments, the modulator compound has a structure of Formula (III):

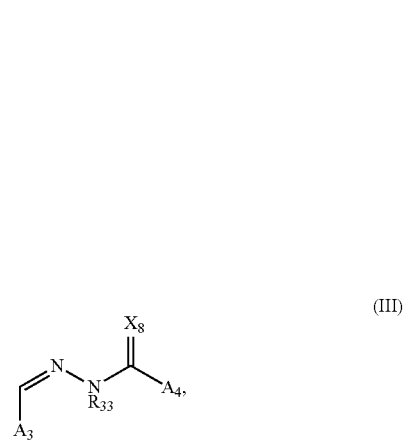

wherein: $A_3$ is selected from the group comprising cycloalkyl, substituted cycloalkyl, heterocycle, substituted heterocycle, aryl, substituted aryl, heteroaryl, and substituted heteroaryl; $A_4$ is selected from the group comprising alkoxy, aralkoxy, aryloxy, amino, cycloalkyl, substituted cycloalkyl, heterocycle, substituted heterocycle, aryl, substituted aryl, heteroaryl, and substituted heteroaryl; $R_{33}$ is selected from H, alkyl, and substituted alkyl; and $X_8$ is selected from O, S, and $CH_2$; or a pharmaceutically acceptable salt thereof.

In some embodiments, the compound of Formula (III) has a structure of Formula (IIIa):

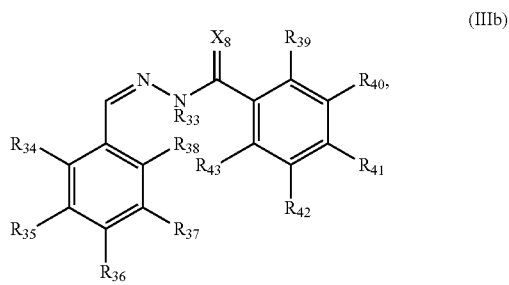

wherein: $X_8$ is selected from O and $CH_2$; $R_{33}$ is selected from H, alkyl, and substituted alkyl; and each of $R_{34}$, $R_{35}$, $R_{36}$, $R_{37}$, $R_{39}$, $R_{40}$, $R_{41}$, $R_{42}$, and $R_{43}$ are independently selected from the group comprising H, halo, nitro, cyano, hydroxyl, carboxyl, acyl, alkyl, substituted alkyl, alkoxyl, aralkoxyl, aryloxyl, amino, and sulfonyl; or a pharmaceutically acceptable salt thereof.

In some embodiments, $X_8$ is O. In some embodiments, $R_{34}$ is OH. In some embodiments, one or both of $R_{40}$ and $R_{42}$ are OH. In some embodiments, the compound of Formula (III) is:

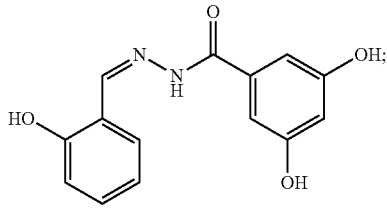 [SMILES: O=C(N/N=C\c1ccccc1O)c1cc(O)cc(O)c1]

or a pharmaceutically acceptable salt thereof.

In some embodiments, the presently disclosed subject matter provides a method of treating a neurodegenerative, neurocognitive, and/or neurodevelopmental disease and/or disorder in a subject in need of treatment thereof, wherein the method comprises administering to the subject a modulator compound, wherein the modulator compound inhibits or activates cell division control protein 42 (Cdc42), wherein said modulator compound has a structure of one of Formulas (II) and (III):

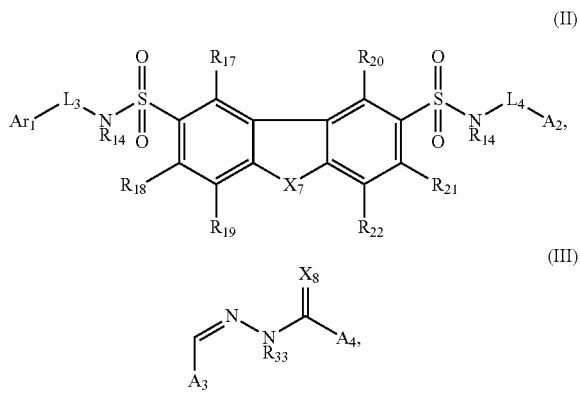

wherein: $A_1$ and $A_2$ are independently selected from the group comprising alkyl, substituted alkyl, cycloalkyl, substituted cycloalkyl, heterocycle, substituted heterocycle, aryl, substituted aryl, heteroaryl, and substituted heteroaryl; $A_3$ is selected from the group comprising cycloalkyl, substituted cycloalkyl, heterocycle, substituted heterocycle, aryl, substituted aryl, heteroaryl, and substituted heteroaryl; $A_4$ is selected from the group comprising alkoxy, aralkoxy, aryloxy, amino, cycloalkyl, substituted cycloalkyl, heterocycle, substituted heterocycle, aryl, substituted aryl, heteroaryl, and substituted heteroaryl; $X_7$ is selected from —$CH_2$—, —NH—, —O—, and —S—; $X_8$ is selected from O, S, and $CH_2$; $L_3$ and $L_4$ are each independently present or absent, and, if present are independently a —$(CH_2)_n$— group, wherein n is an integer between 1 and 10; $R_{14}$ and $R_{15}$ are independently selected from H, alkyl, and substituted alkyl; $R_{17}$, $R_{18}$, $R_{19}$, $R_{20}$, $R_{21}$, and $R_{22}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and $R_{33}$ is selected from H, alkyl, and substituted alkyl; or a pharmaceutically acceptable salt thereof.

In some embodiments, the modulator compound is a compound of Formula (II):

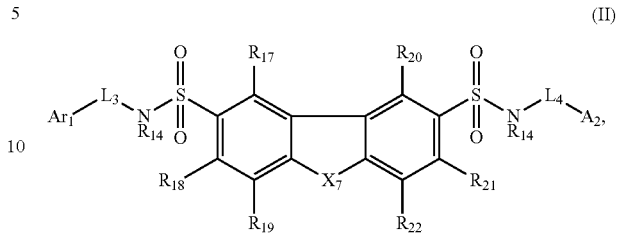

wherein: $A_1$ and $A_2$ are independently selected from the group comprising alkyl, substituted alkyl, cycloalkyl, substituted cycloalkyl, heterocycle, substituted heterocycle, aryl, substituted aryl, heteroaryl, and substituted heteroaryl; $L_3$ and $L_4$ are each independently present or absent, and, if present are independently a —$(CH_2)_n$— group, wherein n is an integer between 1 and 10; $R_{14}$ and $R_{15}$ are independently selected from H, alkyl, and substituted alkyl; $R_{17}$, $R_{18}$, $R_{19}$, $R_{20}$, $R_{21}$, and $R_{22}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and $X_7$ is selected from —$CH_2$—, —NH—, —O—, and —S—; or a pharmaceutically acceptable salt thereof.

In some embodiments, the modulator compound has a structure of Formula (III):

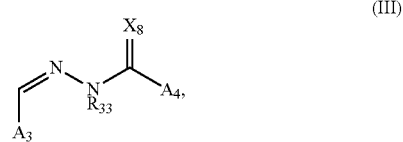

wherein: $A_3$ is selected from the group comprising cycloalkyl, substituted cycloalkyl, heterocycle, substituted heterocycle, aryl, substituted aryl, heteroaryl, and substituted heteroaryl; $A_4$ is selected from the group comprising alkoxy, aralkoxy, aryloxy, amino, cycloalkyl, substituted cycloalkyl, heterocycle, substituted heterocycle, aryl, substituted aryl, heteroaryl, and substituted heteroaryl; $R_{33}$ is selected from H, alkyl, and substituted alkyl; and $X_8$ is selected from O, S, and $CH_2$; or a pharmaceutically acceptable salt thereof.

Accordingly, it is an object of the presently disclosed subject matter to provide methods of treating Alzheimer's disease and other neurodegenerative, neurocognitive, and/or neurodevelopmental diseases and/or disorders.

An object of the presently disclosed subject matter having been stated hereinabove, and which is achieved in whole or in part by the presently disclosed subject matter, other objects will become evident as the description proceeds hereinbelow.

DETAILED DESCRIPTION

Figure 1B:
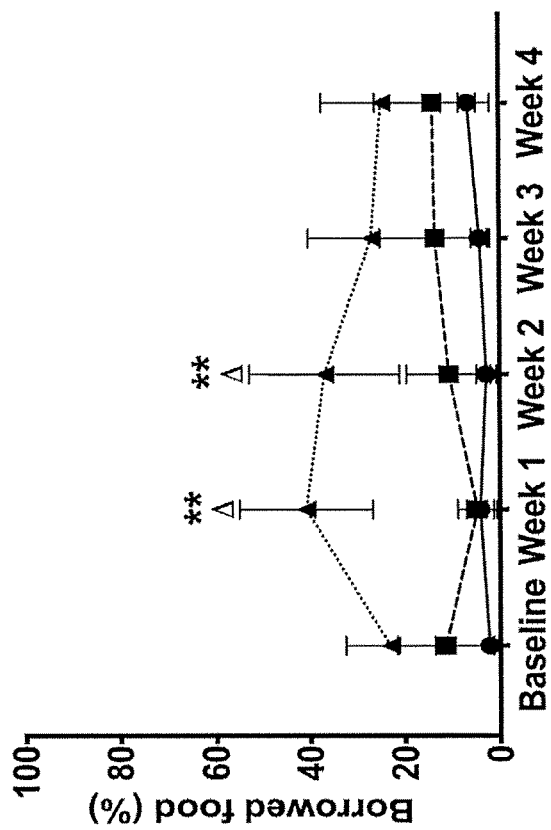
FIG. 1B is a graph showing the effects of the administration of exemplary cell division control protein 42 homolog (Cdc42) modulator compounds, ZCL278 (squares) or ZCL279 (triangles), on food burrowing behavior (measured as a percentage (%) of food burrowed outside a burrowing tube filled with 200 grams of food pellets) in triple transgenic mice of a mouse model of Alzheimer's disease (3×Tg-AD). Behavior was followed over the course of 4 weeks. For comparison, data from mice treated with vehicle (sesame oil with 5% dimethyl sulfoxide (DMSO)) is shown as a control (circles). "Baseline" on the x-axis refers to baseline behavior (i.e., prior to compound administration). N=10 group. Values represent mean±sem. **$p<0.001$, relative to control. $\Delta p<0.05$, relative to ACL278.

The presently disclosed subject matter will now be described more fully hereinafter with reference to the accompanying Examples and Figures, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

All publications, patent applications, patents, and other references mentioned herein are incorporated by reference in their entirety.

I. Definitions

While the following terms are believed to be well understood by one of ordinary skill in the art, the following definitions are set forth to facilitate explanation of the presently disclosed subject matter.

Unless otherwise defined, all technical and scientific terms used herein have the same meaning as commonly understood by one of ordinary skill in the art to which this presently described subject matter belongs.

Following long-standing patent law convention, the terms "a", "an", and "the" refer to "one or more" when used in this application, including the claims. Thus, for example, reference to "a compound" or "a symptom" includes a plurality of such compounds or symptoms, and so forth.

Unless otherwise indicated, all numbers expressing quantities of time, weight, concentration, volume, density, percentage, temperature, dosage, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a weight, concentration, density, dosage, temperature, volume, percentage, time, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed devices or systems.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

As used herein the term "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-6}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

Alkyl groups can optionally be substituted (a "substituted alkyl") with one or more alkyl group substituents, which can be the same or different. The term "alkyl group substituent" includes but is not limited to alkyl (saturated or unsaturated), substituted alkyl (e.g., halo-substituted and perhalo-substituted alkyl, such as but not limited to, —$CF_3$), cycloalkyl, halo, nitro, hydroxyl, carbonyl, carboxyl, acyl, oxo (=O), alkoxyl, aryloxyl, aralkoxyl, thioalkyl, thioaryl, thioaralkyl, amino (e.g., aminoalkyl, aminodialkyl, aminoaryl, etc.), sulfonyl, and sulfinyl.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Thus, examples of aryl include, but are not limited to, phenyl, naphthyl, biphenyl, and diphenylether, among others. Aryl groups include heteroaryl groups, wherein the aromatic ring or rings include one or more heteroatom (e.g., N, O, S, or Se) in place of one or more carbon atoms. Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, and thiophenyl.

The aryl group can be optionally substituted (a "substituted aryl") with one or more aryl group substituents, which can be the same or different, wherein "aryl group substituent" includes alkyl (saturated or unsaturated), substituted alkyl (e.g., haloalkyl and perhaloalkyl, such as but not limited to —$CF_3$), cycloalkyl, aryl, substituted aryl, aralkyl, halo, nitro, hydroxyl, acyl, carboxyl, alkoxyl, aryloxyl, aralkyloxyl, thioalkyl, thioaryl, thioaralkyl, amino (e.g., aminoalkyl, aminodialkyl, aminoaryl, etc.), sulfonyl, and sulfinyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group.

As used herein, the term "acyl" refers to an organic carboxylic acid group wherein the —OH of the carboxylic acid group has been replaced with another substituent. Thus, an acyl group can be represented by RC(═O)—, wherein R is an alkyl, substituted alkyl, aralkyl, substituted aralkyl, aryl or substituted aryl group as defined herein. As such, the term "acyl" specifically includes arylacyl groups, such as a phenacyl group. Specific examples of acyl groups include acetyl and benzoyl.

"Cyclic" and "cycloalkyl" refer to a non-aromatic mono- or multi-cyclic ring system of about 3 to about 10 carbon atoms, e.g., 3, 4, 5, 6, 7, 8, 9, or 10 carbon atoms. The cycloalkyl group can be saturated or partially unsaturated. The cycloalkyl group also can be optionally substituted with an alkyl group substituent as defined herein. There can be optionally inserted along the cyclic alkyl chain one or more oxygen. Representative monocyclic cycloalkyl rings include cyclopentyl, cyclohexyl, and cycloheptyl. Multicyclic cycloalkyl rings include adamantyl, octahydronaphthyl, decalin, camphane, and noradamantyl.

"Alkoxyl" and "alkoxy" refer to an alkyl-O— group wherein alkyl is as previously described, including substituted alkyl. The term "alkoxyl" as used herein can refer to, for example, methoxyl, ethoxyl, propoxyl, isopropoxyl, butoxyl, t-butoxyl, and pentoxyl. The term "oxyalkyl" can be used interchangeably with "alkoxyl".

"Aryloxyl" and "aryloxy" refer to an aryl-O— group wherein the aryl group is as previously described, including a substituted aryl. The term "aryloxyl" as used herein can refer to phenyloxyl or naphthyloxyl, and to alkyl, substituted alkyl, or alkoxyl substituted phenyloxyl or naphthyloxyl.

"Aralkyl" refers to an aryl-alkyl- or an -alkyl-aryl group wherein aryl and alkyl are as previously described, and can include substituted aryl and substituted alkyl. Thus, "substituted aralkyl" can refer to an aralkyl group comprising one or more alkyl or aryl group substituents. Exemplary aralkyl groups include benzyl, phenylethyl, and naphthylmethyl.

"Aralkyloxyl," "aralkoxyl" and "aralkoxy" refer to an aralkyl-O— group wherein the aralkyl group is as previously described. An exemplary aralkyloxyl group is benzyloxyl. "Substituted aralkyoxyl" can refer to an aralkoxyl group wherein the alkyl and/or aryl portion of the aralkyl are substituted by one or more alkyl or aryl group substituents.

The terms "hydroxyl" and "hydroxyl" refer to the group —OH.

The term "thio" and "thiol" refer to the group —SH.

The term "carbonyl" refers to the group —C(═O)—. The term "carbonyl carbon" refers to a carbon atom of a carbonyl group. Other groups such as, but not limited to, acyl groups, anhydrides, aldehydes, esters, lactones, amides, ketones, carbonates, and carboxylic acids, include a carbonyl group.

The term "thiocarbonyl" refers to the group —C(═S)—.

The term "carboxyl" refers to the —C(═O)OH or —C(═O)O⁻ group. The term carboxylic acid" can also be used to refer to the group —C(═O)OH or to a compound containing such a group.

The term "acid chloride" refers to the group —C(═O)—Cl or to a compound containing such a group.

The term "aldehyde" can refer to the —C(═O)H group or to a compound containing such a group.

The terms "halo", "halide", or "halogen" as used herein refer to fluoro (F), chloro (Cl), bromo (Br), and iodo (I) groups.

The term "amine" refers to a molecule having the formula $N(R)_3$, or a protonated form thereof, wherein each R is independently H, alkyl, substituted alkyl, aryl, substituted aryl, aralkyl, substituted aralkyl, or wherein two R groups together form an alkylene or arylene group. The term "primary amine" refers to an amine wherein at least two R groups are H. The term "secondary amine" refers to an amine wherein only one R group is H. The term "alkylamine" can refer to an amine wherein two R groups are H and the other R group is alkyl or substituted alkyl. "Dialkylamine" can refer to an amine where two R groups are alkyl. "Arylamine" can refer to an amine wherein one R group is aryl. Amines can also be protonated, i.e., have the formula $[NH(R)_3]^+$.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl.

The term "sulfonyl" refers to the —$S(═O)_2R$ group, wherein R is alkyl, substituted alkyl, aralkyl, substituted aralkyl, aryl, or substituted aryl.

The term "sulfinyl" refers to the —S(═O)R group, wherein R is alkyl, substituted alkyl, aralkyl, substituted aralkyl, aryl, or substituted aryl.

The term "ester" as used herein refers to a compound that comprises the group R'—O—C(═O)—R, wherein R and R' are independently alkyl, cycloalkyl, aralkyl, or aryl, wherein the alkyl, cycloalkyl, aralkyl, or aryl are optionally substituted. The term "esterifying" can refer to forming an ester by contacting a compound containing a carboxylic acid or derivative thereof (e.g., an acid chloride) and a compound containing a hydroxyl group (e.g., an alcohol or a phenol).

The term "urea" as used herein refers to a compound containing the group —$(R)_2N$—C(═O)—$N(R)_2$, wherein each R is independently selected from H, alkyl, substituted alkyl, aralkyl, substituted aralkyl, aryl, and substituted aryl.

The term "thiourea" as used herein refers to a compound that comprises the group —$(R)_2N$—C(═S)—$N(R)_2$, wherein each R is independently selected from H, alkyl, substituted alkyl, aralkyl, substituted aralkyl, aryl, and substituted aryl.

The term "carbamate" as used herein refers to a compound containing the group —(R)$_2$N—C(=O)—OR, wherein each R is independently selected from H, alkyl, substituted alkyl, aralkyl, substituted aralkyl, aryl, and substituted aryl.

The term "thiocarbamate" as used herein refers to a carbamate wherein the carbonyl group is replaced by a thiocarbonyl group.

The term "hydrazine" as used herein refers to a compound containing the group (R)$_2$N—N(R)$_2$, wherein each R is independently selected from the group comprising H, alkyl, substituted alkyl, aralkyl, substituted aralkyl, aryl, and substituted aryl.

The term "hydrazone" as used herein refers to a compound containing the group (R)$_2$C=N—N(R)$_2$, wherein each R is independently selected from the group comprising H, alkyl, substituted alkyl, aralkyl, substituted aralkyl, aryl, and substituted aryl.

The term "sulfonamide" as used herein refers to a compound comprising the group —S(=O)$_2$—N(R)$_2$, wherein each R is independently selected from the group comprising H, alkyl, substituted alkyl, aralkyl, substituted aralkyl, aryl, and substituted aryl.

A solid line crossed by a wavy line, e.g., in the structure:

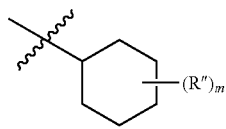

indicates the site where a substituent can bond to another group.

A structure represented generally by a formula such as:

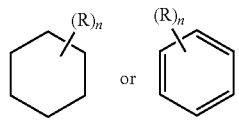

as used herein refers to a ring structure, for example, but not limited to a 5-carbon or a 6-carbon aliphatic and/or aromatic cyclic compound (or a heterocyclic or heteroaromatic analog thereof) comprising a substituent R group, wherein the R group can be present or absent, and when present, one or more R groups can each be substituted on one or more available carbon atoms of the ring structure, replacing an H atom that would be bonded to that carbon in the absence of the R group. The presence or absence of the R group and the number of R groups is determined by the value of the integer n. Each R group, if more than one, is substituted on an available carbon of the ring structure rather than on another R group. For example, the structure:

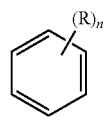

wherein n is an integer from 0 to 2 comprises compound groups including, but not limited to:

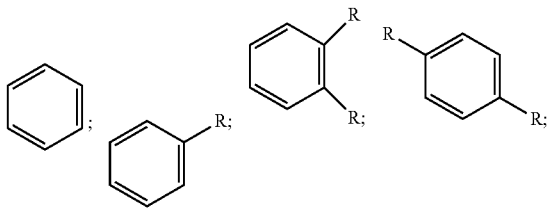

In the case of a fused cyclic system, the R group can be substituted on any otherwise unsubstituted carbon through the fused system. Thus, the case of a napthyl group with the structure:

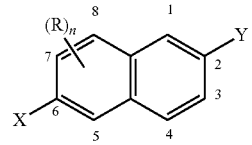

already substituted at carbons 2 and 6 by substituents X and Y, wherein n is one (1) comprises compound groups including:

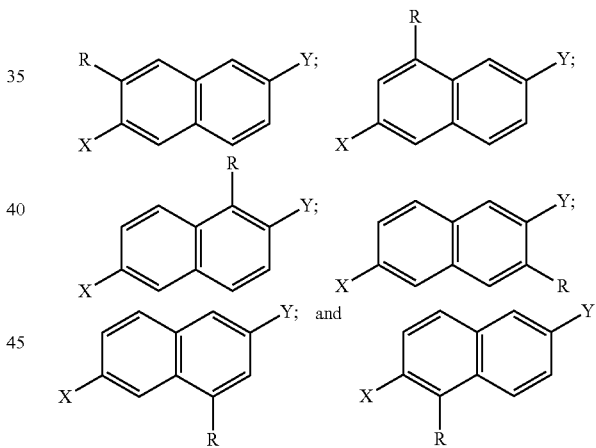

wherein the one (1) R substituent can be attached at any carbon on the naphthyl parent structure not occupied by another designated substituent, as in this case carbon 6 is substituted by X and carbon 2 is substituted by Y.

The term "protecting group" refers to groups that are known in the art of organic synthesis for masking chemical groups (e.g., hydroxyl, amino, carboxyl, and thiol groups) during chemical group transformations elsewhere in the molecule. For example, hydroxyl protecting groups are groups that can replace the hydrogen atom of a hydroxy group on a molecule and that are stable and non-reactive to reaction conditions to which the protected molecule is to be exposed. Suitable protecting groups are described, for example, in Greene and Wuts, Protective Groups in Organic Synthesis, 3$^{rd}$ Edition; New York, John Wiley & Sons, Inc., 1999. Hydroxyl protecting groups include, for example, but are not limited to, groups that can be reacted with hydroxyl groups to form ethers, such as silyl ethers (e.g., trimethylsilyl (TMS), triethylsilyl (TES), tert-butyldimethylsilyl (TBDMS, sometimes also referred to as TBS), t-butyldiphenylsilyl (TBDPS), or phenyldimethylsilyl ethers) substituted methyl ethers (e.g., methoxymethyl (MOM), benzyloxymethyl (BOM), tetrahydropyranyl (THP)), substituted ethyl ethers, benzyl ethers and substituted benzyl ethers; esters (e.g., acetate, formate, chloroacetate); and carbonates.

The term "aprotic solvent" refers to a solvent molecule which can neither accept nor donate a proton. Examples of aprotic solvents include, but are not limited to, ethyl acetate; carbon disulphide; ethers, such as, diethyl ether, tetrahydrofuran (THF), ethylene glycol dimethyl ether, dibutyl ether, diphenyl ether, MTBE, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. Additional aprotic solvents include, for example, acetone, acetonitrile, butanone, butyronitrile, chlorobenzene, chloroform, 1,2-dichloroethane, dimethylacetamide, N,N-dimethylformamide (DMF), dimethylsulfoxide (DMSO), and 1,4-dioxane.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The terms "Cdc42 modulator," "modulator," and "modulator compound" as used herein refer to a compound that modulates an activity of Cdc42, i.e., that activates or inhibits Cdc42 and/or a Cdc42 cellular process, such as but not limited to the interaction between Cdc42 and intersectin (ITSN). In some embodiments, the modulator is an inhibitor. In some embodiments, the modulator is an activator. The term encompasses both agonists and antagonists. In some embodiments, the modulator is dual functional and can act as an agonist when an upstream activating signal (an activating upstream regulator) of Cdc42 is absent or can act as an antagonist when an upstream activating signal is present and the Cdc42 is already activated. Methods of detecting Cdc42 inhibition or activation are described, for example, in U.S. Patent Application Publication No. 2014/0194451, incorporated herein by reference in its entirety, as well as in the examples (e.g., in Example 2), hereinbelow.

In some embodiments, the compound modulates (inhibits or activates) an interaction between intersectin (ITSN) and Cdc42 and/or ITSN-Cdc42 signaling. Thus, in some embodiments, the compound is an ITSN-Cdc42 modulator.

The terms "treatment", "treat", and "treating" as used herein encompasses inducing inhibition, regression, or stasis of a disease or disorder, e.g., AD, or alleviating at least one symptom of the disease. The terms can further encompass delaying the onset of the disease (e.g., delaying the onset of a noticeable symptom of the disease) and slowing the progression of the disease (e.g., reducing the rate at which the disease progresses, such as by delaying increases in severity of a symptom of the disease, reducing the rate of occurrence of a symptom of the disease, and/or by delaying the onset of an additional symptom). Treating can include treating a subject having, suspected of having, or at risk for developing Alzheimer's disease or symptoms thereof. In some embodiments, treating Alzheimer's disease results in a reduction in the amount of Aβ peptide in the brain and/or a reduction in the number and/or size of amyloid plaques. In some embodiments, treating AD can result in elimination of amyloid deposition, hyperphosphorylation of tau proteins, accumulation of pro-inflammatory microglia, and/or the inhibition of actin dynamics. In some embodiments, treating AD can result in the reduction in the severity and/or frequency of one or more cognitive or behavioral symptom associated with AD, such as, but not limited to, memory loss, confusion, impaired judgment, disorientation, language/speech difficulties, unfounded suspicions, depression, social withdrawal, personality changes, trouble walking, and trouble swallowing.

The phrase "alleviates at least one symptom," as used herein, means that a particular treatment results in a lessening of at least one symptom of a disease. Such lessening of a symptom can be a qualitative or quantitative reduction in the severity of the symptom or can be a reduction in the number of occurrences of the symptom; even though each occurrence can be as severe as it was before the treatment (one or more occurrences can also be less severe) As used herein, the term "effective amount" refers to the amount or dose of a compound of the presently disclosed subject matter, upon single or multiple dose administration to the subject, which provides a desired effect in the subject under treatment. The presently disclosed methods can include administering an effective amount of a modulator compound (e.g., as present in a pharmaceutical composition) for treating a disease (e.g., Alzheimer's disease) in the subject whereby the effective amount alleviates a molecular cause or symptom of the disease (e.g., Alzheimer's disease).

An effective amount can be readily determined by the attending diagnostician, as one skilled in the art, by the use of known techniques and by observing results obtained under analogous circumstances. In determining the effective amount or dose of agent administered, a number of factors can be considered by the attending diagnostician, such as: the species of the patient; its size, age, and general health; the particular symptoms or the severity of the disease; the response of the individual patient; the particular agent administered; the mode of administration; the bioavailability characteristics of the preparation administered; the dose regimen selected; the use of concomitant medication; and other relevant circumstances.

II. General Considerations

Cdc42 is a sub-class of the small G protein Rho GTPase family and is an important regulatory protein of many cell biological functions. First identified in *Saccharomyces cerevisiae* for its involvement in cell polarization, Cdc42 was then recognized to play important roles in cytoskeletal reorganization, cellular endocytosis, regulation of cell cycle and cell transcription. Activation of Cdc42, like that of most GTPases, is achieved through the exchange of guanosine-5'-diphosphate (GDP) for guanosine-5'-triphsopahte (GTP) binding. Cycles of activation and inactivation of Rho family of GTPases are regulated by three important class of proteins, guanine nucleotide exchange factor (GEF), which catalyzes the release of GDP for GTP binding; GTPase activating protein (GAP) as negative regulatory factor to accelerate the hydrolysis of GTP of Rho GTPases from the active to inactive state; and guanosine nucleotide dissociation inhibitors (GDI) to prevent the separation of GDP from Rho GTPases, thereby inhibiting Rho GTPase activity. Rho GTPases have been implicated in a wide variety of diseases.

Intersectin (ITSN) is a multidomain adaptor protein involved in protein trafficking and synaptic modulation. ITSN contains EH and SH3 domains and at the C-terminus, the ITSN long form (ITSN-L) contains an additional DH, PH, and C2 domain. Through its DH domain, ITSN-L serves as a guanine nucleotide exchange factor (GEF) that is specific for Rho GTPase Cdc42. ITSN-L-Cdc42 signaling appears to play a role in Alzheimer's disease (AD), Down's syndrome (DS), and Huntington's disease (HD). See e.g., Hunter et al., Neuroreport, 2011, 22(15):767-772; and Wong et al., PLoS One, 2012, 7(4):e36023. ITSN is involved in dysregulation of endocytic trafficking, an early event observed in patients with AD or DS. ITSN has also been identified, in unbiased gene profiling, as one of the most highly induced genes in AD and DS patients. However, there has previously been no direct evidence on whether modifications of ITSN and/or ITSN-Cdc42 signaling is involved or affects AD pathogenesis.

Both ITSN-L and Cdc42 are involved in spine development and neuronal survival. Consistent with the roles of this signaling pathway, the Cdc42 signaling axis is believed to also play a role in other neurodevelopmental and neurocognitive disorders, such as autism and schizophrenia. See Datta et al., Biol. Psychiatry, 2015, 78(11):775-785; Moutin et al., Cereb. Cortex, 2017, 27(7):3618-3629; Ide & Lewis, Biol. Psychiatry, 2010, 68(1):25-32; Wu et al., Proc. Natl. Acad. Sci., USA, 2015, 112(50):15480-15485; and Hor et al., Cell Rep., 2014, 9(6), 2166-2179. A direct link of ITSN-Cdc42 signaling to AD pathogenesis has not previously been shown.

As a Rho GTPase, Cdc42 plays roles in the actin organization which is essential for synaptic plasticity. Therefore, while not bound by any particular theory of operation, it is thought that spine loss and/or unstable synaptic junction underlies the synaptic mechanism of AD pathogenesis. Unexpectedly, in accordance with aspects of the presently disclosed subject matter, it has been identified that Cdc42 activity is increased in human AD brain as well as in the triple transgenic AD (3×Tg-AD) mouse model. In accordance with aspects of the presently disclosed subject matter, it has been discovered that both ITSN-Cdc42 inhibitors and activators modify several behavior parameters of 3×Tg-AD mice. Further, evidence presented herein indicates that ITSN-Cdc42 modulators inhibit pathogenic progression of 3×Tg AD mice. Therefore, these modulators are believed to inhibit AD-like pathogenesis in 3×Tg AD-mice via ITSN-mediated signaling (e.g., Cdc42) that is dysregulated in AD. This is significant because (1) there is currently no effective treatment for AD; (2) the presently disclosed modulator compounds can be readily modified to provide a large class of compounds to study the benefits of ITSN-Cdc42 modulation in AD; and (3) the identification of ITSN-Cdc42 as a therapeutic target in AD provides a new alternative pharmacological class to current AD therapy.

Thus, provided in accordance with aspects of the presently disclosed subject matter is a method of treating neurodegenerative, neurocognitive, and/or neurodevelopmental diseases and disorders (e.g., AD, DS, HD, autism, schizophrenia, etc.) with Cdc42 modulators. In some embodiments, the presently disclosed subject matter provides a method of treating AD comprising the administration of a Cdc42 modulator. Also provided herein in accordance with aspects of the presently disclosed subject matter is the demonstration of the utility of the presently disclosed modulator compounds in reversing AD pathogenesis. Also provided in accordance with aspects of the presently disclosed subject matter is the demonstration of the utility of the presently disclosed modulator compounds in improving AD-related activity of daily living (ADL) and social behavior. Also provided in accordance with aspects of the presently disclosed subject matter are optimized modulator compound analogs to potentially improve drug parameters.

Most therapeutic strategies for Alzheimer's disease (AD) focus on the upstream elements in the disease process (i.e. Aβ and tau) based on the amyloid hypothesis. See Hardy & Selkoe, Science, 2002, 297(5580):353-356. The presently disclosed subject matter provides in some embodiments an effective and alternative approach to target downstream elements that are closest to the manifestation of disease phenotype—that is, at the synapse. The presently disclosed subject matter represents the first demonstration of the benefits of ITSN-Cdc42 modulation by using compounds that specifically target ITSN-Cdc42 interactions, including, but not limited to, sulfonamide substituted thioureas and analogs thereof (e.g., ureas, carbamates, thiocarbamates, etc.), disulfonamides of dibenzofurans and analogs thereof (e.g., disulfonamides of substituted dibenzofurans, and disulfonamides of dibenzothiophenes, carbazoles, and fluorenes), and acyl substituted hydrazones and analogs thereof. The development of these compounds provides an alternative pharmacological class to current AD therapy.

II. ISTN-Cdc42 Modulator Compounds

III.A. Compound of Formula (I)

In some embodiments, the presently disclosed subject matter provides a method of treating a neurodegenerative, neurocognitive, and/or neurodevelopmental disease comprising the administration of a thiourea, such as a sulfonamide-substituted thiourea or analog thereof, such as a urea, carbamate, or thiocarbamate, to a subject in need thereof. In some embodiments, the sulfonamide substituent is an aryl sulfonamide group, wherein the sulfonyl and/or nitrogen of the sulfonamide are directly attached to an aryl group.

In some embodiments, the compound has a structure of Formula (I):

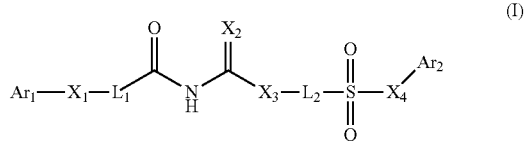

wherein:
  Ar$_1$ and Ar$_2$ are independently selected from the group comprising aryl and substituted aryl; optionally wherein one of Ar$_1$ and Ar$_2$ is heteroaryl or substituted heteroaryl;
  X$_1$ is selected from the group comprising —CH—, —S—, NR, and —O—, wherein R is selected from H, alkyl, and substituted alkyl;
  L$_1$ and L$_2$ are independently selected from the group comprising alkylene, cycloalkylene, aralkylene, and arylene;
  X$_2$ is O or S;
  X$_3$ is selected from —NR$_{12}$— and —O—, wherein R$_{12}$ is selected from H, alkyl, and substituted alkyl; and
  X$_4$ is selected from NR$_{13}$ and —O—, wherein R$_{13}$ is selected from H, alkyl, and substituted alkyl.

In some embodiments, the compound of Formula (I) includes a thiourea (i.e., wherein X$_2$ is S and X$_3$ is NR$_{12}$ (e.g., NH)). In some embodiments, the compound of Formula (I) includes a thiourea and X$_1$ is —O— and X$_4$ is NR$_{13}$ (e.g., NH). In some embodiments, the compound of Formula (I) has a structure of Formula (Ia):

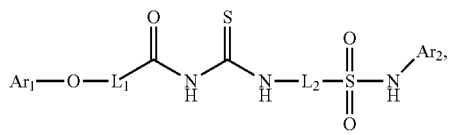

(Ia)

wherein:
Ar$_1$ and Ar$_2$ are independently selected from aryl and substituted aryl; optionally wherein one of Ar$_1$ and Ar$_2$ is heteroaryl or substituted heteroaryl; and
L$_1$ and L$_2$ are independently selected from the group comprising alkylene, cycloalkylene, aralkylene, and arylene.

In some embodiments, L$_1$ is C$_1$-C$_6$ alkylene, which can optionally be substituted with one or more alkyl group substituent. In some embodiments, L$_1$ is selected from methylene, ethylene, and propylene. In some embodiments, L$_1$ is methylene.

In some embodiments, L$_2$ is selected from cycloalkylene (e.g., cyclohexylene) and arylene (e.g., phenylene). In some embodiments, L$_2$ is phenylene.

In some embodiments, the compound of Formula (Ia) has a structure of Formula (Ib):

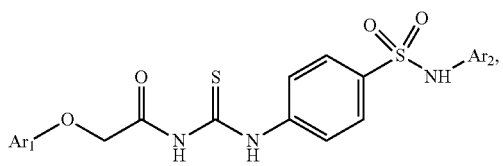

(Ib)

wherein:
Ar$_1$ and Ar$_2$ are independently selected from aryl and substituted aryl; optionally wherein one of Ar$_1$ and Ar$_2$ is heteroaryl or substituted heteroaryl.

In some embodiments, in the compounds of Formula (I), Formula (Ia), and Formula (Ib), Ar$_1$ and Ar$_2$ can be selected from the group including, but not limited to, phenyl, napthyl, anthracenyl, phenanthrenyl, pyrenyl, pyridinyl, pyrimidinyl, pyrazinyl, pyridazinyl, quinazolinyl, isoquinazolinyl, quinolinyl, isoquinalinyl, furanyl, thiophenyl, pyrrolyl, oxazolyl, imidazolyl, thiazolyl, isooxazolyl, pyrazolyl, isothiazolyl, benzofuranyl, indolyl, benothiophenyl, and carbazolyl, each of which can be substituted or unsubstituted with one or more aryl group substituents, such as, but not limited to, halo, nitro, cyano, hydroxyl, alkyl, alkoxyl, and the like. In some embodiments, Ar$_1$ and Ar$_2$ are each six-membered ring aryl or heteroaryl groups. In some embodiments, one of Ar$_1$ and Ar$_2$ is substituted or unsubstituted heteroaryl (e.g., a six-membered ring heteroaryl) and one of Ar$_1$ and Ar$_2$ is substituted or unsubstituted phenyl. In some embodiments, Ar$_2$ is substituted or unsubstituted phenyl. In some embodiments, Ar$_2$ is a substituted or unsubstituted nitrogen-containing heteroaryl group. In some embodiments, Ar$_2$ is substituted or unsubstituted pyrimidinyl.

In some embodiments, the compound of Formula (I) has a structure of Formula (Ic):

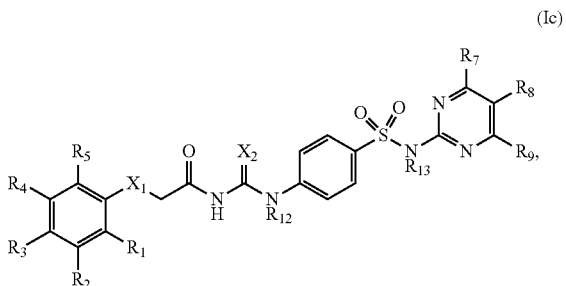

(Ic)

wherein:
each of R$_1$-R$_5$ and R$_7$-R$_9$ is independently selected from the group comprising H, halo, nitro, cyano, hydroxyl, carboxyl, acyl, alkyl, substituted alkyl, alkoxyl, aralkoxyl, aryloxyl, amino, and sulfonyl;
X$_1$ is selected from —CH—, —S—, NR, and —O—, wherein R is selected from H, alkyl, and substituted alkyl;
X$_2$ is selected from O and S;
R$_{12}$ is selected from H, alkyl, and substituted alkyl; and
R$_{13}$ is selected from H, alkyl, and substituted alkyl.

In some embodiments, the compound of Formula (Ic) includes a thiourea (i.e., X$_2$ is S). In some embodiments, R$_{12}$ is H. In some embodiments, R$_{13}$ is H.

In some embodiments, X$_1$ is —O—.

In some embodiments, the compound of Formula (Ic) has a structure of Formula (Id):

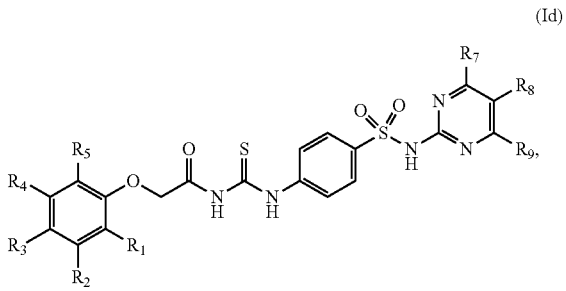

(Id)

wherein:
each of R$_1$-R$_5$ and R$_7$-R$_9$ is independently selected from the group comprising H, halo, nitro, cyano, hydroxyl, carboxyl, acyl, alkyl, substituted alkyl, alkoxyl, aralkoxyl, aryloxyl, amino, and sulfonyl.

In some embodiments, each of R$_1$-R$_5$ is independently selected from the group comprising H, halo, alkyl (e.g., C$_1$-C$_6$ straight or branched alkyl), and alkoxy (e.g., C$_1$-C$_6$ alkoxy). In some embodiments, R$_2$ and R$_4$ are each H. In some embodiments, each of R$_1$, R$_3$, and R$_5$ are independently selected from H, halo, alkyl and alkoxy. In some embodiments, one or two of R$_1$, R$_3$, and R$_5$ are selected from halo, alkyl, and alkoxy. In some embodiments, R$_3$ and R$_5$ are selected from halo, alkyl, and alkoxy. In some embodiments, R$_3$ and R$_5$ are each halo (e.g., Cl or Br). In some embodiments, R$_3$ is bromo and R$_5$ is chloro.

In some embodiments, R$_3$ is halo, alkyl, or alkoxy. In some embodiments, R$_3$ is alkyl or alkoxy. In some embodiments, R$_3$ is alkyl. In some embodiments, R$_3$ is selected from methyl, ethyl, and propyl (e.g., n-propyl), and butyl (e.g., tert-butyl). In some embodiments, R$_3$ is alkoxy. In some embodiments, R$_3$ is methoxy or ethoxy.

In some embodiments, each of $R_7$-$R_9$ is selected from H and alkyl. In some embodiments, each of $R_7$-$R_9$ is selected from H and methyl. In some embodiments, $R_7$ and $R_9$ are each methyl and Ra is H.

In some embodiments, the compound of Formula (Id) is selected from the group comprising:

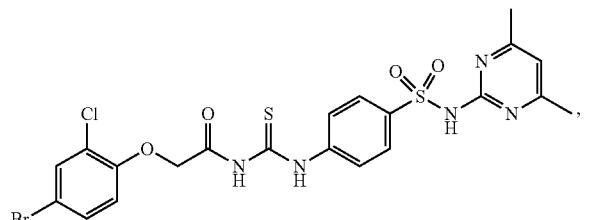

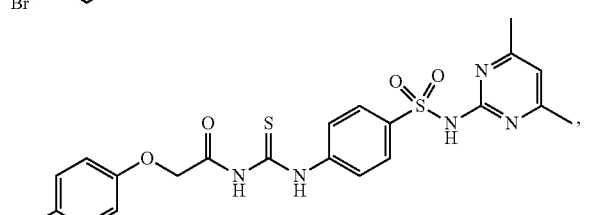

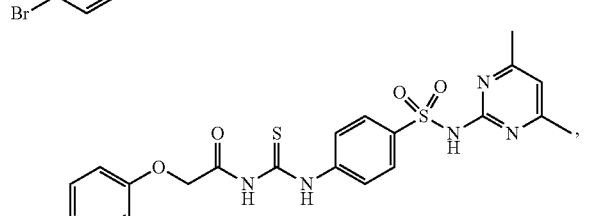

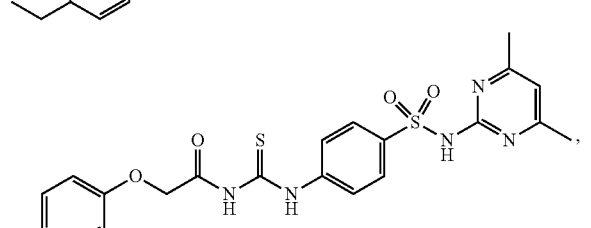

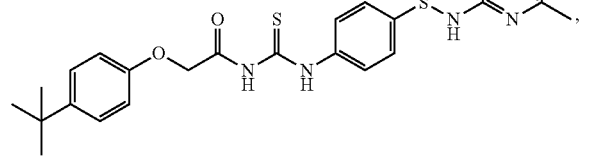, and

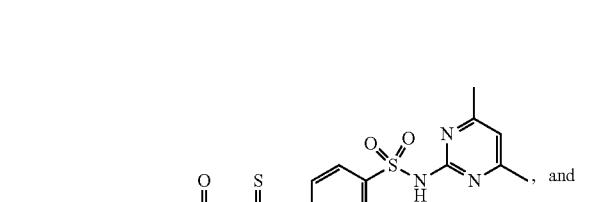

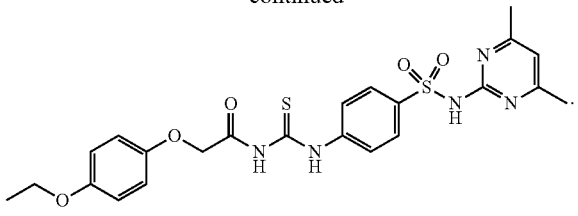

In some embodiments, $R_3$ is Br, $R_5$ is Cl, and $R_7$ and $R_9$ are each methyl and the compound of Formula (Id) is ZCL278, i.e., the compound having the structure:

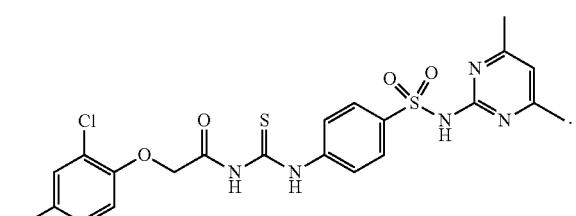

In some embodiments, the compound being administered according to a method as described herein can be a synthetic intermediate or biological metabolite of the compound of Formula (I), (Ia), (Ib), (Ic) or (Id). For example, in some embodiments, the compound can have a structure of Formula (Ie):

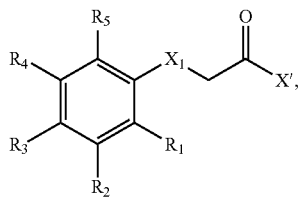

wherein:
$R_1$, $R_2$, $R_3$, $R_4$, and $R_5$ are each independently selected from the group comprising H, halo, nitro, cyano, hydroxyl, carboxyl, acyl, alkyl, substituted alkyl, alkoxyl, aralkoxyl, aryloxyl, amino, and sulfonyl;
$X_1$ is selected from —CH—, —S—, NR, and —O—, wherein R is selected from H, alkyl, and substituted alkyl; and
X' is selected from OH or alkoxy (e.g., methoxy or ethoxy).

In some embodiments, $X_1$ is —O—. In some embodiments, X' is OH.

In some embodiments, $R_2$ and $R_4$ are each H. In some embodiments, one or more of $R_1$, $R_3$, and $R_5$ is selected from halo, alkyl, and alkoxyl. In some embodiments, two of $R_1$, $R_3$, and $R_5$ is selected from halo, alkyl, and alkoxyl. In some embodiments, $R_1$ and $R_3$ are each halo. In some embodiments, $R_3$ is alkyl or alkoxyl.

The compounds of Formula (I), (Ia), (Ib), (Ic), (Id), and (Ie) can be prepared by methods known in the art of organic synthesis as set forth in part by Schemes 1 and 2, below, and the following description. In the synthesis schemes presented herein, it is understood that protecting groups for sensitive or reactive groups are employed where necessary in accordance with general principles of chemistry. Protecting groups are manipulated according to standard methods or organic synthesis. See e.g., Greene and Wuts (1999) Protecting Groups in Organic Synthesis, Third Edition, John Wiley & Sons, Inc. These groups are removed at a convenient stage of the compound synthesis using methods that are readily apparent to those skilled in the art.

The synthesis of an exemplary compound of Formula (I), i.e., compound 1 (also referred to herein as ZCL278), was performed as described in U.S. Patent Application Publication 2014/019445, which is incorporated herein by reference in its entirety. Briefly, the synthesis was performed as shown in Scheme 1, below. First, 4-bromo-2-chlorophenol (1a) was reacted with 2-ethyl bromoacetate (1b) in the presence of potassium carbonate to provide compound 1c. The ethyl ester group of compound 1c was saponified using sodium hydroxide to provide compound 1d. The carboxylic acid group of compound 1d was transformed into an acid chloride using thionyl chloride, thereby providing compound 1. Compound 1e was reacted with sodium thiocyanate and then with amine 1f to provide the thiourea compound 1.

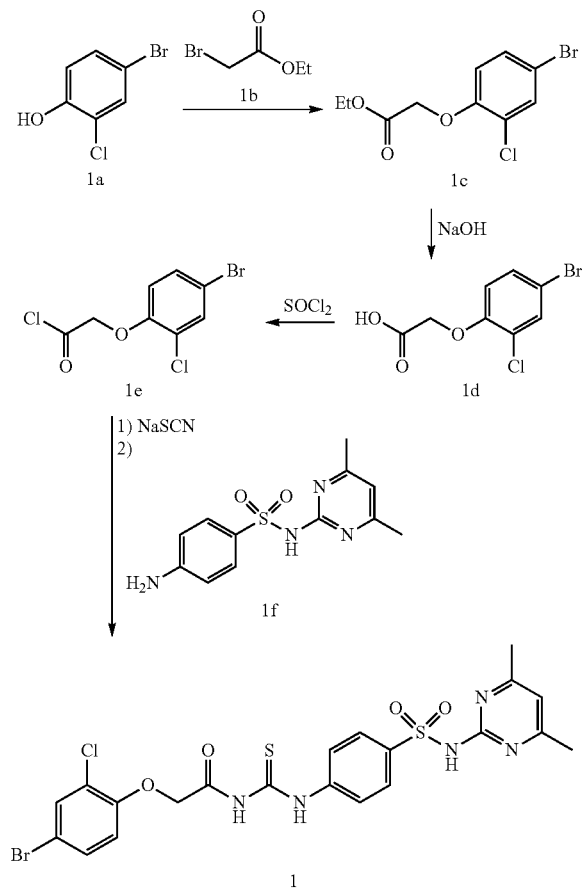

Additional compounds of Formula (I) can be prepared by using other starting materials and reagents in variations of the synthetic route shown in Scheme 1. For example, a generic synthetic route to compounds of Formula (I) is shown in Scheme 2, below. First, an aryl starting material a is reacted with an ester compound b that comprises a suitable leaving group (e.g., a halo group, such as F, Br, Cl, or I or another good leaving group such as a sulfonate (e.g., toluenesulfonate (OTs) or methanesulfonate (OMs)). Ester compound b in Scheme 2 is shown with an alkylene chain with one or more methylene ($-CH_2-$) unit. In some embodiments, q is 1 and ester compound b is an alkyl 2-haloacetate. However, in some embodiments, the alkylene chain can be replaced with an arylene group wherein the arylene group is substituted with an alkyl group comprising a good leaving group. For example, ester compound b can be replaced by an alkyl ester of a substituted benzoic acid. Aryl starting material a includes a nucleophilic group $X_1-H$, such that the compound includes a hydroxyl group, a thiol group, or an amino group (e.g., $X_1$ is $-O-$, $-S-$, $-NH-$, or $-N(alkyl)-$). Aryl starting material a can be substituted or unsubstituted with one or more aryl group substituents $R^1$. Thus, p in the formula of compound a is an integer between 0 and the number of substitutable carbon atoms on $Ar_1$. In some embodiments, $Ar^1$ is phenyl and p is an integer between 0 and 5.

Returning to the synthetic route described in Scheme 2, the alkyl ester group of compound c can be removed by contacting the compound with an alkali metal hydroxide, such as NaOH, KOH, or LiOH. Alternative methods (e.g., acid catalyzed hydrolysis) of removing the ester can also be used, as would be understood by one of ordinary skill in the art. Carboxylic acid d can be transformed to acid chloride e via reaction with thionyl chloride. Acid chloride e can be reacted with sodium thiocyanate and then with compound f, which is an alcohol (i.e., when $X_3$ is $-O-$) or an amine (i.e., when $X_3$ is $-NH-$ or $-N(alkyl)-$) to form a thiocarbamate or thiourea compound of Formula (I), respectively. Alternatively, acid chloride e can be reacted with sodium cyanate and then with alcohol or amine f to provide a carbamate or urea of Formula (I). Variables $L_2$, $X_4$, and $Ar_2$ in the structure of compound f are as described for the compound of Formula (I). $Ar_2$ can be unsubstituted or substituted with one or more aryl group substituents $R^2$. Variable s in compound f is an integer between 0 and the number of substitutable carbons in $Ar_2$. In some embodiments, $Ar_2$ is phenyl and s is an integer between 0 and 5. In some embodiments, $Ar_2$ is pyrimidinyl and s is a variable between 0 and 3.

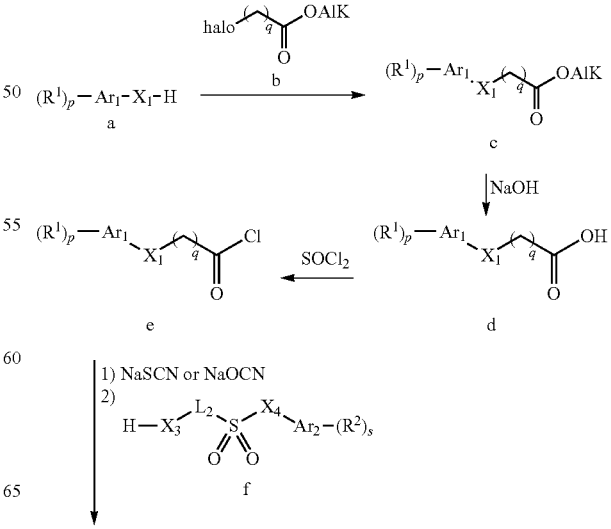

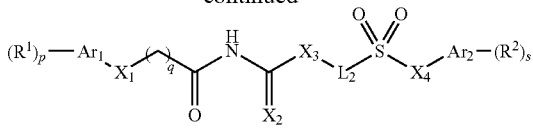

III.B. Compounds of Formula (II)

In some embodiments, the presently disclosed subject matter provides a method of treating a neurodegenerative, neurocognitive, and/or neurodevelopmental disease comprising the administration of a disulfonamide, such as a disulfonamide of an aryl compound, to a subject in need thereof. In some embodiments, the aryl compound is a fused multi-ring aryl system, such as, but not limited to dibenzofuran, dibenzothiofuran, carbazole, or fluroene, or an analog thereof, such as a urea, carbamate, or thiocarbamate. In some embodiments, one or more of the two sulfonamide substituents is an aryl sulfonamide group.

In some embodiments, the compound is a disulfonamide compound having a structure of Formula (II):

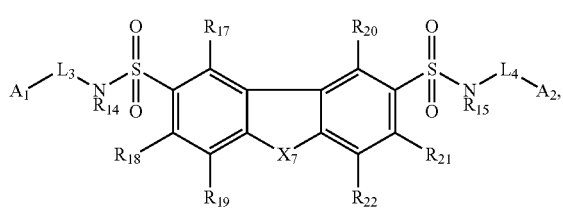

(II)

wherein
- $A_1$ and $A_2$ are independently selected from the group comprising alkyl, substituted alkyl, cycloalkyl, substituted cycloalkyl, heterocycle, substituted heterocycle, aryl, substituted aryl, heteroaryl, and substituted heteroaryl;
- $L_3$ and $L_4$ are each independently present or absent, and, if present are independently a —(CH$_2$)$_n$— group, wherein n is an integer between 1 and 10 (i.e., 1, 2, 3, 4, 5, 6, 7, 8, 9, or 10);
- $R_{14}$ and $R_{15}$ are independently selected from H, alkyl, and substituted alkyl;
- $R_{17}$, $R_{18}$, $R_{19}$, $R_{20}$, $R_{21}$, and $R_{22}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and
- $X_7$ is selected from —CH$_2$—, —NH—, —O—, and —S—.

Accordingly, in some embodiments, the compound is a di-sulfonamide of a carbazole, a fluorene, a dibenzofuran, or a dibenzothiophene. In some embodiments, $X_7$ is O and the modulator is a disulfonamide of a dibenzofuran.

In some embodiments, $A_1$ and $A_2$ are independently selected from the group including, but not limited to, methyl, substituted or unsubstituted cyclohexyl, substituted or unsubstituted phenyl, substituted or unsubstituted pyridinyl, substituted or unsubstituted tetrahydrofuranyl, substituted or unsubstituted tetrahydrothiophenyl, substituted or unsubstituted pyrrolidinyl, substituted or unsubstituted tetrahydropyranyl, substituted or unsubstituted tetrahydrothiopyranyl, and substituted or unsubstituted piperidinyl. In some embodiments, $A_1$ and $A_2$ are independently selected from the group including, but not limited to:

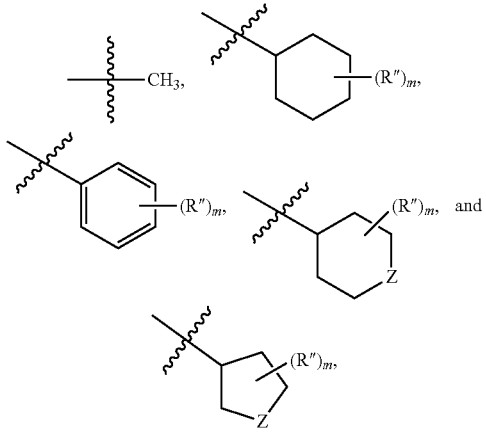

wherein m is an integer corresponding to the number of replaceable hydrogen atoms on the ring carbon atoms. For example, when $A_1$ or $A_2$ is a cyclohexyl group, m is 10. When $A_1$ or $A_2$ is phenyl, m is 5. When $A_1$ or $A_2$ is piperidinyl (i.e., a six-membered ring containing one ring nitrogen), m is 8.

In some embodiments, $R_{17}$, $R_{18}$, $R_{19}$, $R_{20}$, $R_{21}$, and $R_{22}$ are each H.

In some embodiments, $A_1$ is phenyl or substituted phenyl and La is absent and the compound of Formula (II) has a structure of Formula (IIa):

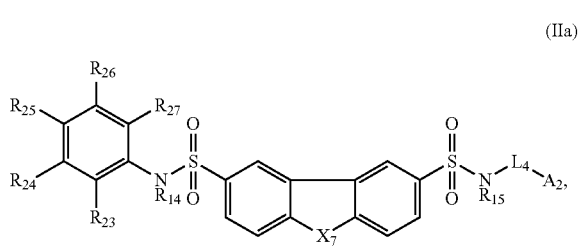

(IIa)

wherein:
- $A_2$ is selected from the group comprising alkyl, substituted alkyl, cycloalkyl, substituted cycloalkyl, heterocycle, substituted heterocycle, aryl, substituted aryl, heteroaryl, and substituted heteroaryl;
- $L_4$ is present or absent, and, if present is —(CH$_2$)$_n$—, wherein n is an integer between 1 and 10 (i.e., 1, 2, 3, 4, 5, 6, 7, 8, 9, or 10);
- $R_{14}$ and $R_{15}$ are independently selected from H, alkyl, and substituted alkyl;
- $R_{23}$, $R_{24}$, $R_{25}$, $R_{26}$, and $R_{27}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and
- $X_7$ is selected from —CH$_2$—, —NH—, —O—, and —S—.

In some embodiments, $X_7$ is O.

In some embodiments, at least one of $R_{14}$ and $R_{15}$ is H. In some embodiments, $R_{14}$ and $R_{15}$ are each H.

In some embodiments, $R_{23}$ is hydroxyl. In some embodiments, $R_{24}$, $R_{25}$, $R_{26}$, and $R_{27}$ are each H.

In some embodiments, both $A_1$ and $A_2$ are each phenyl or substituted phenyl. Thus, in some embodiments, the compound of Formula (II) has a structure of Formula (IIb):

In some embodiments, $R_{26}$ is OH. In some embodiments, $R_{26}$, $R_{30}$, $R_{31}$, and $R_{32}$ are each H.

In some embodiments, $X_7$ is —O—.

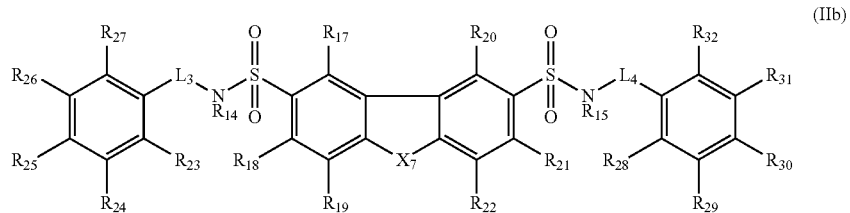

(IIb)

wherein:
- $L_3$ and $L_4$ are independently present or absent, and, if present are independently —(CH$_2$)$_n$—, wherein n is an integer between 1 and 10;
- $R_{14}$ and $R_{15}$ are independently selected from H, alkyl, and substituted alkyl;
- $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{26}$, $R_{29}$, $R_{30}$, Rai, and $R_{32}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and
- $X_7$ is selected from —CH$_2$—, —NH—, —O—, and —S—.

In some embodiments, $X_7$ is O.

In some embodiments, at least one of $R_{14}$ and $R_{15}$ is H. In some embodiments, $R_{14}$ and $R_{15}$ are each H.

In some embodiments, $R_{17}$, $R_{18}$, $R_{19}$, $R_{20}$, $R_{21}$, and $R_{22}$ are each H.

In some embodiments, $R_{23}$ is hydroxyl. In some embodiments, $R_{24}$, $R_{25}$, $R_{26}$, and $R_{27}$ are each H.

In some embodiments, both $A_1$ and $A_2$ are each phenyl or substituted phenyl, $L_3$ and $L_4$ are each absent and $R_{17}$, $R_{18}$, $R_{19}$, $R_{20}$, $R_{21}$, and $R_{22}$ are each H. Thus, in some embodiments, the compound of Formula (IIb) has a structure of Formula (IIc):

(IIc)

wherein:
- $R_{14}$ and $R_{15}$ are independently selected from H, alkyl, and substituted alkyl;
- $R_{23}$, $R_{24}$, $R_{25}$, $R_{26}$, $R_{27}$, $R_{26}$, $R_{28}$, $R_{30}$, $R_{31}$, and $R_{32}$ are each independently selected from the group comprising H, halo, nitro, cyano, hydroxyl, carboxyl, acyl, alkyl, substituted alkyl, alkoxyl, aralkoxyl, aryloxyl, amino, and sulfonyl; and
- $X_7$ is selected from —CH$_2$—, —NH—, —O—, and —S—.

In some embodiments, at least one of $R_{14}$ and $R_{15}$ is H. In some embodiments, $R_{14}$ and $R_{15}$ are each H.

In some embodiments, $R_{23}$ is hydroxyl. In some embodiments, $R_{24}$, $R_{25}$, $R_{26}$, and $R_{27}$ are each H.

In some embodiments, the compound of Formula (II), (IIa), (IIb), or (IIc) is the compound ZCL279, which has the structure:

The compounds of Formula (II), (IIa), (IIb), and (IIc) can be prepared by methods known in the art of organic synthesis, such as set forth in part by Scheme 3 below, and the following description. For example, Scheme 3 shows the synthesis of exemplary compounds of Formulas (II). Additional compounds of Formulas (II), (IIa), (IIb), and (IIc) can be prepared by analogous synthesis routes. In the syntheses of the compounds, it is understood that protecting groups for sensitive or reactive groups are employed where necessary in accordance with general principles of chemistry. Protecting groups are manipulated according to standard methods or organic synthesis. See e.g., Greene and Wuts (1999) Protecting Groups in Organic Synthesis, Third Edition, John Wiley & Sons, Inc. These groups are removed at a convenient stage of the compound synthesis using methods that are readily apparent to those skilled in the art.

Scheme 3. Synthesis of Exemplary Compounds of Formula (II).

-continued

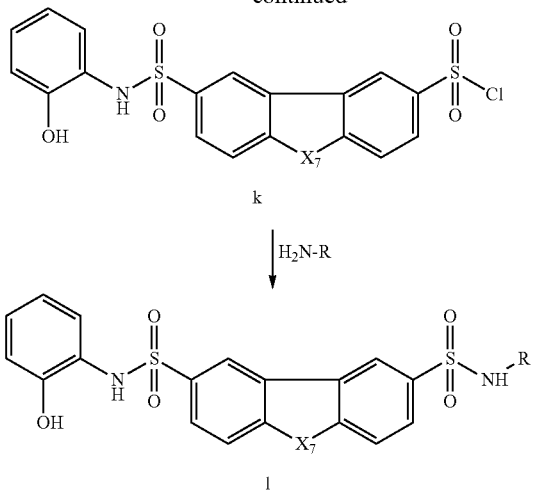

As shown in Scheme 3, above, the synthesis of the compound of Formula (II) involves the reaction of a starting material g (e.g., dibenzofuran when $X_7$ is —O—) with chlorosulfonic acid ($ClSO_3H$) in thionyl chloride ($SOCl_2$) to provide chlorosulfonic acid intermediate h. Intermediate h is then reacted with 2-hydroxylbenzylamine i (e.g. in solution with ethanol at room temperature) to provide sulfonamide j. Then sulfonamide j reacted with chlorosulfonic acid in thionyl chloride to provide a second chlorosulfonic acid intermediate k. Intermediate k is reacted with a second amine ($H_2N$—R) to provide the disulfonamide compound l of Formula (II). The identity of the second amine can vary depending upon the identity of $L_4$ and $Ar_2$. Suitable second amines are shown below in Scheme 4. In addition to the primary amines shown in Scheme 4, secondary amines can be used (e.g., when $R_{15}$ is other than H). In addition, in some embodiments, 2-hydroxylbenzylamine i can be replaced by another amine, such as one of the amines shown in Scheme 4.

Scheme 4. Second Amines for Synthesis of Compounds of Formula (II).

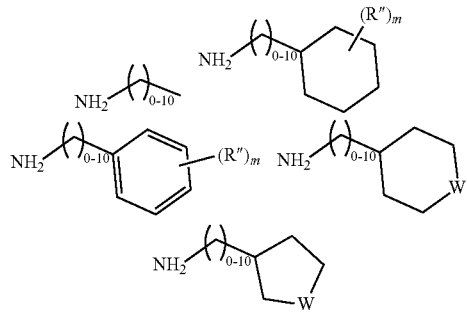

W = —O—, —NH—, or —S—,
R" = alkyl, substituted alkyl, hydroxyl, halo, acyl, nitro, cyano, etc.
m = an integer corresponding to the replaceable hydrogen atoms III.C. Compounds of Formula (III)

In some embodiments, the presently disclosed subject matter provides a method of treating a neurodegenerative, neurocognitive, and/or neurodevelopmental disease comprising the administration of a hydrazine, such as an acyl hydrazone or an acyl hydrazone analog (i.e. wherein the acyl group carbonyl is replaced by a thiocarbonyl), to a subject in need thereof. In some embodiments, the hydrazone further includes one or more aryl or substituted aryl groups.

In some embodiments, the modulator is an acyl-substituted hydrazone compound having a structure of Formula (III):

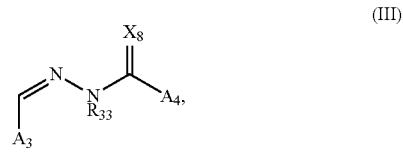

wherein:
$A_3$ is selected from the group comprising cycloalkyl, substituted cycloalkyl, heterocycle, substituted heterocycle, aryl, substituted aryl, heteroaryl, and substituted heteroaryl;
$A_4$ is selected from the group comprising alkoxy, aralkoxy, aryloxy, amino, cycloalkyl, substituted cycloalkyl, heterocycle, substituted heterocycle, aryl, substituted aryl, heteroaryl, and substituted heteroaryl;
$R_{33}$ is selected from H, alkyl, and substituted alkyl; and
$X_8$ is selected from O, S, and $CH_2$.

In some embodiments, $X_8$ is O. In some embodiments, $X_8$ is S. In some embodiments, $R_{33}$ is H.

In some embodiments, $A_4$ is selected from alkoxy, aralkoxy, aryloxy, and amino. Thus, for example, in some embodiments, $A_4$ is selected from methoxy, ethoxy, n-propoxy, isopropoxy, n-butoxy, tert-butoxy, isobutoxy, n-pentyloxy, n-hexyloxy, or another branched or straight chain $C_1$-$C_{12}$ alkyloxyl group; benzyloxy, methyamino, ethylamino, or another alkylamino, dialkylamino, arylamino group. In some embodiments, the $A_4$ alkoxy, aralkoxy, aryloxy, alkylamino, dialkylamino, or arylamino group can be further substituted by one or more alkyl or aryl group substituents, e.g., halo, hydroxyl, acyl, etc.

In some embodiments, $A_3$ and $A_4$ can be independently selected from the group including, but not limited to, methyl, substituted or unsubstituted cyclohexyl, substituted or unsubstituted phenyl, substituted or unsubstituted pyridinyl, substituted or unsubstituted furanyl, substituted or unsubstituted tetrahydrofuranyl, substituted or unsubstituted tetrahydrothiophenyl, substituted or unsubstituted pyrrolidinyl, substituted or unsubstituted tetrahydropyranyl, substituted or unsubstituted tetrahydrothiopyranyl, and substituted or unsubstituted piperidinyl.

In some embodiments, one of $A_3$ and $A_4$ is phenyl or substituted phenyl.

In some embodiments, the compound of Formula (III) has a structure of Formula (IIIa):

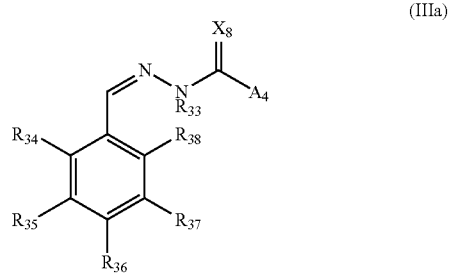

wherein

A$_4$ is selected from the group comprising alkoxy, aralkoxy, aryloxy, amino, cycloalkyl, substituted cycloalkyl, heterocycle, substituted heterocycle, aryl, substituted aryl, heteroaryl, and substituted heteroaryl;

X$_8$ is selected from O and CH$_2$;

R$_{33}$ is selected from H, alkyl, and substituted alkyl; and each of R$_{34}$, R$_{35}$, R$_{36}$, R$_{37}$, R$_{39}$, R$_{40}$, R$_{41}$, R$_{42}$, and R$_{43}$ are independently selected from the group comprising H, halo, nitro, cyano, hydroxyl, carboxyl, acyl, alkyl, substituted alkyl, alkoxyl, aralkoxyl, aryloxyl, amino, and sulfonyl.

In some embodiments, Z$_4$ is selected from alkoxy, aralkoxy, and alkylamino. In some embodiments, X$_8$ is S. In some embodiments, X$_8$ is O.

In some embodiments, the compound of Formula (IIIa) is one of the compounds:

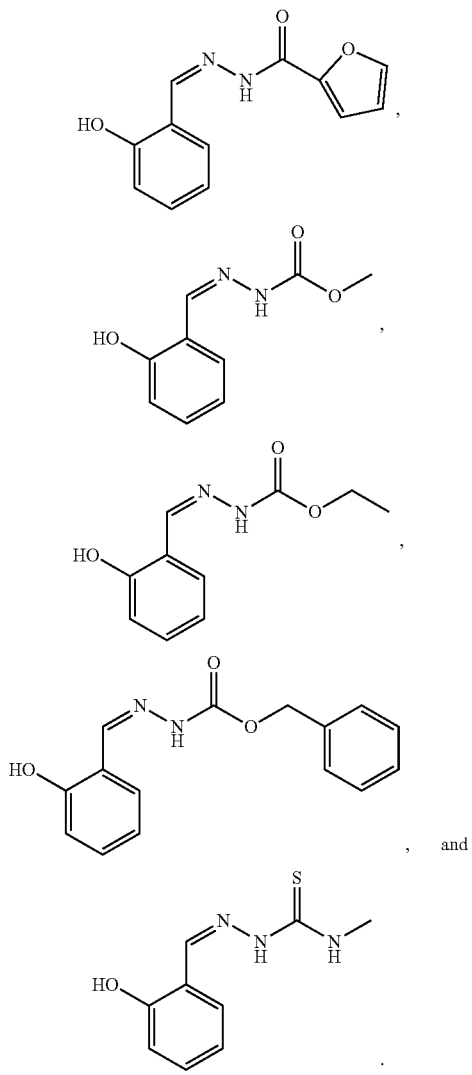

In some embodiments, both of A$_3$ and A$_4$ are phenyl or substituted phenyl. Thus, in some embodiments, the compound of Formula (III) has a structure of Formula (IIIb):

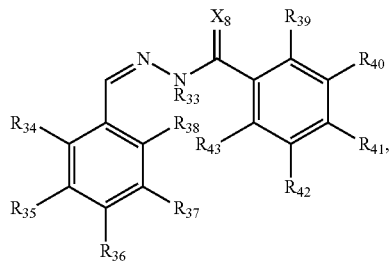

wherein

X$_8$ is selected from O and CH$_2$;

R$_{33}$ is selected from H, alkyl, and substituted alkyl; and each of R$_{34}$, R$_{35}$, Re, R$_{37}$, R$_{39}$, R$_{40}$, R$_{41}$, R$_{42}$, and R$_{43}$ are independently selected from the group comprising H, halo, nitro, cyano, hydroxyl, carboxyl, acyl, alkyl, substituted alkyl, alkoxyl, aralkoxyl, aryloxyl, amino, and sulfonyl.

In some embodiments, X$_8$ is O. In some embodiments, R$_{33}$ is H or C$_1$-C$_6$ alkyl (i.e., methyl, ethyl, n-propyl, isopropyl, n-butyl, isobutyl, n-pentyl, or isopentyl)

In some embodiments, R$_{34}$ is OH. In some embodiments, R$_{35}$, R$_{36}$, R$_{37}$, and R$_{38}$ are each H.

In some embodiments, R$_{39}$, R$_{41}$, and R$_{43}$ are each H. In some embodiments, one or both of R$_{40}$ and R$_{42}$ are OH.

In some embodiments, the compound of Formula (III) is ZCL367, the compound having the structure:

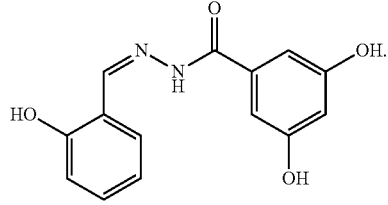 [SMILES: O=C(N/N=C\c1ccccc1O)c1cc(O)cc(O)c1]

In some embodiments, the compounds of Formula (III) can be prepared by contacting a suitable aryl aldehyde with a hydrazide, i.e., a compound comprising a nitrogen-nitrogen single bond wherein one of the two nitrogen atoms are substituted with an acyl group. The synthesis of an exemplary compound of Formula (III) is shown below in Scheme 5. As shown in Scheme 5, hydrazide n can be contacted with aldehyde m to undergo a condensation reaction to form hydrazone o of Formula (III). In some embodiments, the reaction can be performed in an aqueous solution at a pH of between about 5 and about 7.5. In some embodiments, the reaction can be performed in a protic solvent (e.g., an alcohol, such as ethanol). In some embodiments, the reaction can be performed in the presence of a catalyst, e.g., an acid, such as acetic acid, or a base, e.g., aniline. Hydrazide n can be prepared by contacting an acyl halide, anhydride or ester with a hydrazine (e.g., H$_2$N—NH$_2$). Hydrazide n can be substituted with other hyrazides or thio-analogs thereof (i.e., wherein the carbonyl is replaced by thiocarbonyl) to form additional compounds of Formula (III). Similarly, aldehyde m can be replaced with another aldehyde, e.g., a commercially available aldehyde (e.g., a substituted benzaldehyde) or an aldehyde that can be prepared by methods known in the field of organic synthesis (e.g., reduction of a substituted benzoic acid, oxidation of a phenol, aromatic substitution, etc.).

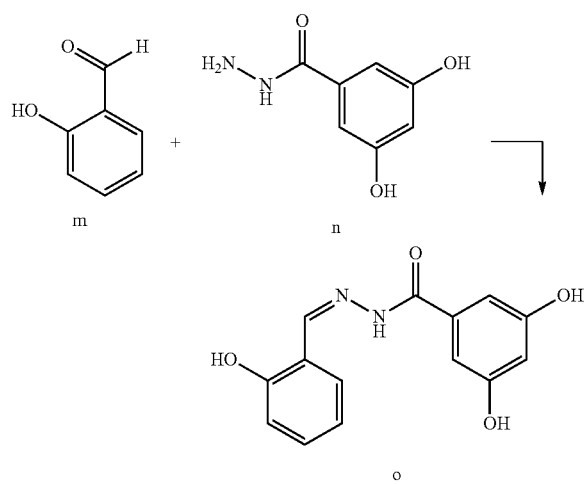

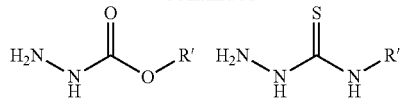

Scheme 5. Synthesis of Exemplary Compound of Formula (III).

The structures of exemplary aldehydes for use in preparing compounds of Formula (III) are shown in Scheme 6, below, while the structures of exemplary hydrazides are shown in Scheme 7, below. In both Schemes 6 and 7, R is an optional aryl or alkyl group substituent (e.g., halo, hydroxy, alkyl, etc.), while X is an optional heteroatom, e.g., N for the aryl compounds and NH, 0, or S for the other heterocyclic compounds. R' in Scheme 7 can be alkyl, substituted alkyl, aralkyl, or substituted aralkyl.

Scheme 6. Exemplary Aldehydes for the Synthesis of Compounds of Formula (III).

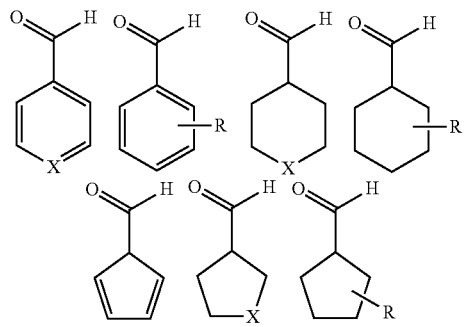

Scheme 7. Exemplary Hydrazides for the Synthesis of Compounds of Formula (III).

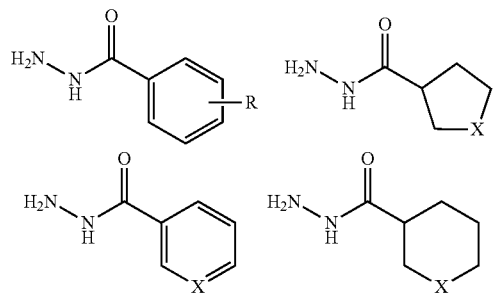

IV. Methods of Treatment

IV.A. Methods of Treating Neurodegenerative, Neurocognitive, and/or Neurodevelopmental Diseases Using Cdc42 Modulators In some embodiments, the presently disclosed subject matter provides a method of treating a disease or disorder involving Cdc42 (or another Rho GTPase, e.g., RhoA or Rac1) and/or ITSN dysregulation in a subject in need thereof. In some embodiments, the method comprises the administration of a compound that modulates Cdc42, i.e., a Cdc42 modulator compound, to a subject in need thereof. In some embodiments, the modulator compound is a compound that modulates ITSN-Cdc42 interaction. As described for example, hereinabove, many neurodegenerative, neurocognitive, and/or neurodevelopmental diseases and/or disorders are believed to involve Cdc42 and/or ITSN dysregulation. Thus, in some embodiments, the disease or disorder involving Cdc42 and/or ITSN dysregulation is a neurodegenerative, neurocognitive, and/or neurodevelopmental disease and/or disorder.

In some embodiments, the presently disclosed subject matter provides a method of treating a neurodegenerative, neurocognitive and/or neurodevelopmental disease and/or disorder wherein the method comprises administering a Cdc42 modulator to a subject in need thereof, e.g., in order to return dysregulated ITSN-Cdc2 signaling to the homeostasis of a healthy individual. In some embodiments, the modulator is a compound a compound selected from the group including, but not limited to the compounds having a structure of one of Formulas (I), (Ia), (Ib), (Ic), (Id), (Ie), (II), (IIa), (IIb), (IIc), (III), (IIIa), or (IIIb) as described hereinabove. In some embodiments, the compound is ZCL278, ZCL279, ZCL367 or another compound of Table 1, below. However, it is noted that other compounds, such as those described in the Tables of Example 7, below, can also be used as Cdc42 modulators according to the presently disclosed methods.

The term "neurodegenerative disease" as used herein refers to a condition that primarily affects the neurons of the brain. In these conditions, brain neurons suffer from loss of structure and/or function, including neuronal cell death. Exemplary neurodegenerative diseases include, but are not limited to, AD, HD, Parkinson's disease (PD), motor neuron diseases, prion disease, spinocerebellar ataxia, spinal muscular atrophy, and amyotrophic lateral sclerosis (ALS). As used herein, the term "neurocognitive disease" refers to a condition involving decreased mental function (e.g., memory loss, decreased decision making ability, decreased learning ability, etc.) not related to a psychiatric disease. Neurocognitive diseases include, but are not limited to, AD, HD, traumatic brain injury (TBI), dementia (e.g., due to infections, such as HIV infection), Lewy body disease, prion disease, and frontotemporal degeneration. The term "neurodevelopmental disease" as used herein refers to a condition involving impairment in the growth and development of the brain and/or central nervous system. Such diseases can affect brain functions including emotions, learning ability, self-control, and memory. In some cases, the neurodevelopmental disease is the result of a genetic disorder (e.g., fragile X-syndrome, DS, Rett syndrome, ADHD, schizophrenia, schizotypal disorder, hypogonadotropic hypogonadal syndrome) or exposure to a neurotoxin (e.g., fetal alcohol spectrum disorder, Minamata disorder, and behavior disorders due to exposure to heavy metals, drugs, or environmental toxins (e.g., PCBs)). Additional neurodevelopmental diseases include, but are not limited to, autism, attention-deficit/hyperactivity disorder (ADHD), intellectual disability, TBI, motor disorder, and Tic disorders (e.g., Tourette's syndrome). Accordingly, in some cases, it can be noted that a particular disease can fit into more than one category of disease.

The presently disclosed modulator compounds include both activators and inhibitors. Activator or inhibitory activity of a particular modulator compound (or suspected modulator compound) can be determined by using methods known in the art in conjunction with the instant disclosure and/or described further hereinbelow (e.g., in Example 1). Thus, in some embodiments, the selection of modulator compound can be dependent upon the disease being treated. For example, in autism, it is believed that Rac1/Cdc42 is overly active. Thus, for a subject being treated for autism, the modulator compound administered can be, in some embodiments, an inhibitor of Cdc42, e.g., ZCL367.

However, as further described herein, some modulator compounds are dual functional modulators, having either activator or inhibitory activity depending upon whether or not Cdc42 is already activated by an upstream activating signal. For example, ZCL278 was previously shown to inhibit Cdc42 in the presence of activating upstream signaling compounds. See Friesland et al., Proc. Natl. Acad. Sci. USA, 2013, 110(4):1261-1266. However, surprisingly, as shown further hereinbelow, in the absence of upstream signaling compounds (e.g., epidermal growth factor (EGF) or bradykinin), ZCL278 acts as an activator of Cdc42. In some embodiments, the presently disclosed subject matter relates not to merely activating or inhibiting Cdc42, but to providing a compound that can restore Cdc42 homeostasis in situations involving complex dysregulation of Cdc42 and/or ITSN and/or their interactions, such as appears to be the case for AD, where it is believed that Cdc42 signaling and protein-protein interactions can sometimes be upregulated or downregulated depending upon disease stage and/or in a cell- and/or brain location-dependent fashion. Stated another way, it is believed that administration of a dual functional modulator compound can be useful to treat a disease involving complex/fluctuating Cdc42 dysregulation effectively and without resulting in overtreatments, since the same compound can act as an activator or an inhibitor within the same patient (but in separate cells or locations, as needed).

IV.B. Methods of Treating Alzheimer's Disease Using Cdc42 Modulators

In some embodiments, the presently disclosed subject matter provides a method of treating AD, wherein the method comprises administering to a subject in need of treatment, a compound that modulates Cdc42 (e.g., a compound of one of Formulas (I), (II), or (III) as described herein). In some embodiments, the compound of Formula (I) is a compound of Formula (Ia), (Ib), (Ic), and/or (Id). In some embodiments, the compound is a synthetic intermediate and/or metabolite of Formula (I) (e.g., a compound of Formula (Ie).

In some embodiments, the compound of Formula (II) is a compound of Formula (IIa), (IIb), and/or (IIc). In some embodiments, the compound of Formula (III) is a compound of Formula (IIIa) and/or (IIIb). In some embodiments, the modulator compound is a compound selected from a compound of Table 1 or a Table of Example 7, below. In some embodiments, the compound is selected from ZCL278, ZCL279, and ZCL367.

As described hereinabove, Cdc42 dysregulation in AD is believed to be complex. Signaling and protein-protein interactions can be upregulated or downregulated depending upon the stage of disease progression and/or in a cell- and/or brain location-dependent manner. In some embodiments, the subject can have early stage AD wherein it can be desirable to inhibit Cdc42 activity. Thus, in some embodiments, the subject in need of treatment is an early stage AD patient and the instantly disclosed method can comprise administering a modulator compound that can act as an activator (e.g., ZCL278 or ZCL279). In some embodiments, the subject in need of treatment is a later stage AD patient and the instantly disclosed method can comprise administering a modulator compound that can act as an inhibitor (e.g., ZCL278 or ZCL367). In some embodiments, the method can comprise administering a dual functional modulator compound (e.g., ZCL278), to restore Cdc42 homeostasis regardless of disease stage. In some embodiments, the method can involve simultaneously inhibiting a signaling pathway in certain areas of the hippocampus, but activation of a signaling pathway in another brain region via the administration of a dual functional modulator compound.

In some embodiments, the presently disclosed method can comprise performing one or more test(s) involving a subject in need of treatment for AD to determine the status of Cdc42 signaling in the subject and selecting an activator or inhibitor compound to administer to the subject based on the results of the test. In some embodiments, the test can involve one or more cognitive or imaging test used in the art to determine disease stage. In some embodiments, the test can involve one or more DNA, RNA, microRNA, or protein assay based on Rho GTPase in a body fluid, such as cerebrospinal fluid (CSF), serum or urine, which contains Cdc42, that is used in the art to determine disease stage. See e.g. Kumari et al., J. Egypt Natl. Canc. Inst., 2015, 27(2): 51-58; doi: 10.1016/j.jnci.2015.02.002. Thus, in some embodiments, a CSF, serum, or urine sample from the subject can be tested for the presence or absence of an upstream signaling compound.

By way of elaboration and not limitation, different types of drug candidates are provided in accordance with some embodiments of the presently disclosed subject matter: (1) inhibitors of the ITSN-Cdc42 signaling axis, such as ZCL367 and many others listed in the Tables provided elsewhere herein; (2) activators or agonists of ITSN-Cdc42 signaling when the upstream activation is absent, such as ZCL278 and many others listed in the Tables provided elsewhere herein, that become inhibitors or antagonists when there is upstream activation leading to the overactivation of ITSN-Cdc42 signaling; and (3) activators or agonists even in the presence of upstream of activating signal, such as ZCL279 and many others listed in the Tables provided elsewhere herein (stated another way, they enhance the activation).

In some embodiments, amyloid and tau imaging can be used in the selection of modulator compounds for application. By way of example and not limitation, if a subject shows significant amyloid and tau accumulation over a long period of time, indicative of overactivated microglia, ZCL278 and/or ZCL279 can be selected for use in treatment, such as to reduce the inflammation. In some embodiments, when a subject shows behavioral deficits, confusion, loss of interests and/or withdrawal from social activities as a major element, in addition to the typical loss of memory and learning functions, ZCL279 can be selected as a modulator because it enhances activity of daily living (ADL), memory, and learning as shown in the behavioral experiments shown elsewhere herein. When a subject shows contact avoidance, agitation, and/or psychosis, ZCL367 and/or ZCL278 can be chosen as a modulator, in accordance with data shown elsewhere herein.

When brain imaging shows the loss of spine or synaptic terminals in AD or pre-AD patients with mild cognitive impairment (MCI), ZCL278 can be chosen as a preventative modulator to stimulate the formation of synapses if the disease is as a result of dysregulation of ITSN-Cdc42 axis, or as an inhibitor of overactivation of ITSN-Cdc42 if the loss of spine is a result of overactivation of synaptic transmission or excitotoxicity.

When a test detects overactivation or overinhibition of the upstream elements of ITSN or Cdc42, for example, growth factors such as EGF, bradykinin as well as other guanine nucleotide exchange factors (GEFs) that are associated with the clinical disease manifestation, the presently disclosed modulators can be selected as treatments. When there is overactivation, ZCL278 and ZCL367 types would be the choice with ZCL367 as more potent inhibitor. When there is overinhibition, ZCL278 and ZCL279 types can be chosen as a modulator, with ZCL279 as a more powerful enhancer of activation even in the presence of activating signal. In some embodiments involving preventative therapy, a ZCL278 type can be chose as a modulator, as it is a mild modulator that can act as an agonist and antagonist depending on the cellular environment it is in. The toxicity profile is variable among ZCL278, ZCL279, and ZCL367 but generally favorable. See Example 3, below.

In some embodiments, the administration of the modulator compound provides reduction in the severity and/or frequency of one or more AD symptom(s). In some embodiments, administration provides reduction in the severity and/or frequency of one or more behavioral or cognitive symptom of AD, such as, but not limited, memory loss (e.g., short term memory loss or long term memory loss), confusion (e.g., about events, time, place, etc.), impaired judgment, disorientation, language/speech difficulties, unfounded suspicions, depression, social withdrawal, personality changes, trouble swallowing, and trouble walking. In some embodiments, administration of the modulator results in the elimination or a decrease in amyloid deposition, hyperphosphorylation of tau proteins, or the accumulation of pro-inflammatory microglia and/or an inhibition in actin dynamics.

IV.C. Methods of Treating Neurodegenerative, Neurocognitive, and/or Neurodevelopmental Diseases Using Compound of Formulas (I), (II), or (III).

In some embodiments, the presently disclosed subject matter provides a method of treating a neurodegenerative, neurocognitive and/or neurodevelopmental disease and/or disorder, wherein the method comprises administering to a subject in need thereof, a compound of one of Formulas (I), (II), or (III), as described herein above. In some embodiments, the disease is selected from the group including, but not limited to, AD, HD, PD, a motor neuron disease, prion disease, spinocerebellar ataxia, spinal muscular atrophy, ALS, TBI, dementia (e.g., due to an infection, such as an HIV infection), Lewy body disease, frontotemporal degeneration, fragile X-syndrome, DS, Rett syndrome, autism, intellectual disability, ADHD, schizophrenia, schizotypal disorder, hypogonadotropic hypogonadal syndrome, a motor disorder, a Tic disorder, fetal alcohol spectrum disorder, Minamata disorder, and a behavior disorder due to exposure to heavy metals, drugs, or an environmental toxins (e.g., PCBs)).

In some embodiments, the compound is a compound of Formula (I). In some embodiments, the compound is a compound of Formula (Ia), (Ib), (Ic), or (Id). In some embodiments, the compound is a compound of Formula (II). In some embodiments, the compound is a compound of Formula (IIa), (IIb), or (IIc). In some embodiments, the compound is a compound of Formula (III). In some embodiments, the compound is a compound of Formula (IIIa) or (IIIb). In some embodiments, the compound is a compound of Table 1, below. In some embodiments, the compound is selected from ZCL278, ZCL279, and ZCL367.

IV.D. Methods of Treating Alzheimer's Disease Using a Compound of Formulas (I), (II), or (III).

In some embodiments, the presently disclosed subject matter provides a method of treating Alzheimer's disease, wherein the method comprises administering to a subject in need thereof, a compound of one of Formulas (I), (II), or (III), as described herein above. In some embodiments, the compound is a compound of Formula (I). In some embodiments, the compound is a compound of Formula (Ia), (Ib), (Ic), or (Id). In some embodiments, the compound is a compound of Formula (II). In some embodiments, the compound is a compound of Formula (IIa), (IIb), or (IIc). In some embodiments, the compound is a compound of Formula (III). In some embodiments, the compound is a compound of Formula (IIIa) or (IIIb). In some embodiments, the compound is a compound of Table 1, below. In some embodiments, the compound is selected from ZCL278, ZCL279, and ZCL367.

In some embodiments, the administration of the compound provides reduction in the severity and/or frequency of one or more AD symptom(s). In some embodiments, administration provides reduction in the severity and/or frequency of one or more behavioral or cognitive symptom of AD, such as, but not limited, memory loss (e.g., short term memory loss or long term memory loss), confusion (e.g., about events, time, place, etc.), impaired judgment, disorientation, language/speech difficulties, unfounded suspicions, depression, social withdrawal, personality changes, trouble swallowing, and trouble walking. In some embodiments, administration of the compound results in the elimination or a decrease in amyloid deposition, hyperphosphorylation of tau proteins, or the accumulation of pro-inflammatory microglia and/or an inhibition in actin dynamics.

V. Formulations

As used herein, in some embodiments, the term "active compound" refers to a Cdc42 modulator compound, or a prodrug (such as but not limited to various esters and other derivatives that can form the Cdc42 modulator in vitro or in vivo), solvate (such as but not limited to a hydrate) and/or pharmaceutically acceptable salt thereof. In some embodiments, the term "active compound" refers to a compound of Formula (I), (II), or (III) (or one of their sub-formulas or those listed in Table 1 or one of the Tables of Example 7).

The active compound can be administered to the subject through any suitable approach. The amount and timing of active compound administered can, of course, be dependent on the subject being treated, the manner of administration, on the pharmacokinetic properties of the active compound being administered, and on the judgment of the prescribing physician. Thus, because of subject to subject variability, the dosages given below are a guideline and the physician can titrate doses of the compound to achieve the treatment that the physician considers appropriate for the subject. In considering the degree of treatment desired, the physician can balance a variety of factors such as age, gender, and weight of the subject, disease severity, as well as presence of other diseases. Pharmaceutical formulations can be prepared for any desired route of administration, including but not limited to oral, intravenous, or aerosol administration, as discussed in greater detail below.

The therapeutically effective dosage of any specific active compound, the use of which is within the scope of embodiments described herein, can vary somewhat from compound to compound, and subject to subject, and can depend upon the condition of the subject and the route of delivery. As a general proposition, a dosage from about 0.1 to about 200 mg/kg can have therapeutic efficacy, with all weights being calculated based upon the weight of the active compound, including the cases where a salt is employed. In some embodiments, the dosage can be the amount of compound needed to provide a serum concentration of the active compound of up to between about 1-5 µM or higher. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. In some embodiments, dosages can be from about 1 µmol/kg to about 50 µmol/kg, or, optionally, between about 22 µmol/kg and about 33 µmol/kg of the compound for intravenous or oral administration.

In accordance with the presently disclosed methods, pharmaceutically active compounds as described herein can be administered orally as a solid or as a liquid, or can be administered intramuscularly, intravenously or by inhalation as a solution, suspension, or emulsion. In some embodiments, the compounds or salts also can be administered by inhalation, intravenously, or intramuscularly as a liposomal suspension. When administered through inhalation the active compound or salt can be in the form of a plurality of solid particles or droplets having a particle size from about 0.5 to about 5 microns, and optionally from about 1 to about 2 microns.

The pharmaceutical formulations can comprise an active compound described herein or a pharmaceutically acceptable salt thereof, in any pharmaceutically acceptable carrier. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulation is placed in a vial designed for multi-dose use. The pharmaceutical formulations described herein can be lyophilized using techniques well known in the art.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed subject matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the subject matter described herein, there is provided an injectable, stable, sterile formulation comprising an active compound as described herein, or a salt thereof, in a unit dosage form in a sealed container. The compound or salt is provided in the form of a lyophilizate, which is capable of being reconstituted with a suitable pharmaceutically acceptable carrier to form a liquid formulation suitable for injection thereof into a subject. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulation can be placed in a small chamber and nebulized. Nebulization can be accomplished by compressed air or by ultrasonic energy to form a plurality of liquid droplets or solid particles comprising the compounds or salts. The liquid droplets or solid particles should have a particle size in the range of about 0.5 to about 10 microns, and optionally from about 0.5 to about 5 microns. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

When the pharmaceutical formulation suitable for administration as an aerosol is in the form of a liquid, the formulation can comprise a water-soluble active compound in a carrier that comprises water. A surfactant can be present, which lowers the surface tension of the formulation sufficiently to result in the formation of droplets within the desired size range when subjected to nebulization.

As indicated, both water-soluble and water-insoluble active compounds are provided. As used herein, the term "water-soluble" is meant to define any composition that is soluble in water in an amount of about 50 mg/mL, or greater. Also, as used herein, the term "water-insoluble" is meant to define any composition that has a solubility in water of less than about 20 mg/mL. In some embodiments, water-soluble compounds or salts can be desirable whereas in other embodiments water-insoluble compounds or salts likewise can be desirable.

The term "pharmaceutically acceptable salts" as used herein refers to those salts which are, within the scope of sound medical judgment, suitable for use in contact with subjects (e.g., human subjects) without undue toxicity, irritation, allergic response, and the like, commensurate with a reasonable benefit/risk ratio, and effective for their intended use, as well as the zwitterionic forms, where possible, of the compounds of the presently disclosed subject matter.

Thus, the term "salts" refers to the relatively non-toxic, inorganic and organic acid addition salts of compounds of the presently disclosed subject matter. These salts can be prepared in situ during the final isolation and purification of the compounds or by separately reacting the purified compound in its free base form with a suitable organic or inorganic acid and isolating the salt thus formed. In so far as the compounds of the presently disclosed subject matter are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the presently disclosed subject matter.

Pharmaceutically acceptable base addition salts are formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine.

The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the presently disclosed subject matter.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like.

Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66:1-19, which is incorporated herein by reference.

The subject treated in the presently disclosed subject matter in its many embodiments is desirably a human subject, although it is to be understood the methods described herein are effective with respect to all vertebrate species, which are intended to be included in the term "subject." The methods described herein are particularly useful in the treatment of warm-blooded vertebrates. Thus, the methods can be used as treatment for mammals and birds. In some embodiments, the methods can be used as a treatment for an animal model (e.g., a transgenic animal model) of a neurodegenerative disease. For example, in some embodiments, the efficacy of the presently disclosed compounds for use in treating a particular neurodegenerative disease (e.g, AD) can be assessed by treating an animal model of the disease. Accordingly, in some embodiments, the subject is a transgenic rodent, such as a transgenic or knockout mouse. In some embodiments, the subject is a 3×Tg-AD triple mutant transgenic mouse.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Compound Synthesis

Reagents were purchased from Sigma-Aldrich (Milwaukee, Wisconsin, United States of America), Acros (Morris Plains, New Jersey, United States of America), TCI America (Portland, Oregon, United States of America), or Alfa Aesar (Ward Hill, Massachusetts, United States of America) and used without further purification. AZA1 was purchased from EMD Millipore (Billerica, Massachusetts, United States of America). Nuclear magnetic resonance (NMR) spectra were obtained from a Bruker 400 spectrometer (Bruker Corporation, Billerica, Massachusetts, United States of America) in $CDCl_3$ or $DMSO-d_6$. Chemical shifts (6) are given in ppm relative to the signal for the deuterated solvent and are reported consecutively as position (dH), relative integral, multiplicity (s=singlet, d=doublet, t=triplet, q=quartet, dd=doublet of doublets, m=multiplet and br=broad), coupling constant (J/Hz) and assignment.

1.1. Synthesis of ZCL278 and its analogs: Equimolar (5-7 mmol) NaOH and substituted phenol was dissolved in 15 mL water followed by the addition of equimolar (5-7 mmol) NaOH and bromoacetic acid in 15 mL water. The solution was refluxed for 4-8 h, allowed to cool to RT, acidified with concentrated $H_2SO_4$ and extracted with ethyl acetate (3×15 mL). The organic layer was extracted with saturated $NaHCO_3$ (3×20 mL). The aqueous layer was acidified with con. HCl followed by extraction with ethyl acetate (3×15 mL), dried over anhydrous $MgSO_4$ and solvent removed under vacuum resulting in the substituted phenoxyacetic acid (e.g., compound id of Scheme 1, above). A solution of the phenoxyacetic acid in 20 mL $SOCl_2$ and a drop of dimethyl formamide was refluxed for 3-6 h then excess $SOCl_2$ removed by distillation to give the crude acyl chloride (e.g., compound 1 of Scheme 1, above). A solution of acyl chloride in 15 mL anhydrous acetone was added to a solution of sodium isothiocyanate in ice cold anhydrous acetone and stirred at RT for 3 h to give the acyl isothiocyanate followed by the addition of 4-amino-N-(4,6-dimethyl-2-pyrimidinyl)benzenesulfonamide. After stirring overnight, the solution was poured onto ice and recrystalized in dichloromethane and methanol to give the thiourea product.

Exemplary Compounds:
4-(3-(2-(4-bromo-2-chloro-phenoxy)-acetyl)-thioureido)-N-(4,6-dimethylpyrimidin-2-yl)-benzenesulfonamide (ZCL278).

Prepared as described in U.S. Patent Application Publication No. 2014/0194451, incorporated herein by reference in its entirety.

4-(3-(2-(4-bromo-phenoxy)-acetyl)-thioureido)-N-(4,6-dimethylpyrimidiin-2-yl)-benzenesulfonamide (BA1-12) $C_{21}H_{20}BrN_5O_4S_2$ (Bromo):

4-Bromophenol (1 g, 5.8 mmol) to afford (4-bromophenoxy)acetic acid (1.27, 95%) as a white solid. $^1H$ NMR (400 MHz, $CDCl_3$) δ 7.41 (d, J=11.1 Hz, 2H), 6.81 (d, J=9.1 Hz, 2H), 4.67 (s, 2H), (4-bromophenoxy)acetic acid (1.5 g, 6.5 mmol) to afford the title thiourea (0.06 g, 2%) as a white solid. $^1H$ NMR (400 MHz, $DMSO-d_6$) δ 12.30 (s, 1H), 11.76 (s, 1H), 8.04 (d, J=8.7 Hz, 2H), 7.90 (d, J=8.7 Hz, 2H), 7.53 (d, J=9.04 Hz, 2H), 7.00 (d, J=9.08 Hz, 2H), 6.81 (s, 1H), 4.95 (s, 2H), 2.31 (1, 6H). $^{13}C$ NMR ($DMSO-d_6$) δ 178.3, 169.6, 157.0, 132.2, 128.6, 123.5, 116.8, 112.7, 66.1.

4-(3-(2-(4-methyl-phenoxy)-acetyl)-thioureido)-N-(4,6-dimethylpyrimidin-2-yl)-benzenesulfonamide (BA1-28) $C_{22}H_{23}N_5O_4S_2$ (Methyl): 4-methylhphenol (1 g, 10 mmol) to afford (4-methylphenoxy)acetic acid (1.2 g, 74%) as a white solid. $^1H$ NMR (400 MHz, $CDCl_3$) δ 7.10 (d, J=8.2 Hz, 2H), 6.85 (d, J=8.6 Hz, 2H), 4.7 (s, 2H), 2.24 (s, 3H), (4-methylphenoxy)acetic acid (1.2 g, 7.3 mmol) to afford the title compound (0.22 g, 6.5%) as a yellow solid. $^1H$ NMR (400 MHz, $DMSO-d_6$) δ 12.30 (s, 1H), 11.65 (s, 1H), 7.99 (d, J=8.7 Hz, 2H), 7.86 (d, J=8.7 Hz, 2H), 7.10 (d, J=8.2 Hz, 2H), 6.85 (d, J=8.6 Hz, 2H), 6.76 (s, 1H), 4.83, (s, 2H), 2.24 (s, 3H). $^{13}C$ NMR ($DMSO-d_6$) δ 178.4, 170.1, 155.5, 130.0, 129.9, 128.6, 123.5, 114.3, 66.1, 20.0.

4-(3-(2-(4-ethyl-phenoxy)-acetyl)-thioureido)-N-(4,6-dimethylpyimidin-2-yl)-benzenesulfonamide (BA1-20) $C_{23}H_{25}N_5O_4S_2$ (Ethyl): 4-ethylphenol (1.2 g, 10 mmol) to afford (4-ethylphenoxy)acetic acid (1.3 g, 74%) as a light brown solid. $^1H$ NMR (400 MHz, $CDCl_3$) δ 7.13 (d, J=8.7 Hz, 2H), 6.85 (d, J=8.7 Hz, 2H), 4.7 (s, 2H), 2.6 (q, J=7.6 Hz, 2H), 1.2 (t, J=7.6 Hz, 3H), (4-ethylphenoxy)acetic acid (1.3 g, 7.4 mmol) to afford the title compound (0.31 g, 8.3%) as a light yellow solid. $^1H$ NMR (400 MHz, $DMSO-d_6$) δ 12.29 (s, 1H), 11.66 (s, 1H), 7.99 (d, j=8.8 Hz, 2H), 7.85 (d, J=8.7 Hz, 2H), 7.13 (d, J=8.7 Hz, 2H), 6.86 (d, J=8.7 Hz, 2H), 6.75 (s, 1H), 4.84 (s, 2H), 2.55 (t, J=7.6 Hz, 2H), 2.25 (s, 6H), 1.15 (t, J=7.6 Hz, 3H). $^{13}C$ NMR ($DMSO-d_6$) δ 178.4, 170.1, 156.0, 155.6, 141.1, 138.1, 136.6, 128.7, 128.7, 123.5, 114.3, 66.0, 27.2, 22.7, 15.9.

4-(3-(2-(4-methoxy-phenoxy)-acetyl)-thioureido)-N-(4,6-dimethylpyrimidin-2-yl)-benzenesulfonamide (BA1-46) $C_{22}H_{23}N_5O_5S_2$ (Methoxy): 4-methoxyphenol (1 g, 8 mmol) to afford (4-methoxyphenoxy)acetic acid (0.6 g, 46%) as a brown solid. $^1H$ NMR (400 MHz, $CDCl_3$) δ 8.17 (br, 1H), 6.87 (m, 4H), 4.63 (s, 2H), 3.77 (s, 3H), (4-methoxyphenoxy)acetic acid (0.6 g, 3.2 mmol) to afford the title compound (0.1 g, 6.3%) as a white solid. $^1H$ NMR (400 MHz, $DMSO-d_6$) δ 12.31, (s, 1H), 11.63 (s, 1H), 8.00 (d, J=8.6 Hz, 2H), 7.86 (d, J=8.4 Hz, 2H), 6.91-6.87 (m, 4H), 6.76 (s, 1H), 4.81 (s, 2H), 3.71 (s, 3H), 2.26 (s, 6H). $^{13}C$ NMR ($DMSO-d_6$) δ 178.9, 170.7, 154.4, 152.1, 129.1, 124.0, 116.0, 115.1, 67.1.

4-(3-(2-(4-ethoxy-phenoxy)-acetyl)-thioureido)-N-(4,6-dimethylpyrimidin-2-yl)-benzenesulfonamide (BA1-47) $C_{23}H_{25}N_5O_5S_2$ (Ethoxy):

4-ethylphenol (1 g, 7.2 mmol) to afford (4-ethoxyphenoxy)acetic acid (0.66 g, 48%) as a white solid. $^1H$ NMR (400 MHz, $CDCl_3$) 6.85 (m, 4H), 4.62 (s, 2H), 3.98 (dd, J=7

Hz, 2H), 1.39 (t, J=6.96 Hz, 3H), (4-ethoxyphenoxy)acetic acid (0.7 g, 3.3 mmol) to afford the title compound (0.04 g, 2.5%) as a yellow solid. $^1$H NMR (400 MHz, DMSO-d$_6$) δ 12.31 (s, 1H), 11.62 (s, 1H), 8.00 (d, J=8.7 Hz, 2H), 7.86 (d, J=8.6 Hz, 2H) 6.90-6.85 (m, 4H), 6.77 (s, 1H), 4.80 (s, 2H), 3.96 (q, J=7 Hz, 4H), 2.26 (s, 6H), 1.29 (t, J=7 Hz, 3H). $^{13}$C NMR (DMSO-d$_6$) δ 178.4, 170.2, 153.1, 151.5, 128.6, 123.5, 115.4, 115.2, 66.6, 63.3, 14.7.

1.2. Synthesis of ZCL279 Chlorosulfuric acid (120 mmol) was added dropwise to a solution of dibenzofuran (240 mmol) in thionyl chloride (~100 mL) and refluxed overnight. After cooling to room temperature, the solution was poured onto crushed ice and the precipitate was filtered and dried. A solution of the crude product was prepared in ethanol (~150 mL) and 2-aminophenol was added and stirred at room temperature for 24 hours. The product was recrystallized from absolute ethanol. $N^2,N^8$-bis(2-hydroxyphenyl)dibenzo[b,d]furan-2,8-disulfonamide. $^1$H NMR (400 MHz, DMSO-d$_6$) δ 9.52 (s, 2H), 9.31 (s, 2H), 8.69 (s, 2H), 7.94 (m, 4H), 7.18 (m, 2H), 6.94 (m, 2H), 6.77 (m, 4H).

1.3. Synthesis of ZCL367 and its analogs: Equimolar aldehyde derivative (~7 mmol) was added to an ethanol solution (25 mL) of substituted hydrazide (~7 mmol) and the solution refluxed for 6 h. After cooling to room temperature, the precipitated solid was filtered, washed with ethanol and recrystallized from absolute ethanol to give the title acyl hydrazones.

Exemplary Compounds:

(E)-3,5-dihydroxy-N'-(2-hydroxybenzylidene)benzohydrazide (ZCL367) $C_{14}H_{12}N_2O_4$:

Salicylaldehyde was added to an ethanol solution of 3,5-diphenolbenzoichydrazide to give the title product. $^1$H NMR (400 MHz, DMSO-d$_6$) δ 11.97 (s, 1H), 11.37 (s, 1H), 9.62 (s, 2H), 8.63 (s, 1H), 7.50 (m, 1H), 7.30 (m, 1H), 6.93 (m, 2H), 6.78 (d, J=2.1 Hz, 2H), 6.45 (t, J=2.1 Hz, 1H).

(E)-N'-(2-hydroxybenzylidene)furan-2-carbohydrazide (BA2-28) $C_{12}H_{10}N_2O_3$:

Salicylaldehyde was added to an ethanol solution of furan-2-carbohydrazide to give the title product. $^1$H NMR (400 MHz, DMSO-d$_6$) δ 12.11 (s, 1H), 11.11 (s, 1H), 8.62 (s, 1H), 7.93 (s, 1H), 7.46 (m, 3H), 6.97 (t, J=8.3 Hz, 2H), 6.69 (dd, J=1.7 Hz, 1H).

(E)-ethyl 2-(2-hydroxybenzylidene)hydrazinecarboxylate (BA2-29) $C_{10}H_{12}N_2O_3$:

Salicylaldehyde was added to an ethanol solution of ethyl-hydrazinecarboxylate to give the title product. $^1$H NMR (400 MHz, DMSO-d$_6$) δ 11.26 (s, 1H), 10.83 (s, 1H), 8.21 (s, 1H), 7.48 (m, 1H), 7.25 (m, 1H), 6.87 (m, 2H), 4.16 (q, J=7.0 Hz, 2H), 1.25 (t, J=7.1 Hz, 3H).

(E)-benzyl 2-(2-hydroxybenzylidene)hydrazinecarboxylate (BA2-32) $C_{15}H_{14}N_2O_3$:

Salicylaldehyde was added to an ethanol solution of benzyl-hydrazinecarboxylate to give the title product. 1H NMR (400 MHz, DMSO-d$_6$) δ 11.44 (s, 1H), 10.81 (s, 1H), 8.25 (s, 1H), 7.47 (m, 1H), 7.38 (m, 5H), 7.25 (m, 1H), 6.88 (m, 2H), 5.19 (s, 2H).

(E)-2-(2-hydroxybenzylidene)-N-methylhydrazinecarbothioamide (BA2-34) $C_9H_{11}N_3OS$:

Salicylaldehyde was added to an ethanol solution of N-methylhydrazinecarbothioamide to give the title product. $^1$H NMR (400 MHz, DMSO-d$_6$) δ 11.42 (s, 1H), 9.91 (s, 1H), 8.43 (t, J=4.6 Hz, 1H), 8.36 (s, 1H), 7.93 (m, 1H), 7.21 (m, 1H), 6.85 (m, 2H), 3.00 (d, J=4.6 Hz, 3H).

Compound structures are shown below in Table 1.

TABLE 1

Compound Structures.

| Compound | Structure |
|---|---|
| ZCL278 | 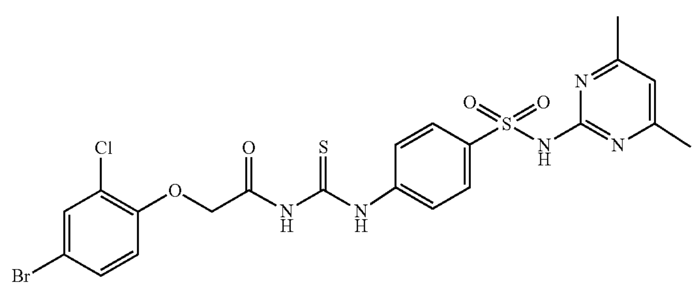 [SMILES: Cc1cc(C)nc(NS(=O)(=O)c2ccc(NC(=S)NC(=O)COc3ccc(Br)cc3Cl)cc2)n1] |
| BA1-12 | 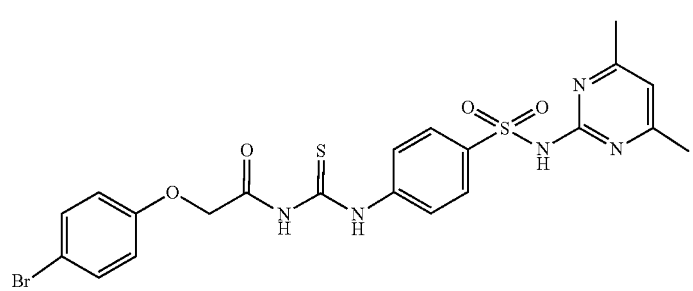 [SMILES: Cc1cc(C)nc(NS(=O)(=O)c2ccc(NC(=S)NC(=O)COc3ccc(Br)cc3)cc2)n1] |

TABLE 1-continued

Compound Structures.

| Compound | Structure |
|---|---|
| BA1-20 | 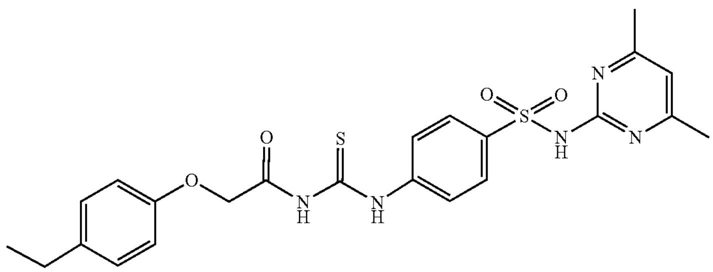 [SMILES: CCc1ccc(OCC(=O)NC(=S)Nc2ccc(S(=O)(=O)Nc3nc(C)cc(C)n3)cc2)cc1] |
| BA1-28 | 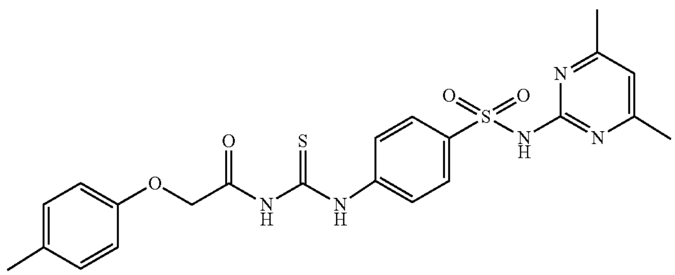 |
| BA-46 | 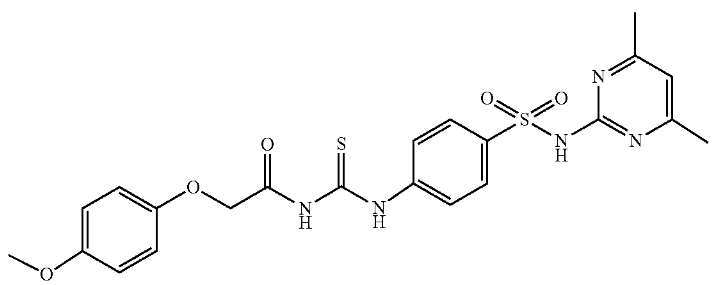 |
| BA-47 | 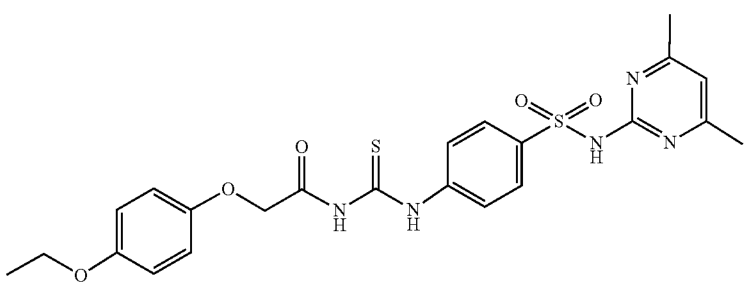 [SMILES: CCOc1ccc(OCC(=O)NC(=S)Nc2ccc(S(=O)(=O)Nc3nc(C)cc(C)n3)cc2)cc1] |
| ZCL279 | 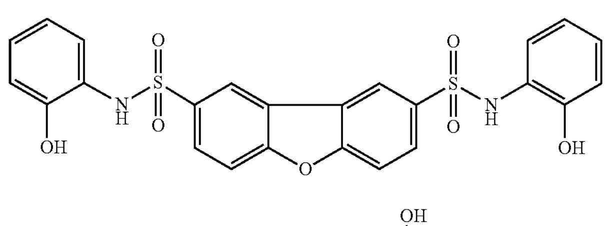 |
| ZCL367 | 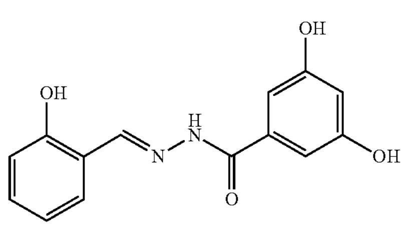 [SMILES: O=C(N/N=C/c1ccccc1O)c1cc(O)cc(O)c1] |

TABLE 1-continued

Compound Structures.

| Compound | Structure |
|---|---|
| BA2-28 | 2-hydroxybenzylidene furan-2-carbohydrazide |
| BA2-29 | ethyl 2-(2-hydroxybenzylidene)hydrazine-1-carboxylate |
| BA2-32 | benzyl 2-(2-hydroxybenzylidene)hydrazine-1-carboxylate |
| BA2-34 | 2-(2-hydroxybenzylidene)-N-methylhydrazine-1-carbothioamide |

Example 2

In Vitro Activity Assays

Rho-GEF $IC_{50}$ Assay: Rho-GEF assay (Cytoskeleton Inc., Denver, Colorado, United States of America) was conducted per manufacturer's instructions ($\lambda_{ex}$=360 nm, $\lambda_{em}$=460 nm). Briefly, a solution (50 μL) of purified Rho GTPase (1 μM) and mant-GTP (1.5 μM) with or without compound (0.001-500 μM) was prepared and the absorbance monitored for 10-30 min to obtain the background/baseline. The addition of purified GEF/DH domain (0.08-0.2 μM) was carried out simultaneously and the absorbance was recorded for 30-45 min. The linear slope following the addition of the GEF was calculated and expressed as percentage of the control and plotted on an $IC_{50}$ curve. Both ZCL278 ($IC_{50}$=7.52 μM) and ZCL367 ($IC_{50}$=0.098 μM) inhibit GEF/DH domain-mediated mant-GTP binding/Cdc42 activation. ZCL367 is more potent against Cdc42 than RhoA ($IC_{50}$=29.7 μM) and Rac1 ($IC_{50}$=0.19 μM). ZCL278 does not appear to inhibit mant-GTP binding to Rac1 ($IC_{50}$≥500 μM) and RhoA ($IC_{50}$≥500 μM).

Cdc42 (1 μM) was incubated with mant-GTP (1.5 μM) and varying concentrations of ZCL278, ZCL279, or ZCL367 (5-500 μM). Fluorescent readings were taken every minute for 10 m to acquire the baseline. The GEF/DH domain (0.08-0.2 μM) was added followed by readings taken every minute for another 30 m. The linear phase was calculated from within the time period of 12-22 m. Cdc42 (1 μM) was incubated with mant-GTP (1.5 μM) and varying concentrations of ZCL278, ZCL279, or ZCL367 (5-500 μM). Fluorescent readings were taken every minute for 30 m to monitor the binding of mant-GTP in the absence of GEF/DH domain. ZCL278 activates Cdc42 in the absence of GEF domain. With GEF ZCL278 acts as an inhibitor. In contrast, ZCL279 activates Cdc42 in the presence of GEF domain, but has no effect in the absence of GEF domain. ZCL367 has no effect in the absence of GEF domain, but acts as an inhibitor in the presence of GEF domain.

G-LISA: G-LISA is an ELISA-based assay that allows a quantitative determination of the levels of GTP-bound (active) Cdc42 in cellular lysates. Swiss 3T3 cells (~50% confluent) were starved for 24h then treated with ZCL278 (50 μM) for 0, 5, 10, 15, 30, or 60 m. Cells were lysed and G-LISA conducted according to Cytoskeleton G-LISA protocol. Briefly, ~300 μL of lysis buffer was added, cells were scraped, transferred to a centrifuge tube, and centrifuged at 0° C. for 1 min at 13,200 rpm. Samples were flash frozen in liquid nitrogen. Approximately 15 sg protein was loaded into duplicate wells for G-LISA. Absorbance was measured at 490 nm. ZCL278 activates Cdc42 (with activity peaking after about 15 min and with another peak about 60 min) and inhibits Rac1 in serum-starved Swiss 3T3 cells.

Immunofluorescence: Serum-starved Swiss 3T3 cells were pretreated with compound for 2 h before the addition of bradykinin (100 ng/mL) for 20 min. Cells were fixed in 4% paraformaldehyde for 15 min at RT and stored in PBS. Fixed cells were treated with 0.5% Triton for 30 min at RT, 100 mM Glycine 30 min at RT, and 10% BSA for 30 min at 37° C. Primary antibody for GM130 (1:1000, BD Biosciences, Franklin Lakes, New Jersey, United States of America) was used to probe for 1 h at RT followed by CY3-conjugated secondary antibody (1:1000) for 1 h at RT in the dark. Actin was stained with fluorescein-conjugated phalloidin (1:300). Hoechst (1:2500) was used to stain the nuclei. Coverslips were mounted onto slides using antifade medium from Life Technologies (Carlsbad, California, United States of America). Images were taken with a Zeiss Axiovert S100 microscope (Carl Zeiss; Thornwood, New York, United States of America).

Treatment with either ZCL278 or ZCL279 caused significant changes to cell morphology after 4 h of treatment, and even more drastic changes after six hours. ZCL278 treatment resulted in an increase in ramification. ZCL279 treatment resulted in a reduction in cell body size and formation of elongated processes. ZCL367 treatment had no effects on cell morphology. Both ZCL278 and ZCL367 inhibit bradykinin-mediated activation in the Swiss 3T3 cells.

Example 3

ZCL278, ZCL279 and ZCL367 Solubility and Toxicity

ZCL278, ZCL279, and ZCL367 were all tested for solubility in the 5 FDA approved solvents to be used in humans. They showed variable solubility profiles, but all were completely soluble in DM19. Results are shown below in Tables 2-4. Ratio refers to the optical density of the solution comprising the modulator compound/the optical density of the carder/solvent alone.

TABLE 2

ZCL278 Solubility Profile

| RT-3 h | Solvent | ZCL278 | Ratio |
|---|---|---|---|
| 1,2-Propanediol, 40% | 0.039 | 0.123 | 3.1538462 |
| Polyethylene Glycol$_{300}$ (PEG-300), 30% | 0.04 | 0.091 | 2.275 |
| Tween 80, 0.4% | 0.04 | 0.069 | 1.725 |
| Pluronic F-68 | 0.04 | 0.107 | 2.675 |
| Sesame Oil | 0.043 | 0.06 | 1.3953488 |
| Sterile Water | 0.038 | 0.084 | 2.2105263 |
| dPBS | 0.039 | 0.07 | 1.7948718 |
| Dimethyl Sulfoxide (DMSO) | 0.042 | 0.047 | 1.1190476 |

TABLE 3

ZCL279 Solubility Profile

| 37° C., 1 hour | ZCL279 | Solvent | Ratio |
|---|---|---|---|
| Sterile Water | 0.234 | 0.038 | 6.157895 |
| Polyethylene Glycol$_{300}$ (PEG-300), 30% | 0.158 | 0.042 | 3.761905 |
| dPBS | 0.15 | 0.039 | 3.846154 |
| Tween-80, 0.4% | 0.118 | 0.038 | 3.105263 |
| Pluronic F-68, 10% | 0.104 | 0.039 | 2.666667 |
| 1,2-Propanediol, 40% | 0.092 | 0.039 | 2.358974 |
| Sesame Oil | 0.088 | 0.047 | 1.87234 |
| Dimethyl Sulfoxide (DMSO) | 0.045 | 0.042 | 1.071429 |

TABLE 4

ZCL367 Solubility Profile

| RT, 10 minutes | ZCL367 | Solvent | Ratio |
|---|---|---|---|
| Sterile Water | 0.198 | 0.038 | 5.210526 |
| Tween-80, 0.4% | 0.136 | 0.038 | 3.578947 |
| Sesame Oil | 0.116 | 0.044 | 2.636364 |
| dPBS | 0.113 | 0.038 | 2.973684 |
| 1,2-Propanediol, 40% | 0.104 | 0.039 | 2.666667 |
| Polyethylene Glycol$_{300}$ (PEG-300), 30% | 0.091 | 0.039 | 2.333333 |
| Pluronic F-68, 10% | 0.079 | 0.039 | 2.025641 |
| Dimethyl Sulfoxide (DMSO) | 0.044 | 0.042 | 1.047619 |

Initial studies also indicated that the modulator compounds affected Cdc42 signaling in the brain lysates. Initial pharmacodynamics and pharmacokinetic studies also showed that they were detectable within 15 minutes after injection into C57BL/6 mice and were still detectable 24 hours later in mouse plasma.

ZCL 278 Toxicity Experiment: Individual C57BL/6 mice of 4-6 months of age from Jackson Laboratory (Bar Harbor, Maine, United States of America) were submitted to ZCL278 treatment for 5 minutes, 30 minutes, 2 hours and 24 hours. The dosage of ZCL278 for each mouse was 0.8 mg/g body weight delivered via intraperitoneal (I.P.) injection of a 15 mg/ml solution of ZCL278 was dissolved in the sesame oil (10% DMSO). All mice were survived and were sacrificed at the designated treatment time. Plasma, liver, kidney and brain tissues were collected from each mouse for examination and no gross anatomic toxicity were noted.

ZCL 279 Toxicity Experiment: Individual C57BL/6 mice of 4-6 months of age from Jackson Laboratory (Bar Harbor, Maine, United States of America) were submitted to ZCL279 treatment for 5 minutes, 30 minutes, 2 hours and 24 hours. The dosage of ZCL279 for each mouse was 0.6 mg/g body weight delivered via intraperitoneal (I.P.) injection of a 15 mg/ml solution of ZCL279 was dissolved in the sesame oil (10% DMSO). With the exception of 24-hour treatment mouse which died, all mice survived were and sacrificed at the designated treatment time. Plasma, liver, kidney and brain tissues were collected from each mouse for examination and no gross anatomic toxicity were noted.

ZCL367 Toxicity Experiment: Individual C57BL/6 mice of 4-6 months of age from Jackson Laboratory (Bar Harbor, Maine, United States of America) were submitted to ZCL367 treatment for 1 hour or 2 weeks. The dosage of ZCL367 for each time period was 0.4 mg/g body weight or 0.8 mg/g body weight, delivered via I.P. injection. All mice survived at the end of experiment. Mice were sacrificed after end of 1 hour or 2 weeks. Liver, kidney, spleen and spleen were collected from each mouse for examination and no gross anatomic toxicity were noted.

Long-term Survival. Groups of 10 mice were treated with one injection of ZCL278 (up to 0.8 mg/g), ZCL279 (up to 0.6 mg/g), or ZCL367 (up to 1.6 mg/g) to examine potential lethal dosage (the maximal dosage tested when no mice died). While no mice died for ZCL278 and ZCL 279 groups at the end of 3 month, one (day 20) out of four mice died in 1 month in the ZCL367 group when ZCL367 dosage reached 1.6 mg/g. Table 5, below, also shows the longest duration tested for each group where no mice died when dosages were 0.8 mg/g for ZCL278 and ZCL367 and 0.6 mg/g for ZCL279. Durations longer than 3 months have not been tested. As a reference, working dosage for the behavioral assessment described below used 20 ug/g for injection, 30 times lower than the highest dosage of 0.8 mg/g tested in the long-term survival experiment.

TABLE 5

Survival Profile for ZCL278, ZCL279, and ZCL367 in Mice at Lethal Dosage.

| Compound | Lethal Dosage (mg/g) | Longest Dosing Duration (months) |
|---|---|---|
| ZCL278 | 0.8 | 3 |
| ZCL279 | 0.6 | 3 |
| ZCL367 | 0.8 | 2 |

Example 4

Behavioral Assessment in AD Mouse Model after ITSN-Cdc42 Modulator Treatment Six-month-old C57/BL6 (WT) and 3×Tg-AD mice with an average weight of 24 g from Jackson Laboratory (Bar Harbor, Maine, United States of America) were used. The 3×Tg-AD mice in hybrid 129/C57BL/6 background contain two mutant human transgenes, hAPP harboring Swedish mutation ($hAPP_{swe}$) and mutant htau ($htau_{301L}$) under a neuron-specific promoter, and also contain the knock-in mutant presenilin 1 ($PS1_{M146V}$). See Oddo et al. (2003) Neuron 39:409-421). 3×Tg-AD mice were received from Jackson Laboratory as Psen1 B6:129-Psen1<tmMpm>Tg (APPSwetauP301L)1Lfa/J and the wild type control as SF2: (B6129SF1/J+p+Tyr-c+Mgf-SIJ)F2. All mice were subjected to two weeks of training for familiarizing behavioral test procedures. Subsequently, mice were assayed to establish a baseline of behavior tests before ZCL compound treatment. Then, mice were separated into three treatment groups (Control, ZCL278 and ZCL279). Both ZCL278 and ZCL279 were dissolved in sesame oil with 5% DMSO and each treatment was administrated via an intraperitoneal injection. All treatment groups of mice were treated once a week. Control group was treated with 130 µl 5% DMSO in sesame oil. ZCL278 and ZCL279 groups were treated with 20 µg/g ZCL 278 or ZCL 279 in sesame oil (5% DMSO). On the day following drug treatment, all mice were subjected to a burrowing test, nesting test and contact avoidance evaluations. On the $4^{th}$ week of experiment, selected female mice from each group were submitted to Morris water maze test and eye blink test.

Burrowing test: At least 2.5 hours before the start of the dark cycle (4:30 pm), mice from each selected treatment group were housed in individual cages. Each cage contained a plastic tube containing 200 g of food pellets (their normal diet). The tube was made from a section of plastic downpipe, 20 cm long, 6.8 cm diameter, raised 3 cm at one end by two machine screws to minimize pellet loss due to any non-burrowing movements of the mouse. The other end was sealed with a plastic cap. After 2 hours, the food left in the tube was measured.

Nesting test: Similar to the burrowing test, 2.5 hours before the start of the dark cycle, mice were housed singly in cages containing one 5 cm square of pressed cotton ('Nestlet', which the mice normally received as part of their environmental enrichment) with which to make a nest. The condition of each nest was assessed after 2 hours, according to a four-point scale as follows:
1=Nestlet not noticeably touched (>90% intact).
2=Nestlet partially torn up (70-90% remaining intact).
3=Mostly shredded but often no identifiable nest site (<50% remaining intact).
4=An identifiable nest (<10% remaining intact).

Contact Avoidance: Initially, all mice demonstrated a certain level of resistance toward handling on drug treatment day. However, WT (C57/BL6) mice quickly adapted to the treatment schedule and displayed significantly less hostility toward the handler compared to age-matched 3×Tg-AD mice. As an unbalanced emotional state has been reported in human AD patients, this difference was investigated further, in individually housed mice. The severity of contact avoidance was evaluated on the drug treatment day by the handler, according to a four-point scale as follows:
1=Calm
2=Responsive
3=Restless
4=Agitative
5=Aggressive Morris water maze test: A circular aluminum tank (1.5 m diameter) painted white and filled with water was maintained at 26° C.-29° C. The maze is located in a room containing several simple visual, extra-maze cues. To reduce stress, mice were placed on the platform in both the hidden and cued versions of the task for 10 s prior to the first training trial.

Mice were trained to swim to a 14 cm diameter circular clear Plexiglas platform submerged 1.5 cm beneath the surface of the water and invisible to the mice while swimming. The platform location was selected randomly for each mouse but was kept constant for each individual mouse throughout training. On each trial, the mouse was placed into the tank at one of four designated start points in a pseudorandom order. Mice were allowed to find and escape onto the submerged platform. If a mouse failed to find the platform within 60 s, it was manually guided to the platform and allowed to remain there for 10 s. After this, each mouse was placed into a holding cage under a warming lamp for 25 s until the start of the next trial. Retention of the spatial training was assessed at 1.5 hr and again at 24 hr after the last training trial. Both probe trials consisted of a 60 s free swim in the pool without the platform. Mice were monitored by a camera mounted in the ceiling directly above the pool, and all trials were stored on videotape for subsequent analysis.

Eye blinking test: Eyeblink classical conditioning (ECC) behavior testing was performed based on a method described previously. See Rufer et al., PLoS One, 2012, 7(10):e47499; and Thomas & Tran, Hippocampus, 2012, 22:619-630. Briefly, the day after ZCL compound treatment, two stainless steel recording electrodes (3T, Medwire, Mount Vernon, New York, United States of America) were implanted in the left orbicularis oculi muscle in all mice, and a bipolar stimulating electrode adjacent to the left eye. Mice were placed in a modified operant box containing a light and fan (55 decibel (dB)) after 48 hour recovery. Mice could move freely with an animal's EMG wires were plugged into a commutator. The operant box was connected to a computer equipped with proprietary stimuli (conditioned stimulus (CS) and unconditioned stimulus (US)). Thirty mice were tested for short-delay ECC. Data collected from each mouse was pre-screened by using established criteria in rodent ECC. See Skelton, Behav. Neuroscience, 1988, 102:586-590; and Tran et al., Dev. Psychibiol., 2007, 49:589-605.

Six sessions were carried out with 100 trials per session. During each trial, a tone CS was presented first and following a delay, a shock US was delivered. On every 10th trial, the tone CS was presented by itself to test for learning of the CR. In total, there were 100 trials per session. Mice received two sessions per day over three consecutive days and six sessions total.

Figure 1A:
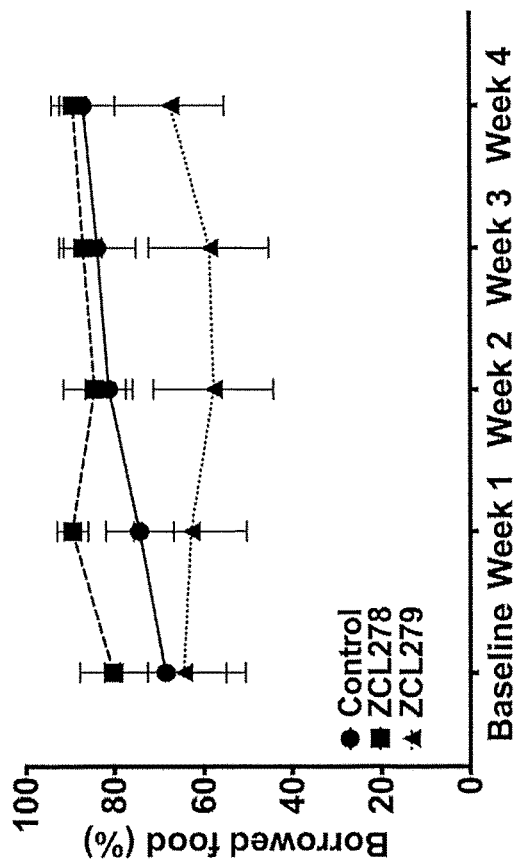
FIG. 1A is a graph showing the effects of the administration of exemplary cell division control protein 42 homolog (Cdc42) modulator compounds, ZCL278 (squares) or ZCL279 (triangles), on food burrowing behavior (measured as a percentage (%) of food burrowed outside a burrowing tube filled with 200 grams of food pellets) in wild-type mice over the course of four weeks of treatment. For comparison, data from mice treated with a vehicle (sesame oil with 5% dimethyl sulfoxide (DMSO) is shown as a control (circles). "Baseline" on the x-axis refers to baseline behavior (i.e., prior to compound administration). N=10 per group. Values represent mean±sem.

Results: Compared to WT mice, transgenic mice displayed reduced instinctual behaviors like food burrowing (see FIGS. 1A and 1B) and nesting.

Figure 2B:
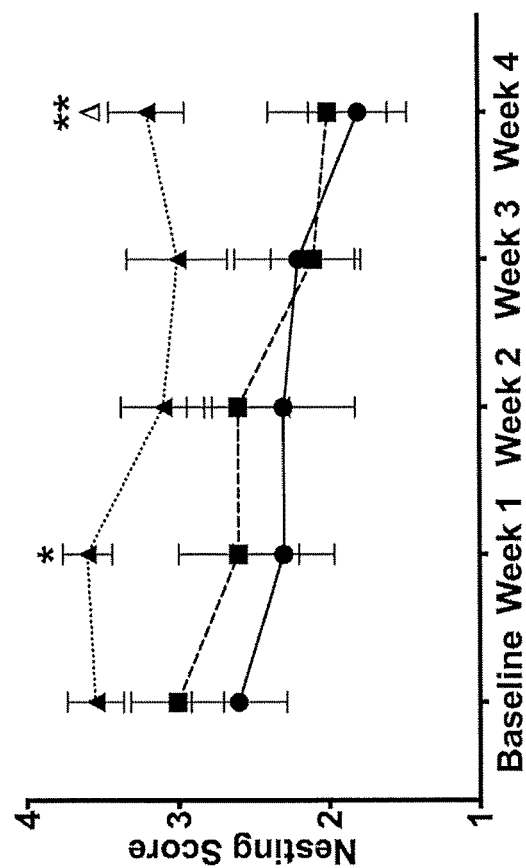
FIG. 2B is a graph showing the effects of the administration of exemplary cell division control protein 42 homolog (Cdc42) modulator compounds, i.e., ZCL278 (squares) or ZCL279 (triangles), on nesting behavior (measured on a relative scale from 1 to 4) in triple transgenic mice of a mouse model of Alzheimer's disease (3×Tg-AD). Behavior was followed over the course of 4 weeks. For comparison, data from mice treated with vehicle (sesame oil with 5 percent (%) dimethyl sulfoxide (DMSO) is shown as a control (circles). "Baseline" on the x-axis refers to baseline behavior (i.e., prior to compound administration). N=10 per group. Values represent mean±sem. *$p<0.05$, **$p<0.001$, relative to control. $\Delta p<0.05$, relative to ZCL278.
Figure 2A:
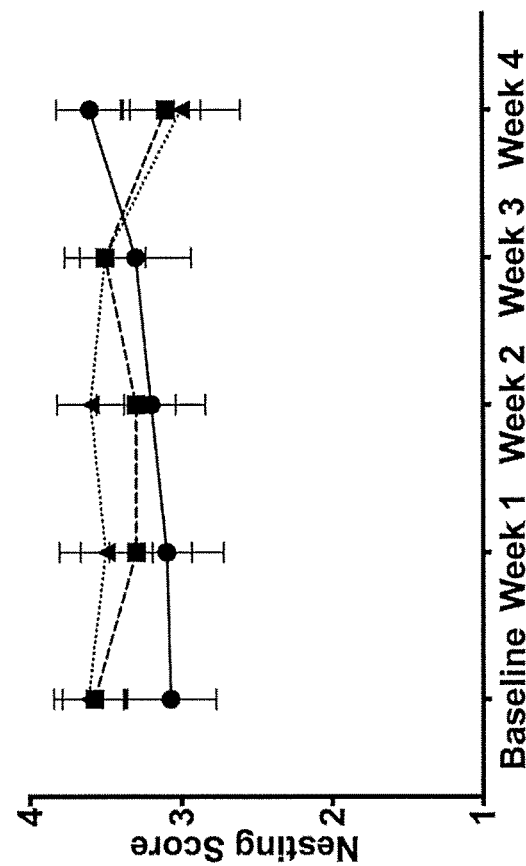
FIG. 2A is a graph showing the effects of the administration of exemplary cell division control protein 42 homolog (Cdc42) modulator compounds, ZCL278 (squares) or ZCL279 (triangles), on nesting behavior (measured on a relative scale from 1 to 4) in wild-type mice over the course of four weeks. For comparison, data from mice treated with a vehicle (sesame oil with 5 percent (%) dimethyl sulfoxide (DMSO)) is shown as a control (circles). "Baseline" on the x-axis refers to baseline behavior (i.e., prior to compound administration). N=10 per group. Values represent mean±sem.
Figures 3A, 3B:
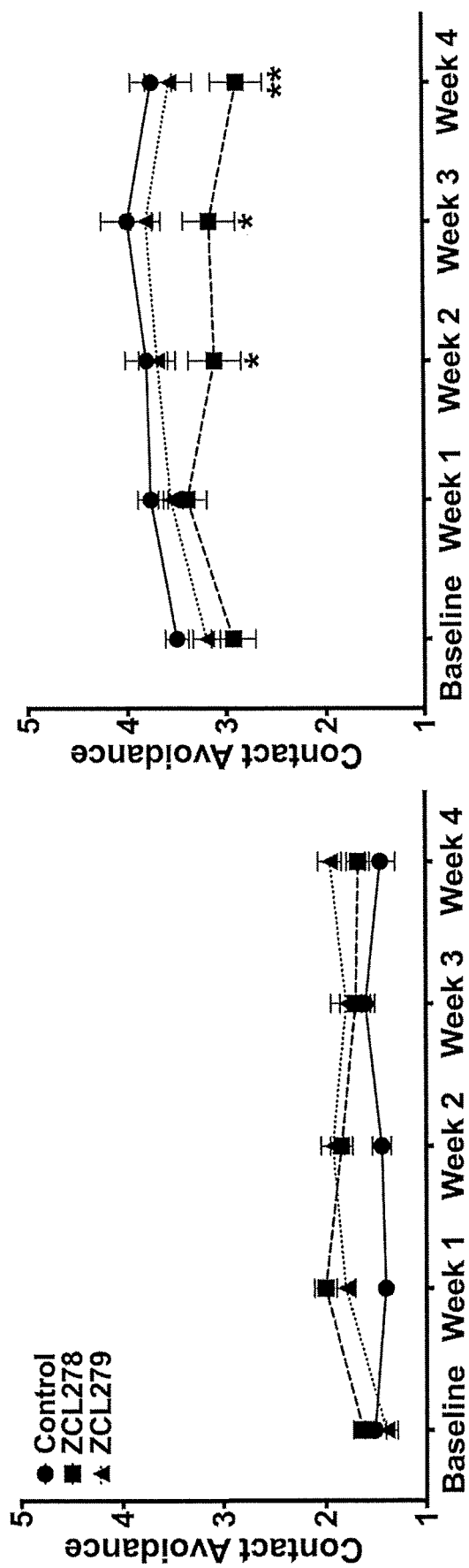
FIG. 3A is a graph showing the effects of the administration of exemplary cell division control protein 42 homolog (Cdc42) modulator compounds, ZCL278 (squares) or ZCL279 (triangles), on contact avoidance behavior (i.e., based on observation and using a relative scale of 1 to 5 adopted to evaluate the emotional reaction of the mouse) in wild-type mice over the course of four weeks. For comparison, data from mice treated with a vehicle (sesame oil with 5 percent (%) dimethyl sulfoxide (DMSO)) is shown as a control (circles). "Baseline" on the x-axis refers to baseline behavior (i.e., prior to compound administration). N=10 per group. Values represent mean±sem.
FIG. 3B is a graph showing the effects of the administration of exemplary cell division control protein 42 homolog (Cdc42) modulator compounds, ZCL278 (squares) or ZCL279 (triangles), on contact avoidance behavior (i.e., based on observation and using a relative scale of 1 to 5 adopted to evaluate the emotional reaction of the mouse) in triple transgenic mice of a mouse model of Alzheimer's disease (3×Tg-AD). Behavior was followed over the course of 4 weeks. For comparison, data from mice treated with vehicle (sesame oil with 5 percent (%) dimethyl sulfoxide (DMSO)) is shown as a control (circles). "Baseline" on the x-axis refers to baseline behavior (i.e., prior to compound administration). N=10 per group. Values represent mean±sem. *$p<0.05$, **$p<0.001$, relative to control.

See FIGS. 2A and 2B. ITSN-Cdc42 modulators, particularly ZCL279, improve instinctual behavior in the 3×Tg AD mouse model as determined by their ability to increase food burrowing and nesting behavior in the AD mouse model. See FIGS. 1B and 2B. Further, while transgenic mice generally showed higher levels of contact avoidance than WT mice, administration of the ITSN-Cdc42 modulators decrease contact avoidance. See FIGS. 3A and 3B. In particular, as shown in FIG. 3B, the administration of the modulators decreased contact avoidance levels by week 4 to levels approaching that of WT mice.

The administration of the modulators also increased hippocampal associative learning in the AD mouse model, as seen by the results of the eye blink conditioning test. Overall, the AD mice showed lower percentages of CR compared to WT mice. After six sessions, control WT mice showed close to 40% CR. Administration of ZCL278 and ZCL279 did not significantly change the CR percentage in WT mice. In comparison, after 6 training sessions control AD mice showed only about 20% CR. However, administration of ZCL279 was able to increase the CR percentage to about 35% after 6 training sessions.

Figure 4B:
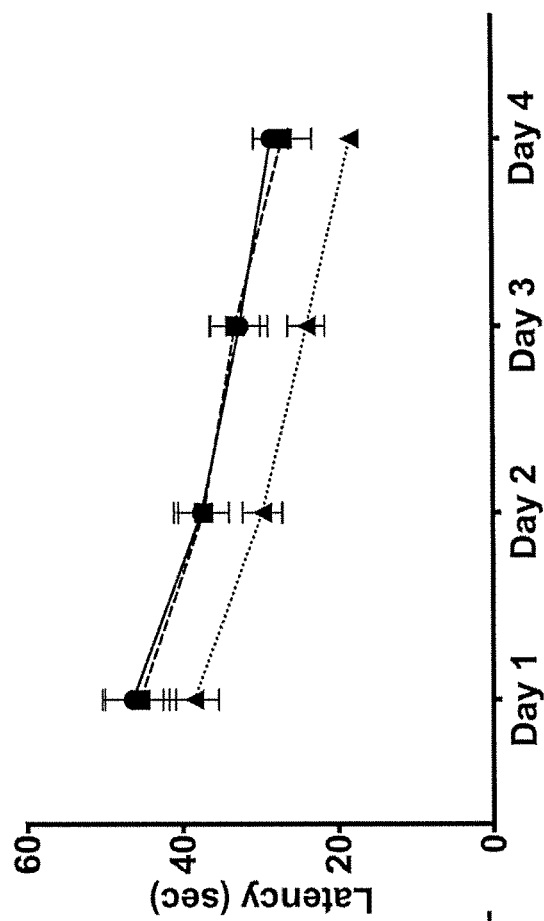
FIG. 4B is a graph showing the effects of the administration of exemplary cell division control protein 42 homolog (Cdc42) modulator compounds, ZCL278 (squares) or ZCL279 (triangles), on spatial memory ability (i.e., measured by the latency (in seconds) in finding a submerged platform in a Morris water maze test) in triple transgenic mice of a mouse model of Alzheimer's disease (3×Tg-AD). Behavior was tested over four trials on four separate days. For comparison, data from mice treated with vehicle (sesame oil with 5 percent (%) dimethyl sulfoxide (DMSO)) is shown as a control (circles). N=5 per group.
Figure 4A:
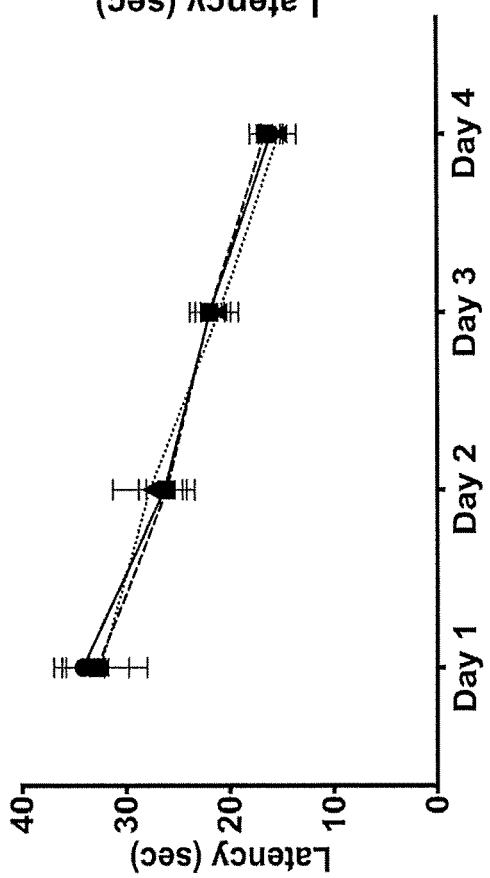
FIG. 4A is a graph showing the effects of the administration of exemplary cell division control protein 42 homolog (Cdc42) modulator compounds, ZCL278 (squares) or ZCL279 (triangles), on spatial memory ability (i.e., measured by the latency (in seconds) in finding a submerged platform in a Morris water maze test) in wild-type mice tested over four trials on four separate days. For comparison, data from mice treated with a vehicle (sesame oil with 5 percent (%) dimethyl sulfoxide (DMSO)) is shown as a control (circles). N=5 per group.

3×Tg AD mice were generally slower in finding the submerged platform in the water maze test than the WT mice. See FIGS. 4A and 4B. However, as shown in FIG. 4B, administration of ZCL279 improves spatial memory ability in the AD mouse model, as indicated by the reduced latency observed in finding the submerged platform. Spatial memory ability in 3×Tg AD mice treated with ZCL279 appeared similar to WT mice on Day 4.

Example 5

Brain Tissue Preparation and Analysis Methods

Tissue preparation: Mice were deeply anesthetized with 3% isoflourane vapor and euthanized by cervical dislocation. Brain tissues were harvested, and then either snap frozen for Western Blot analysis or fixed in 4% paraformaldehyde overnight for immunohistochemistry (IHC) analysis. Fixed brain tissues were washed with phosphate-buffered saline (PBS) and moved to cryoprotectant (30% sucrose in PBS) at 4° C. Once sunk in the cryoprotectant, brain tissues were subsequently embedded in the optimal cutting temperature compound (O.C.T) and rapidly frozen with chilled isopentane. Then, 8~30 μm thickness of cryostate section was applied to brain tissues, 30 μm sections were immersed in the PBS and store at 4° C. refrigerator, and 8 μm sections were store at −80° C. refrigerator.

Immunohistochemistry analysis: All sections were first treated with 1% $H_2O_2$ in PBS for 20 minutes at room temperature, then incubated with 0.5% Triton X-100 for 30 minutes and blocked for 30 minutes at room temperature. Brain tissues were incubated with primary antibodies from Table 6, below. 3,3-diaminobenzidine (DAB) staining (Vector Labs, Burlingame, California, United States of America) then proceeded according to the manufacturer's suggestions. All sections were eventually dehydrated in 95% ethanol and mounted on coverslips for light microscopy (Carl Zeiss, Thornwood, New York, United States of America).

Western blot analysis of protein extraction from brain lysates: Snap frozen brain tissues were pulverized in a mortar with liquid nitrogen, sonicated in radioimmunoprecipitation assay (RIPA) lysis buffer on ice, and subjected to protein concentration determination. Then, brain lysates were equally loaded (105 μg) onto an 18% tris-glycine gel (Invitrogen, Carlsbad, California, United States of America), transferred to PVDF membrane (Millipore, Billerica, Massachusetts, United States of America) and subjected to Western blot analysis. Subsequently, membranes were blocked and probed with primary antibodies from Table 6. GAPDH mouse antibody (Calbiochem, San Diego, California, United States of America) was used as a loading control.

Neuronal culture and JFC: Adult mouse cortical-hippocampal neurons were isolated from age-matched C57/BL and 3×Tg-AD mice as previously described (see Brewer & Torricelli, Nat. Protoc., 2007, 2(6):1490-1498) with minor changes. Neurons were cultured on poly-D-lysine coated coverslips in platelet-derived growth factor (PDGF, 1 μg/μL) and fibroblast growth factor (FGF, 1 μg/ul) supplemented neurobasal media (Invitrogen, Carlsbad, California, United States of America) for 7 days, 14 days or 21 days. Then, selected group of neurons were received control (Dulbecco's Modified Eagle Medium (DMEM)) treatment, ZCL278 (50 μM), or ZCL279 (50 μM) treatment for 24 h. Finally, neurons were fixed for 15 min in 4% paraformaldehyde. Following rinses with PBS, neurons were permeabilized with 0.5% Triton X-100 in PBS for 10 min. After blocking with 10% bovine serum albumin (BSA) in PBS for 30 min at 37° C., neurons were subsequently incubated with anti-MAP2 mouse antibody (Sigma, St. Louis, Missouri, United States of America), anti-active Cdc 42 mouse antibody (NewEast Biosciences, Malvern, Pennsylvania, United States of America), anti-pRac1/Cdc42 antibody, anti-pWASP rabbit antibody, anti-intersectin rabbit antibody (Millipore, Billerica, Massachusetts, United States of America), anti-PSD 95 rabbit antibody (Abcam, Cambridge, United Kingdom) or FITC-phalloidin and labeled with Cy3 or FITC secondary antibodies (The Jackson Laboratory, Bar Harbor, Maine, United States of America). Coverslips were mounted with prolong diamond antifade media (Molecular probes, Eugene, Oregon, United States of America) before visualization.

TABLE 6

Primary Antibodies.

| Name | MW | Cat Number | Supplier | Application |
|---|---|---|---|---|
| Rho GTPases | | | | |
| Anti-RhoA mouse | 24 kDa | #ARH03 | Cytoskeleton | WB: 1:1000 IHC: 1:500 |
| p-RhoA rabbit | 24 kDa | sc-32954 | Santa Cruz | WB: 1:1000 IHC: 1:500 |
| Active Rac1 mouse | 21 kDa | 26903 | NewEast | IP: 1:100 IHC: 1:500 |
| Rac1 mouse | 21 kDa | Ab33186 | Abcam | WB: 1:1000 IHC: 1:500 |
| Anti-Cdc42 mouse | 21 kDa | ACD03 | Cytoskeleton | WB: 1:1000 IHC: 1:500 |
| Active-Cdc42 mouse | 21 kDa | 26905 | NewEast | IP: 1:50 IHC: 1:500 |
| pRac1/cdc42 rabbit | 25 kDa | 07-896-I | Millipore | WB: 1:1000 IHC: 1:500 |
| Downstream effectors of Rho GTPases | | | | |
| WASP rabbit | 62 kDa | 4860 | Cell Signaling | WB: 1:1000 IHC: 1:500 |
| pWASP rabbit | 52 kDa | A0597 | Assay Biotech | WB: 1:1000 IHC: 1:500 |
| γPAK mouse | 62 kDa | sc-373740 | Santa Cruz | WB: 1:1000 IHC: 1:500 |
| αPAK mouse | 65 kDa | sc-166887 | Santa Cruz | WB: 1:1000 IHC: 1:500 |
| p-αPAK mouse | 65 kDa | sc-135755 | Santa Cruz | WB: 1:1000 IHC: 1:500 |
| Cofilin rabbit | 19 kDa | #5175 | Cell Signaling | WB: 1:1000 IHC: 1:500 |
| Upstream modulator of Rho GTPases | | | | |
| Anti-Intersectin-1 rabbit | 150~200 KDa | ABS984 | Millipore | WB: 1:1000 IHC: 1:500 |
| AD Pathology | | | | |
| 4G8 mouse | | | | IHC: 1:1000 |

TABLE 6-continued

Primary Antibodies.

| Name | MW | Cat Number | Supplier | Application |
|---|---|---|---|---|
| AT-8 rabbit | 55 kDa | 44-768G | ThermoFisher | IHC: 1:1000 |
| Iba-1 rabbit | 17 kDa | 019-19741 | Wako | IHC: 1:500 |

Synaptic Analysis

| Synaptophysin rabbit | 38 kDa | 5461 | Cell Signaling | WB: 1:1000 IHC: 1:500 |
| PSD-95 rabbit | 95 kDa | 3450 | Cell Signaling | WB: 1:1000 IHC: 1:500 |

WB = Western Blot;
IHC = Immunohistochemistry;
IP: Immunoprecipitation

Effects of ZCL Compound Treatment on Mouse Neuronal Culture:

Adult mouse cortical-hippocampal neurons were collected from age matched (4 months old) WT and 3xTg-AD mice. Neurons were cultured in vitro for 7 days. Selected groups of neurons were submitted to 50 μM ZCL compound treatment (ZCL278 or ZCL279) for 24 hours. All neurons were fixed by 4% PFA after 24 h treatment, and then submitted to immunofluorescent analysis. 3xTg AD neurons showed significantly reduced neuronal branching complexity (F-actin and MAP2) which was reverted by ZCL compound treatment. There was recovery of Intersectin and pWASP intensity as well although it was not as striking as F-actin and MAP2 staining.

Adult mouse cortical-hippocampal neurons were also collected from age matched (8 months old) WT and 3xTg-AD mice. Neurons were cultured in vitro for 7 days. Selected groups of neurons were submitted to 50 μM ZCL compound treatment (ZCL278 or ZCL279) for 24 hours. All neurons were fixed by 4% PFA after 24h treatment, and then submitted to immunofluorescent analysis. The effects of ZCL compound on F-actin and MAP2, as well as on active Cdc42 and pRac1-Cdc42 were less striking than that on mouse neurons obtained from 4-month-old mice, except for the effects of ZCL279 on F-actin and active Cdc42.

Figure 5B:
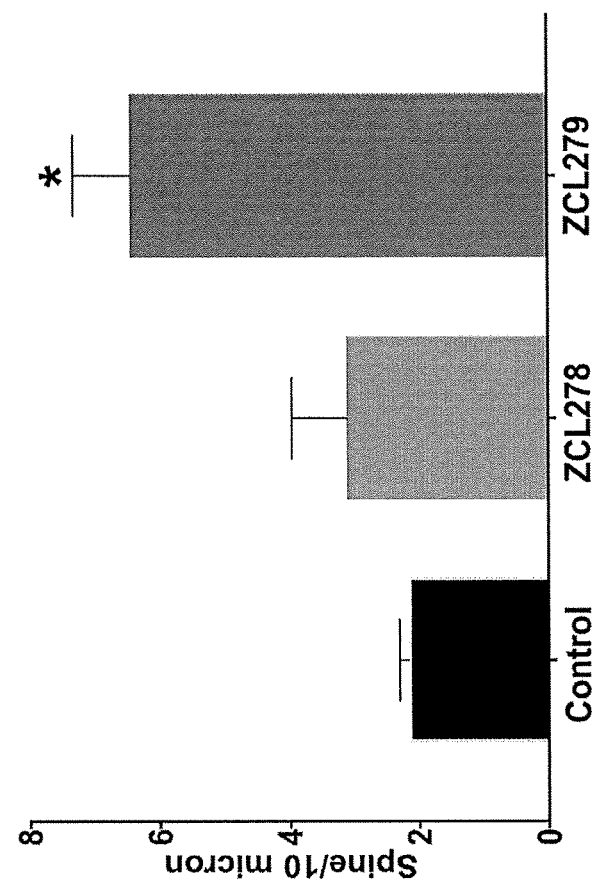
FIG. 5B is a graph showing the effects of the administration of exemplary cell division control protein 42 homolog (Cdc42) modulator compounds, ZCL278 (middle) or ZCL279 (left), on the density of neuronal spines in cortical-hippocampal neurons collected from triple transgenic mice of a mouse model of Alzheimer's disease (3×Tg-AD) and cultured. For comparison, data from neurons treated with a vehicle (sesame oil with 5 percent (%) dimethyl sulfoxide (DMSO)) is shown as a control (circles). The density of neuronal spines was measured as the number of spines per 10 microns. Values represent the mean±sem. N=5 per group. *$p<0.01$, relative to control.
Figure 5A:
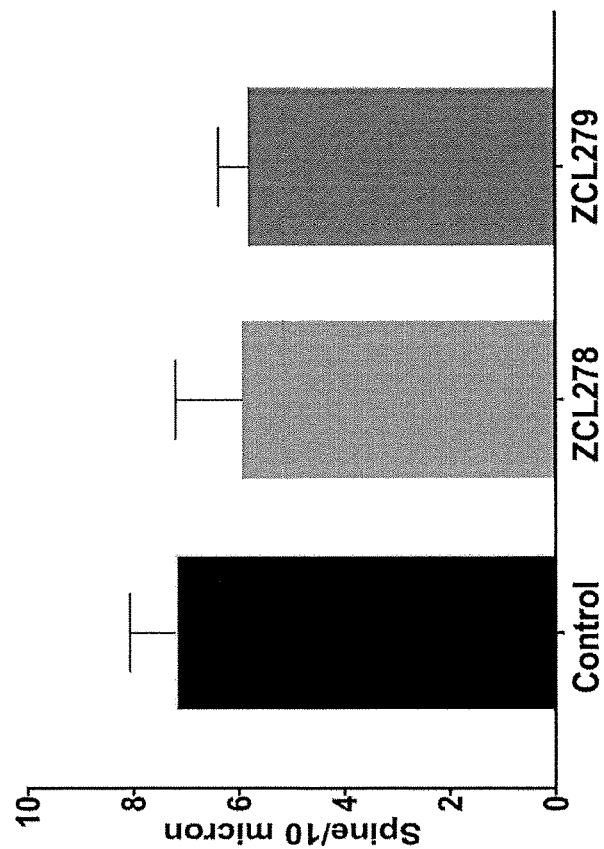
FIG. 5A is a graph showing the effects of the administration of exemplary cell division control protein 42 homolog (Cdc42) modulator compounds, ZCL278 (middle) or ZCL279 (left), on the density of neuronal spines in cortical-hippocampal neurons collected from wild-type adult mice and cultured. For comparison, data from neurons treated with a vehicle (sesame oil with 5 percent (%) dimethyl sulfoxide (DMSO)) is shown as a control (circles). The density of neuronal spines was measured as the number of spines per 10 microns. Values represent the mean±sem. N=5 per group.

Adult mouse cortical-hippocampal neurons were additionally collected from age matched (12 months old) WT and 3xTg-AD mice. Neurons were cultured in vitro for 21 days. Selected group of neurons were submitted to 50 μM selected ZCL compound treatment (ZCL278 or ZCL279) for 24 hours. All neurons were fixed by 4% PFA after 24h treatment, and then submitted to immunofluorescent analysis. The density of neuronal spines was measured as the ratio of number of spines per 10 microns. See FIGS. 5A and 5B.

Example 6

Neuropathogenesis in AD Mouse Model after ITSN-Cdc42 Modulator Treatment

Methods: Brain tissues collected from each treatment group of mice from the behavior studies were subjected to pathological analysis (e.g., immunohistochemical analysis, as described above in Example 5). Microglials were revealed by Iba-1. Amyloid deposits were revealed by antibody 4G8 while tau phosphorylation was indicated by antibody AT8 immunostaining. Growth cone dynamics and spine motility were either recorded with time-lapse microscopy or stained by using the fluorescein isothiocyanate (FITC) or Cyanine Dye 3 (Cy3)-conjugated Phalloidin.

Figure 6:
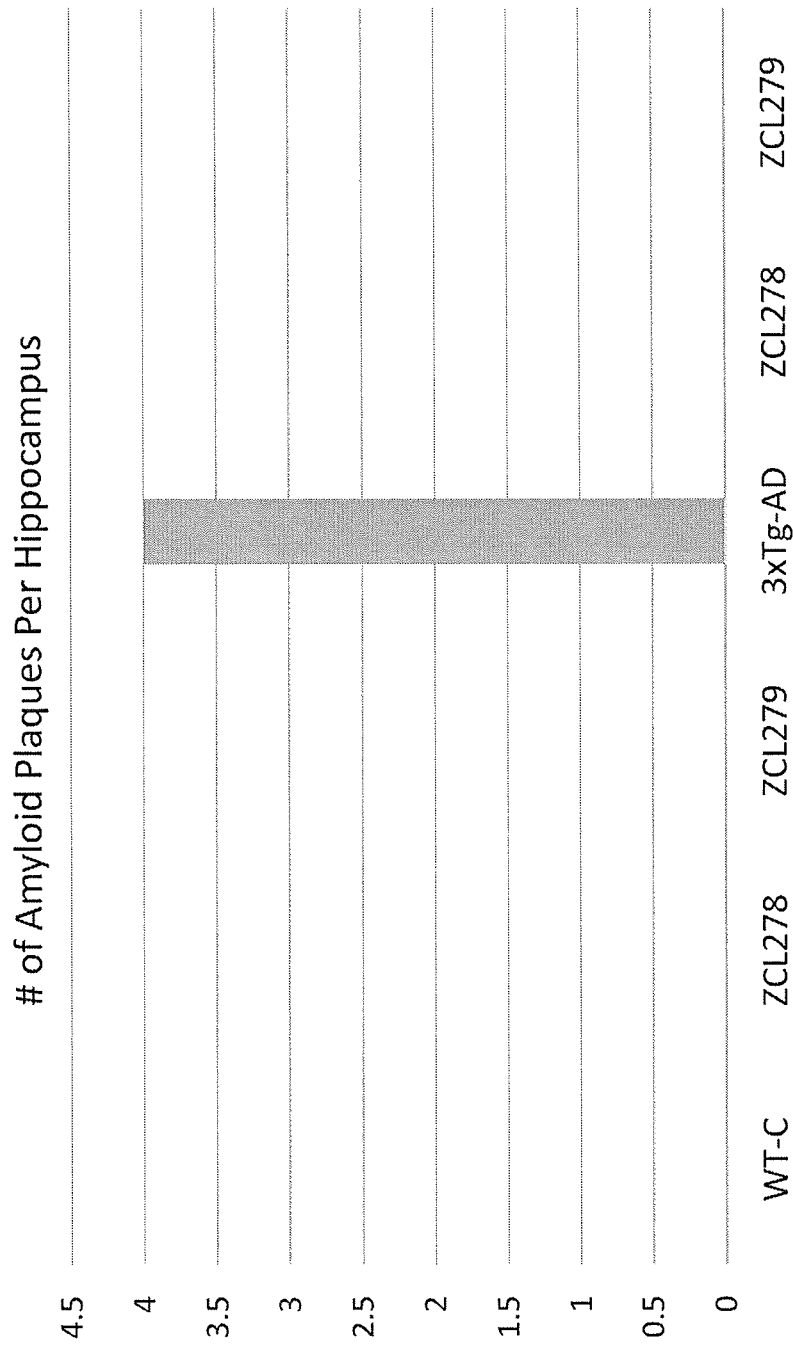
FIG. 6 is a graph showing the effects of the administration of exemplary cell division control protein 42 homolog (Cdc42) modulator compounds, ZCL278 or ZCL279, on the deposition of amyloid plaques in the hippocampus of triple transgenic mice of a mouse model of Alzheimer's disease (3×Tg-AD) or wild-type control mice (WT-C). Six-months-old mice were treated with modulator compound for 2 months, after which time the mouse brains were analyzed by immunostaining for amyloid plaques. The average number of amyloid plaques per hippocampus is shown for, from left to right: untreated WT-C, WT-C treated with ZCL278, WT-C treated with ZCL279, untreated 3×Tg-AD, 3×Tg-AD treated with ZCL278, and 3×Tg-AD treated with ZCL279. N=2 per group.

Results: The effects of modulator compound administration on amyloid deposition in the hippocampus is summarized in FIG. 6. No amyloid deposition was observed in the hippocampus of WT mice, regardless of whether or not the mice received administration of ZCL278 or ZCL279. However, an average of 4 amyloid deposits was observed in the hippocampus in the untreated 3xTg AD mice. The 3xTg AD mice treated with either ZCL278 or ZCL279 showed no amyloid deposits.

Untreated 3xTg AD mice showed evidence of phosphorylation of microtubule-associated tau in the dentate gyrus of the hippocampus when visualized under microscope. This phosphorylation was not evident in the dentate gyrus of the hippocampus of 3xTg AD mice treated with either ZCL278 or ZCL279. Both treated and untreated WT mice showed no evidence of such phosphorylation of microtubule-associated tau in the dentate gyrus.

Figure 7:
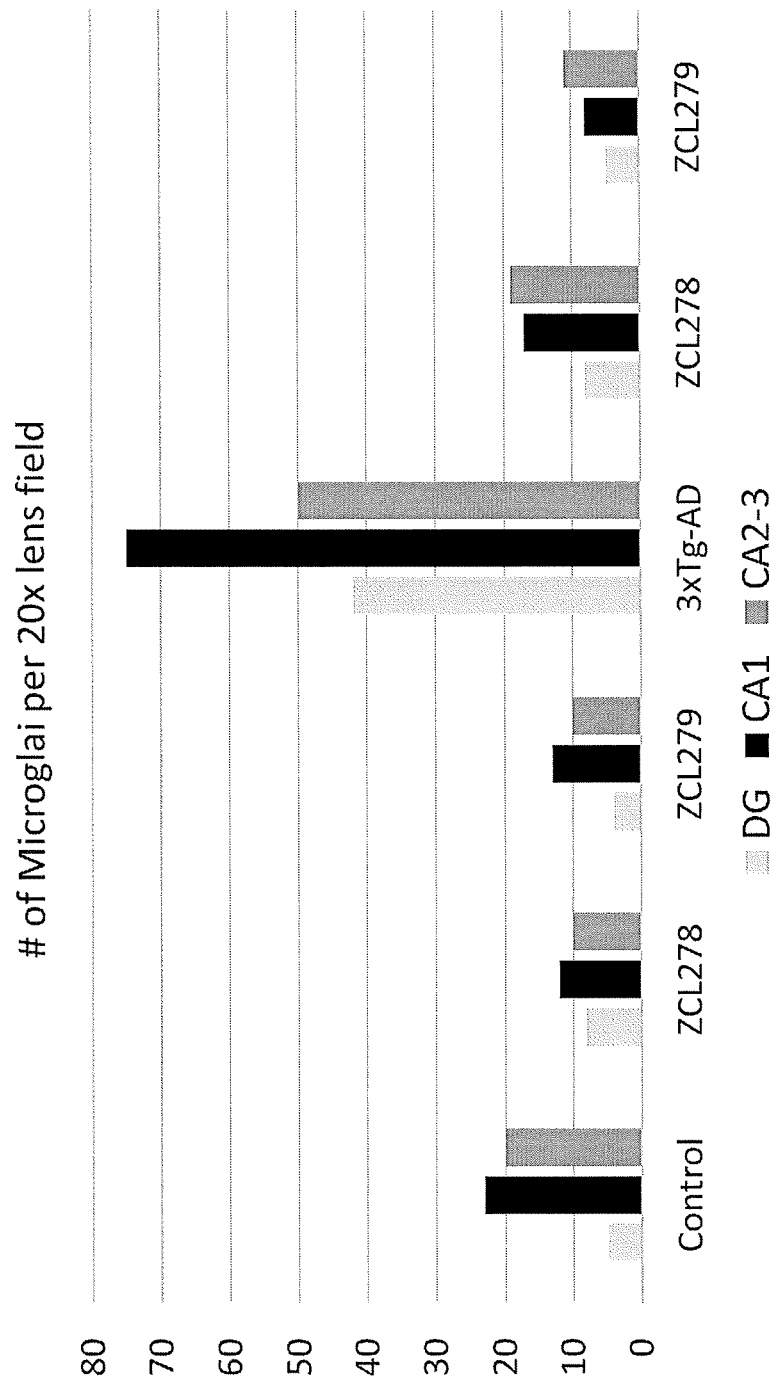
FIG. 7 is a graph showing the effects of the administration of exemplary cell division control protein 42 homolog (Cdc42) modulator compounds, ZCL278 or ZCL279, on the proliferation of microglial cells in different regions (Dentate Gyrus (DG), light grey bars; *Cornu Ammonis* areas 1 (CA1), black bars; and *Cornu Ammonis* areas 2-3 (CA2-3), medium grey bars) in the hippocampus of triple transgenic mice of a mouse model of Alzheimer's disease (3×Tg-AD, right half of graph) and in the hippocampus of wild type mice (Control, left half of graph). As indicated at the bottom of the graph, the mice were treated with a modulator compound (ZCL278 or ZCL279) or with vehicle (sesame oil with 5% dimethyl sulfoxide (DMSO)) (Control or 3×Tg-AD). Data is show as the number of microglia per microscope lens field (20 times objective lens).

The accumulation of pro-inflammatory microglia in different regions (i.e., the dentate gyrus (DG), CA1 and the Cornu Ammonis regions 2 and 3 (CA2-3)) of the hippocampus in treated and untreated W and 3xTg AD mice is summarized in Table 7, below. See also, FIG. 7. For example, as indicated in the table, in untreated 3xTg-AD mice, an average of about 42 microglia cells were observed per microscope field (20x objective lens) in the DG, an average of about 75 microglia cells were observed per microscope field in CA1, and an average of about 50 microglia cells were observed per microscope field in CA2-3. For 3xTg AD mice treated with ZCL278, the average number of microglia cells per field was reduced to about 8 in the DG, about 17 in CA1, and about 19 in CA2-3. For 3xTg AD mice treated with ZCL279, the average number of microglia cells per field was reduced to about 5 in the DG, about 8 in CA1, and about 11 in CA2-3. Thus, administration of the modulators reduced pro-inflammatory microglia accumulation to levels similar to that seen in untreated WT mice (i.e., an average of about 5 microglia cells in DG, about 23 microglia cells in CA1, and about 20 microglia cells in CA2-3.

TABLE 7

Average Number of Microglia per Microscope Field.

| Group | DG | CA1 | CA2-3 |
|---|---|---|---|
| Control (untreated WT mice) | 5 | 23 | 20 |
| WT mice treated with ZCL278 | 8 | 12 | 10 |
| WT mice treated with ZCL279 | 4 | 13 | 10 |
| Untreated 3xTg-AD mice | 42 | 75 | 50 |
| 3xTg-AD mice treated with ZCL278 | 8 | 17 | 19 |
| 3xTg-AD mice treated with ZCL279 | 5 | 8 | 11 |

Finally, the modulators also appeared to inhibit actin dynamics at growth cone in culture adult neurons isolated from 3xTg AD mice.

Example 7

Additional Compound Screening

Cdc42-GEF-assays were conducted on additional screening compounds in batches of 9 compounds per batch as described above in Example 2 using ZCL278 and ZCL367 as standards. Screening compounds were taken from the Specs Chemistry Database of 197,000 compounds for small molecule or the National Cancer Institute Compound Library. Table 8, below, shows additional Cdc42 inhibitor compounds found during the screening, with inhibitor activity expressed as percentages of ZCL367 normalized to batch. More potent inhibitors are those that have activity that is less than 100% of ZCL367. These ZCL367-like inhibitors do not appear to affect Cdc42-mantGTP binding without GEF and inhibit Cdc42-mantGTP binding with GEF. Table 9, below, shows additional Cdc42 dual function compounds that appear to have activity similar to ZCL278, with activator activity expressed as percentages of ZCL278 activity normalized to batch. More potent activators are those that have activity of more than 100% of ZCL278. These compounds promote Cdc42-mantGTP binding without GEF. It is possible that these compounds can inhibit Cdc42-mantGTP binding with GEF. Table 10, below, shows additional Cdc42 activator compounds, with activator activity expressed as percentages of ZCL278 activity normalized to batch. More potent activators are those that have activity of more than 100% of ZCL278. These compounds appear to have activity like ZCL279. In the absence of GEF, these compounds do not appear to have an effect on intrinsic Cdc42-mantGTP binding (low baseline slope relative to ZCL278). However, upon the addition of GEF, the compounds appear to facilitate the binding of mantGTP to Cdc42 (high assay slope, relative to ZCL278)

TABLE 8

ZCL367-like Cdc42 Inhibitor Compounds from Additional Screening.

| Compound | Structure | % ZCL367 |
| --- | --- | --- |
| ZCL1105 | 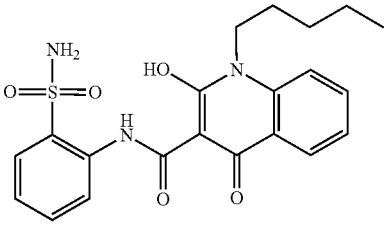 [SMILES: CCCCCn1c(O)c(C(=O)Nc2ccccc2S(N)(=O)=O)c(=O)c2ccccc21] | 3.42 |
| ZCL1102 | 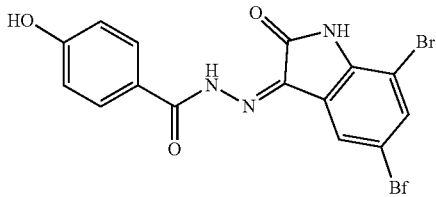 | 9 |
| ZCL1115 | 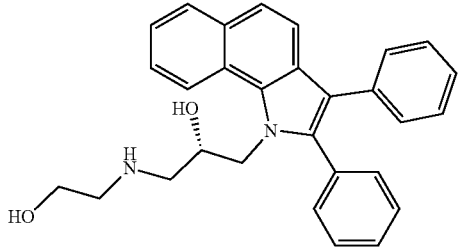 [SMILES: OCCNC[C@H](O)Cn1c(-c2ccccc2)c(-c2ccccc2)c2ccc3ccccc3c21] | 27.33 |
| ZCL1125 | 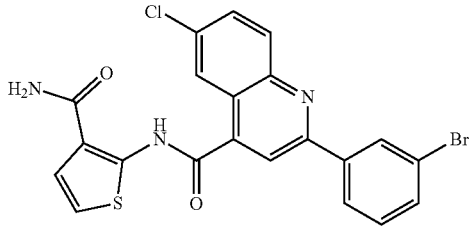 [SMILES: NC(=O)c1ccsc1NC(=O)c1cc(-c2cccc(Br)c2)nc2ccc(Cl)cc12] | 28.67 |
| ZCL1100 | 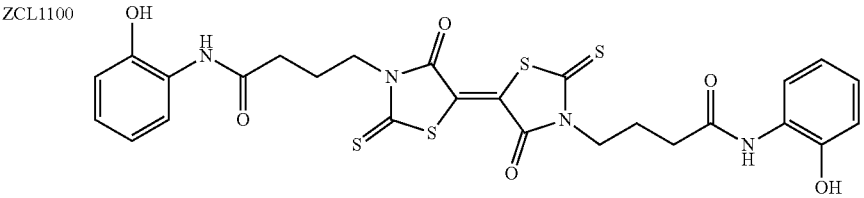 | 29.97 |

TABLE 8-continued

ZCL367-like Cdc42 Inhibitor Compounds from Additional Screening.

| Compound | Structure | % ZCL367 |
|---|---|---|
| ZCL1118 | 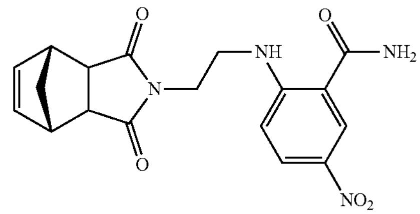 [SMILES: NC(=O)c1cc([N+](=O)[O-])ccc1NCCN1C(=O)C2C(C1=O)[C@H]1C=C[C@@H]2C1] | 46.77 |
| ZCL1109 | 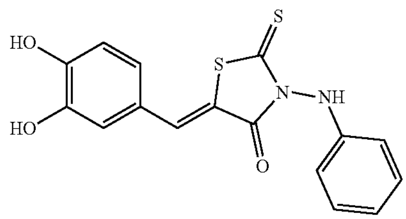 [SMILES: O=C1/C(=C/c2ccc(O)c(O)c2)SC(=S)N1Nc1ccccc1] | 55.74 |
| ZCL1107 | 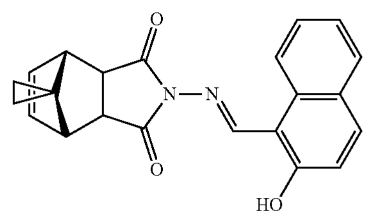 | 62.37 |
| NSC143095 | 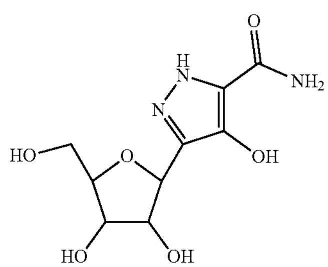 [SMILES: NC(=O)c1[nH]nc(C2OC(CO)C(O)C2O)c1O] | 62.98 |
| NSC25268 | 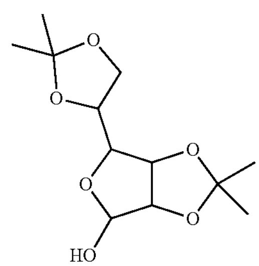 | 64.92 |
| NSC407188 | 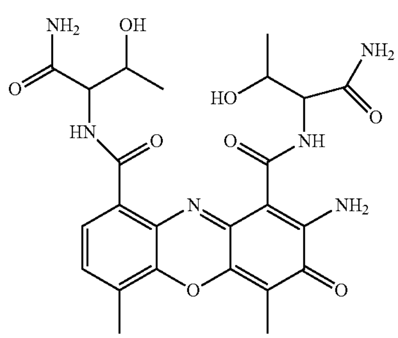 [SMILES: Cc1c2oc3c(C)ccc(C(=O)NC(C(N)=O)C(C)O)c3nc-2c(C(=O)NC(C(N)=O)C(C)O)c(N)c1=O] | 70.58 |

TABLE 8-continued

ZCL367-like Cdc42 Inhibitor Compounds from Additional Screening.

| Compound | Structure | % ZCL367 |
|---|---|---|
| ZCL1117 | 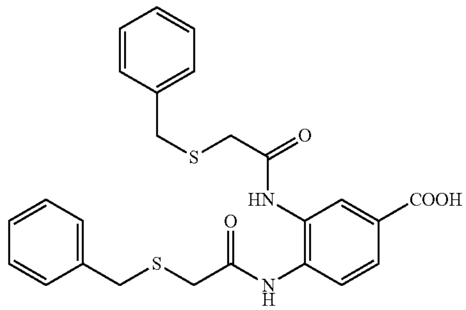 [SMILES: O=C(CSCc1ccccc1)Nc1ccc(C(=O)O)cc1NC(=O)CSCc1ccccc1] | 74.15 |
| ZCL1120 | 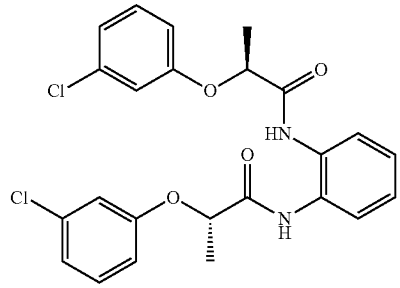 [SMILES: C[C@H](Oc1cccc(Cl)c1)C(=O)Nc1ccccc1NC(=O)[C@H](C)Oc1cccc(Cl)c1] | 81.19 |
| ZCL1139 | 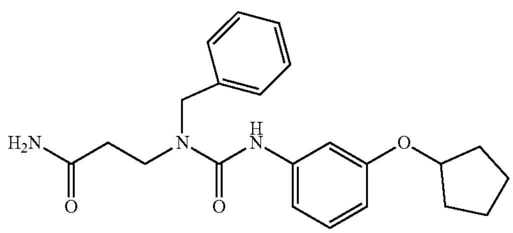 [SMILES: NC(=O)CCN(Cc1ccccc1)C(=O)Nc1cccc(OC2CCCC2)c1] | 88.55 |
| ZCL1137 | 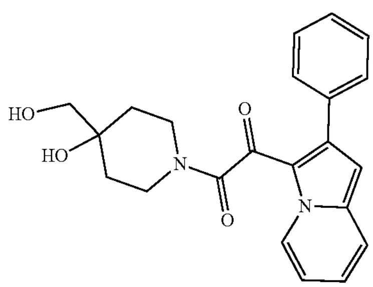 [SMILES: O=C(C(=O)N1CCC(O)(CO)CC1)c1c(-c2ccccc2)cc2ccccn12] | 93.54 |
| ZCL1127 | 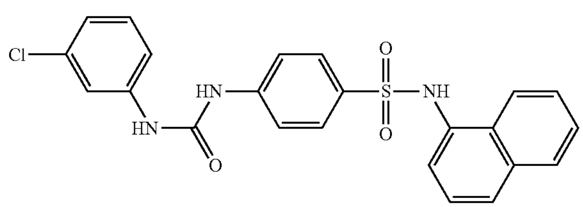 [SMILES: O=C(Nc1ccc(S(=O)(=O)Nc2cccc3ccccc23)cc1)Nc1cccc(Cl)c1] | 98.5 |
| ZCL367 | 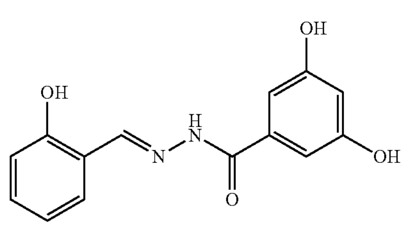 [SMILES: O=C(N/N=C/c1ccccc1O)c1cc(O)cc(O)c1] | 100 |

TABLE 8-continued
ZCL367-like Cdc42 Inhibitor Compounds from Additional Screening.
| Compound | Structure | % ZCL367 |
|---|---|---|
| ZCL1110 | 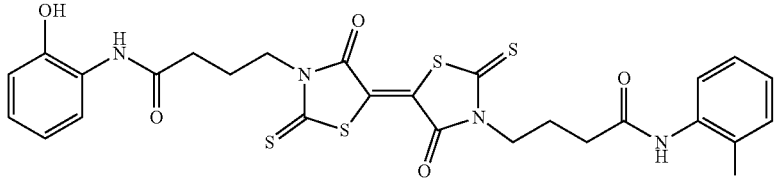 | 104.15 |
| ZCL1111 | 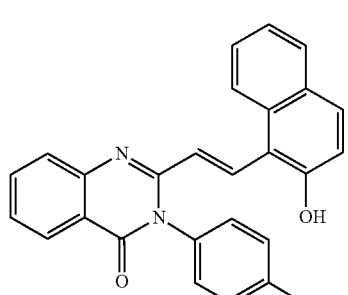 | 109.35 |
TABLE 9
ZCL278-like Cdc42 Dual Function Modulator Compounds from Additional Screening.
| Compound | Structure | % ZCL278 |
|---|---|---|
| ZCL1144 | 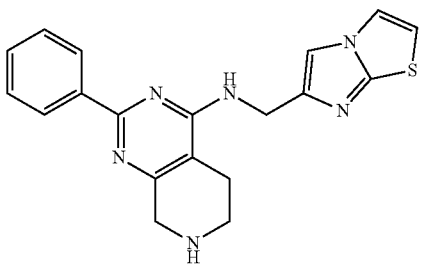 [SMILES: c1ccc(-c2nc3c(c(NCc4cn5ccsc5n4)n2)CCNC3)cc1] | 454.3 |
| NSC128731 | 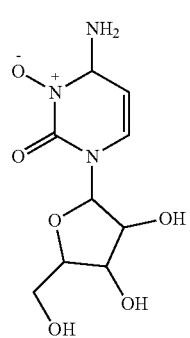 [SMILES: NC1C=CN(C2OC(CO)C(O)C2O)C(=O)N1O] | 108.28 |

TABLE 9-continued

ZCL278-like Cdc42 Dual Function Modulator Compounds from Additional Screening.

| Compound | Structure | % ZCL278 |
|---|---|---|
| ZCL1139 | 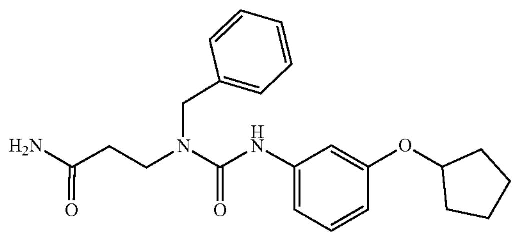 [SMILES: NC(=O)CCN(Cc1ccccc1)C(=O)Nc1cccc(OC2CCCC2)c1] | 100.29 |
| ZCL278 | 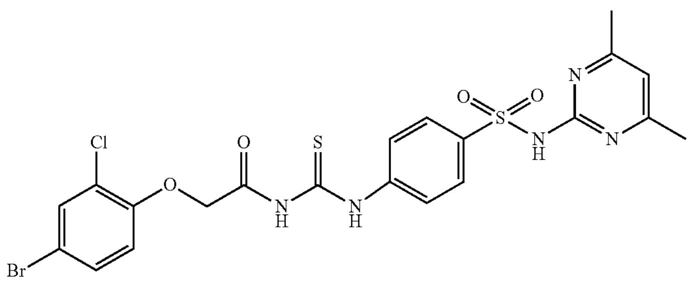 [SMILES: Cc1cc(C)nc(NS(=O)(=O)c2ccc(NC(=S)NC(=O)COc3ccc(Br)cc3Cl)cc2)n1] | 100 |

TABLE 10

ZCL279-like Cdc42 Modulator Compounds from Additional Screening.

| Compound | Structure | % ZCL278 (without GEF) | % ZCL278 (with GEF) |
|---|---|---|---|
| ZCL1119 | 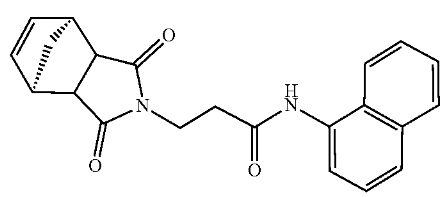 [SMILES: O=C(CCN1C(=O)C2C(C1=O)[C@H]1C=C[C@@H]2C1)Nc1cccc2ccccc12] | 59.173 | 103.291 |
| ZCL1124 | 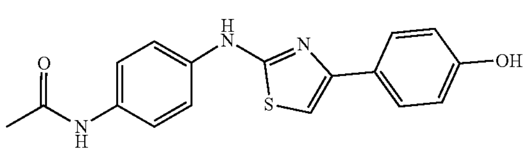 [SMILES: CC(=O)Nc1ccc(Nc2nc(-c3ccc(O)cc3)cs2)cc1] | 63.125 | 97.542 |
| ZCL1142 | 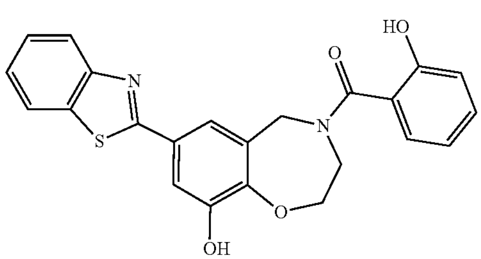 [SMILES: O=C(c1ccccc1O)N1CCOc2c(O)cc(-c3nc4ccccc4s3)cc2C1] | 69.001 | 98.499 |

TABLE 10-continued

ZCL279-like Cdc42 Modulator Compounds from Additional Screening.

| Compound | Structure | % ZCL278 (without GEF) | % ZCL278 (with GEF) |
|---|---|---|---|
| ZCL1143 | 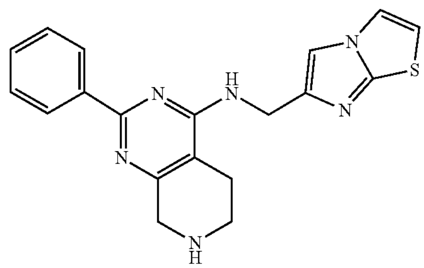 [SMILES: c1ccc(-c2nc3c(c(NCc4cn5ccsc5n4)n2)CCNC3)cc1] | 45.056 | 96.811 |
| NSC129911 | 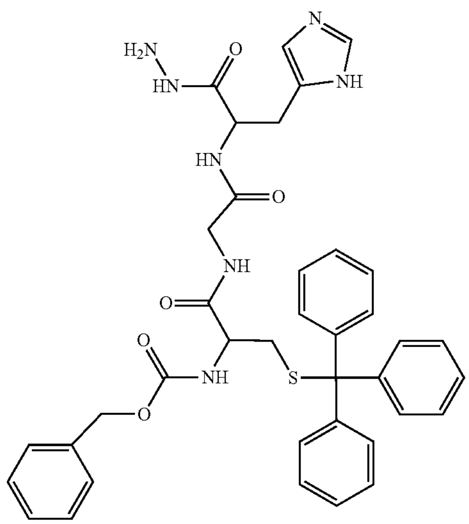 [SMILES: NNC(=O)C(Cc1cnc[nH]1)NC(=O)CNC(=O)C(CSC(c1ccccc1)(c1ccccc1)c1ccccc1)NC(=O)OCc1ccccc1] | 31.919 | 96.611 |
| NSC158437 | 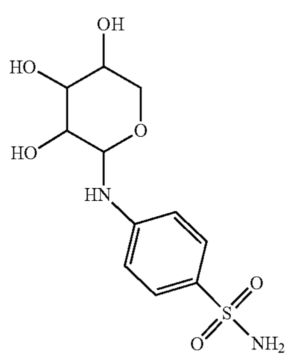 [SMILES: NS(=O)(=O)c1ccc(NC2OCC(O)C(O)C2O)cc1] | 12.229 | 127.593 |
| NSC136024 | 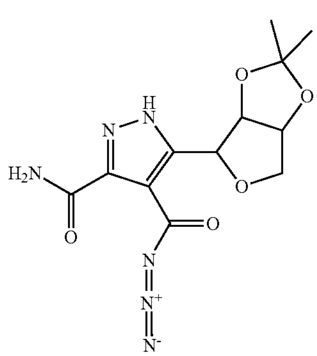 [SMILES: CC1(C)OC2COC(c3[nH]nc(C(N)=O)c3C(=O)N=[N+]=[N-])C2O1] | 20.812 | 82.316 |

TABLE 10-continued

ZCL279-like Cdc42 Modulator Compounds from Additional Screening.

| Compound | Structure | % ZCL278 (without GEF) | % ZCL278 (with GEF) |
|---|---|---|---|
| NSC81461 | 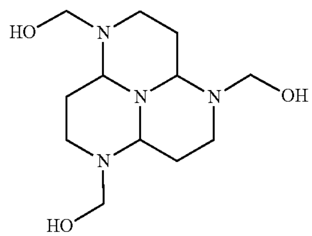 [SMILES: OCN1CCC2N(CO)CCC3N(CO)CCC1N23] | 15.832 | 92.160 |
| NSC111600 | 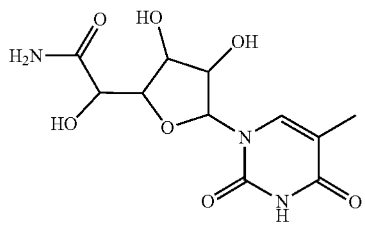 [SMILES: Cc1cn(C2OC(C(O)C(N)=O)C(O)C2O)c(=O)[nH]c1=O] | 9.098 | 185.829 |
| NSC94024 | 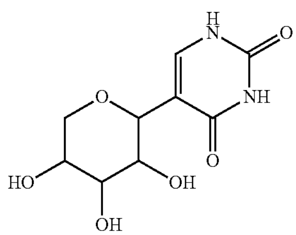 [SMILES: O=c1[nH]cc(C2OCC(O)C(O)C2O)c(=O)[nH]1] | 34.327 | 96.844 |

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of treating Alzheimer's disease in a subject in need of treatment thereof, wherein the method comprises administering to the subject a compound having the structure:

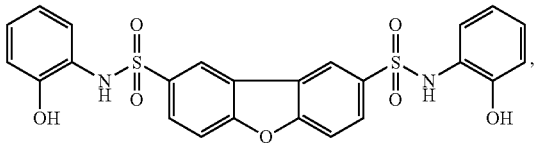 [SMILES: O=S(=O)(Nc1ccccc1O)c1ccc2oc3ccc(S(=O)(=O)Nc4ccccc4O)cc3c2c1]

or a pharmaceutically acceptable salt thereof.

* * * * *